(12) United States Patent
Czartoski et al.

(10) Patent No.: US 8,679,121 B2
(45) Date of Patent: Mar. 25, 2014

(54) INTRAMEDULLARY NAIL WITH OBLIQUE OPENINGS

(75) Inventors: Timothy J. Czartoski, Fort Wayne, IN (US); Dale G. Davison, Akron, OH (US); William Muhammad, Fort Wayne, IN (US); Jack Dean Cole, Orlando, FL (US); Berton R. Moed, St. Louis, MO (US); Tracy J. Watson, Town & Country, MO (US); Michael Karl-Heinz Wich, Berlin (DE)

(73) Assignee: Biomet C.V., Gibraltar (GI)

( * ) Notice: Subject to any disclaimer, the term of this patent is extended or adjusted under 35 U.S.C. 154(b) by 388 days.

(21) Appl. No.: 12/542,011

(22) Filed: Aug. 17, 2009

(65) Prior Publication Data
US 2009/0306666 A1    Dec. 10, 2009

Related U.S. Application Data

(62) Division of application No. 11/262,654, filed on Oct. 31, 2005, now abandoned.

(51) Int. Cl.
*A61B 17/56* (2006.01)

(52) U.S. Cl.
USPC .............................................. 606/64; 606/62

(58) Field of Classification Search
USPC ......... 606/62–68, 916, 104; 623/20.35, 20.36
See application file for complete search history.

(56) References Cited

U.S. PATENT DOCUMENTS

| | | | |
|---|---|---|---|
| 3,433,220 A | 3/1969 | Zickel | |
| 4,622,959 A | 11/1986 | Marcus | |
| 4,640,271 A * | 2/1987 | Lower | 606/65 |
| 4,653,489 A | 3/1987 | Tronzo | |
| 4,911,153 A * | 3/1990 | Border | 606/98 |
| 4,976,258 A * | 12/1990 | Richter et al. | 606/64 |

(Continued)

FOREIGN PATENT DOCUMENTS

| | | |
|---|---|---|
| EP | 0550814 B1 | 7/1993 |
| EP | 0793451 B1 | 9/1997 |
| EP | 0486483 B1 | 5/2002 |
| WO | WO 01/39679 A1 | 7/2001 |

OTHER PUBLICATIONS

Grosse & Kempf® Locking Nail System Operative Technique. Stryker Trauma GmbH, 2005.

(Continued)

*Primary Examiner* — Jan Christopher Merene
(74) *Attorney, Agent, or Firm* — Harness, Dickey

(57) ABSTRACT

An intramedullary nail for use in a medullary canal of a long bone is provided. The nail includes a body defining a longitudinal axis of the body and an external periphery of the body for fitting in the medullary canal of the long bone. The body has a first internal wall thereof defining a first opening through the body. The first opening defines a first opening centerline. The body has a second internal wall of the body defining a second opening through the body. The second opening defines a second opening centerline. The first opening centerline and the second opening centerline are oblique with respect to each other. The longitudinal axis of the body and the first opening centerline form an acute angle between the longitudinal axis of the body and the first opening centerline. The longitudinal axis of the body and the second opening centerline forming an acute angle between the longitudinal axis of the body and the second opening centerline.

20 Claims, 40 Drawing Sheets

(56) References Cited

U.S. PATENT DOCUMENTS

| | | | |
|---|---|---|---|
| 5,041,115 A | 8/1991 | Frigg et al. | |
| 5,127,913 A * | 7/1992 | Thomas, Jr. | 606/62 |
| 5,429,640 A * | 7/1995 | Shuler et al. | 606/64 |
| 5,472,444 A | 12/1995 | Huebner et al. | |
| 5,480,402 A | 1/1996 | Kim | |
| 5,531,748 A * | 7/1996 | de la Caffiniere | 606/62 |
| 5,548,600 A | 8/1996 | Fredrickson et al. | |
| 5,549,610 A | 8/1996 | Russell et al. | |
| 5,573,536 A | 11/1996 | Grosse et al. | |
| 5,779,705 A | 7/1998 | Matthews | |
| 6,010,505 A | 1/2000 | Asche et al. | |
| 6,010,506 A | 1/2000 | Gosney et al. | |
| 6,019,761 A * | 2/2000 | Gustilo | 606/62 |
| 6,080,159 A * | 6/2000 | Vichard | 606/64 |
| 6,106,528 A | 8/2000 | Durham et al. | |
| 6,123,708 A | 9/2000 | Kilpela et al. | |
| 6,221,074 B1 * | 4/2001 | Cole et al. | 606/62 |
| 6,342,055 B1 | 1/2002 | Eisermann et al. | |
| 6,488,684 B2 * | 12/2002 | Bramlet et al. | 606/62 |
| 6,702,816 B2 * | 3/2004 | Buhler | 606/62 |
| 6,855,146 B2 | 2/2005 | Frigg et al. | |
| 7,247,156 B2 | 7/2007 | Ekholm et al. | |
| 7,527,627 B2 * | 5/2009 | Ferrante et al. | 606/64 |
| 7,763,021 B2 * | 7/2010 | Cole et al. | 606/64 |
| 8,114,078 B2 * | 2/2012 | Aschmann | 606/64 |
| 2002/0183750 A1 * | 12/2002 | Buhler | 606/62 |
| 2003/0004514 A1 | 1/2003 | Frigg et al. | |
| 2004/0127898 A1 * | 7/2004 | Adam | 606/64 |
| 2004/0158252 A1 | 8/2004 | Prager et al. | |
| 2004/0172026 A1 | 9/2004 | Ekholm et al. | |
| 2005/0055024 A1 * | 3/2005 | James et al. | 606/64 |
| 2005/0101958 A1 | 5/2005 | Adam | |
| 2005/0277936 A1 * | 12/2005 | Siravo et al. | 606/62 |
| 2006/0084999 A1 * | 4/2006 | Aschmann | 606/64 |

OTHER PUBLICATIONS

Russell, Thomas A. et al. The Smith & Nephew Tibial Interlocking Nails, Smith & Nephew, Inc. 1997.

Long Gamma® Locking Nail. Stryker Corporation, 1999.

* cited by examiner

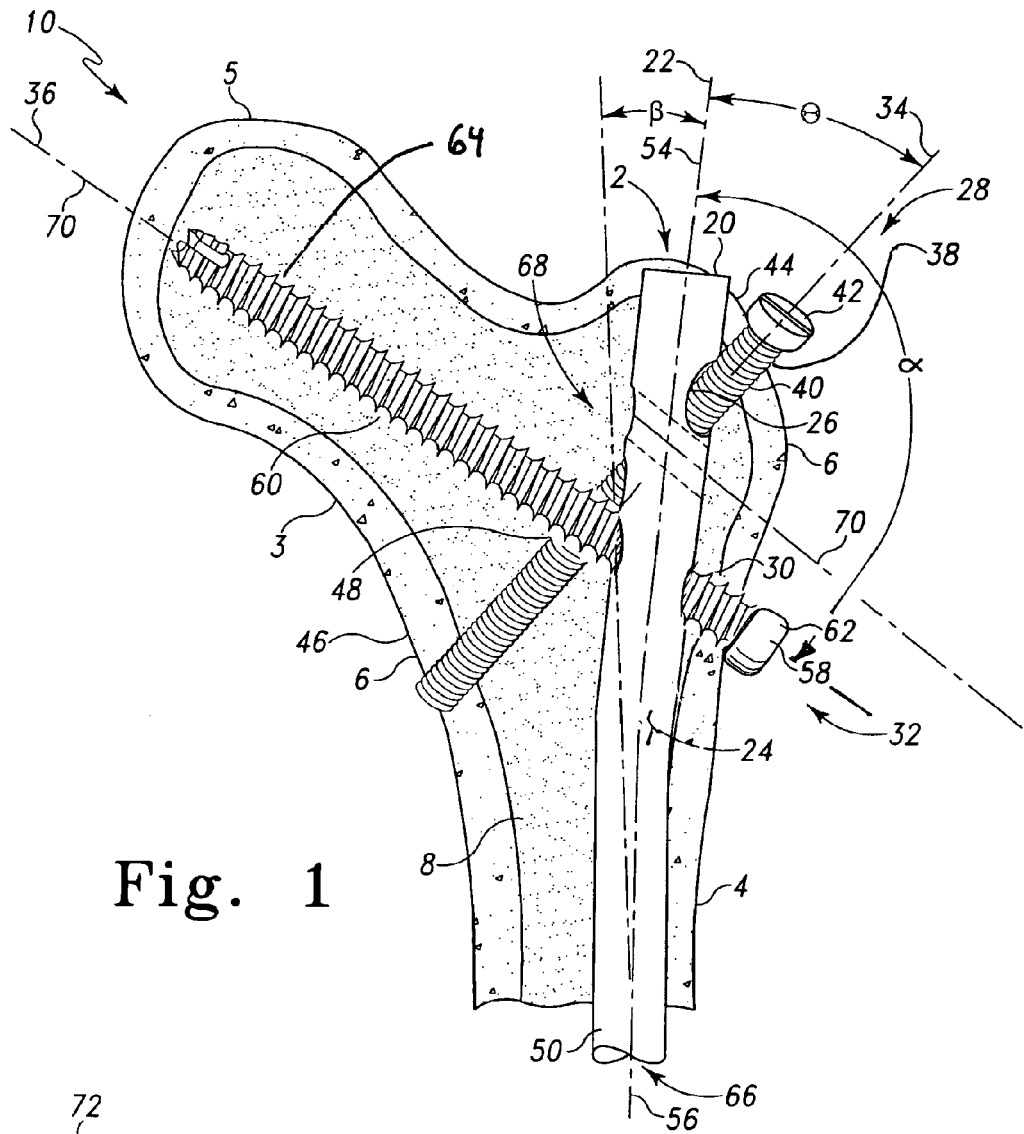
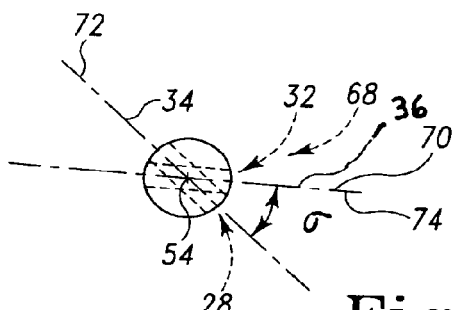
Fig. 1
Fig. 1A

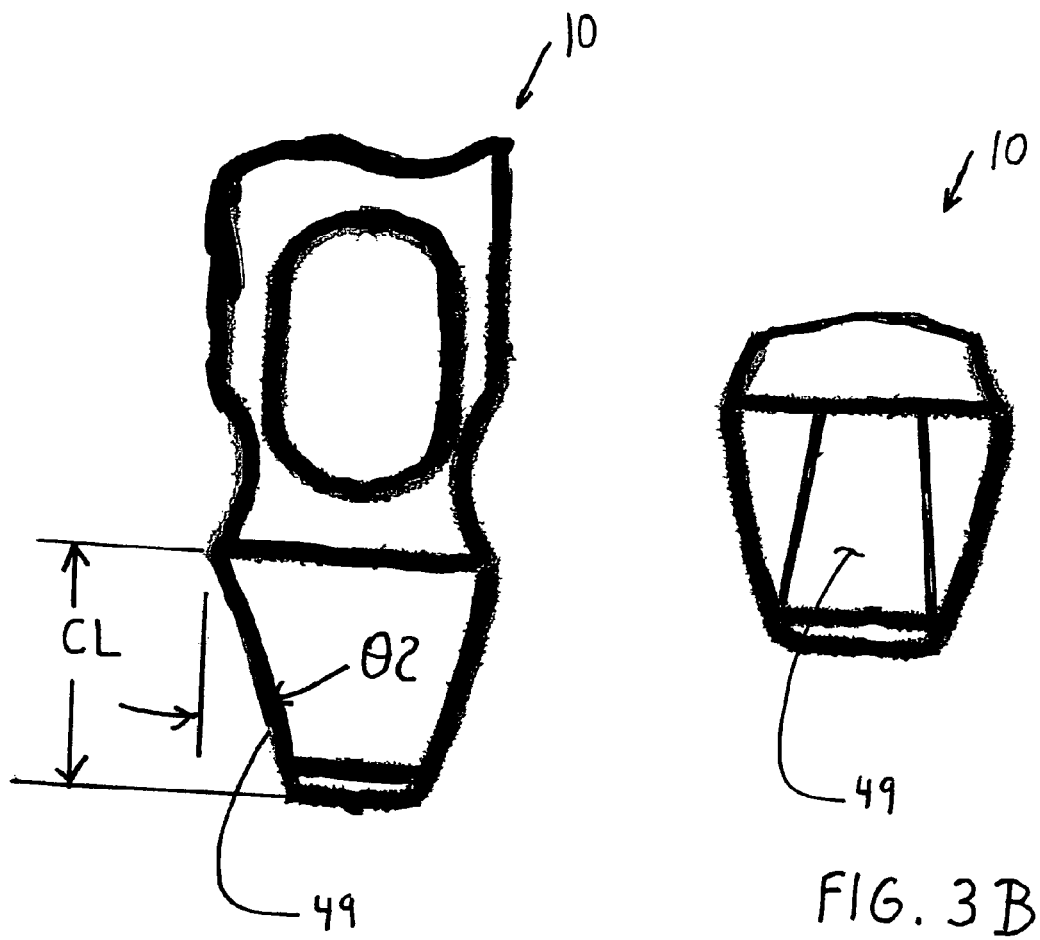

INTRAMEDULLARY NAIL WITH OBLIQUE OPENINGS

CROSS-REFERENCE TO RELATED APPLICATIONS

This is a divisional of application Ser. No. 11/262,654 filed Oct. 31, 2005 (published as U.S. 2007/0123873 and now abandoned). Cross-reference is made to the following applications: U.S. Ser. No. 11/263,465 titled "MULTIPLE PURPOSE NAIL, NAIL ASSEMBLY AND ASSOCIATED METHOD" (published as US 2007/0123876 and now abandoned), U.S. Ser. No. 11/263,199 titled "MULTIPLE PURPOSE NAIL WITH OBLIQUE OPENINGS" (published as US 2007/0123874 and now abandoned) and U.S. Ser. No. 11/263,343 titled "INTRAMEDULLARY NAIL" (published as US 2007/0123875 and now abandoned) filed concurrently herewith which are incorporated herein by reference.

TECHNICAL FIELD OF THE INVENTION

The present invention relates generally to the field of orthopaedics, and more particularly, to a device for securing a prosthetic component to bone for use with orthopaedic trauma or orthopaedic joint products.

BACKGROUND OF THE INVENTION

The skeletal system includes many long bones that extend from the human torso. These long bones include the femur, fibula, tibia, humerus, radius and ulna. These long bones particularly are exposed to trauma from accidents, and as such often are fractured during such trauma and may be subject to complex devastating fractures.

Automobile accidents, for instance, are a common cause of trauma to long bones. In particular, the femur and tibia frequently fracture when the area around the knee is subjected to a frontal automobile accident.

Often the distal end or proximal portions of the long bone, for example the femur and the tibia, are fractured into several components and must be realigned. Mechanical devices, commonly in the forms of pins, plates, screws, nails, wires and external devices are commonly used to attach fractured long bones. The pins, plates, wires, nails and screws are typically made of a durable material compatible to the human body, for example titanium, stainless steel or cobalt chromium.

Fractures of the long bone are typically secured into position by at least one of three possible techniques or methods.

The first method is the use of intramedullary nails that are positioned in the intramedullary canal of those portions of the fractured bone.

A second method of repairing fractured bones is the use of internal bone plates that are positioned under the soft tissue and on the exterior of the bone and that bridge the fractured portion of the bone.

Another method of securing fractured bones in position is the use of external fixators. These external fixators have at least two general categories. In one category, the fixator is generally linear, with a first portion of the fixator to connect to a first fracture segment of the bone and a second fracture segment of the fixator to connect to a second fracture segment of the bone. A first series of bone screws or pins are first connected to the fixator and then to the first fracture segment of the bone. Then a second series of screws or pins are connected to the fixator and then to the second fracture segment of the bone, thereby securing the first fracture segment of the bone to the second fracture segment of the bone.

A second method of external fixation is through the use of a ring type fixator that uses a series of spaced-apart rings to secure the bone. For example, an upper ring and a lower ring are spaced apart by rods. A plurality of wires is placed through the long bone and connected on each end of the long bone by the ring. The wires are then tensioned much as a spoke in a bicycle are tightened, thereby providing for a rigid structure to support the first fracture segment portion of the bone. Similarly, a plurality of wires are positioned through the second fracture segment of the bone and are secured to and tensioned by the lower ring to provide a rigid fixation of the second fracture segment of the bone bridging the fracture site.

There are a variety of devices used to treat femoral fractures. Fractures of the neck, head or intertrochanter of the femur have been successfully treated with a variety of compression screw assemblies which include a compression plate having a barrel member, a lag screw and a compressing screw. The compression plate is secured to the exterior of the femur and the barrel member is inserted into a predrilled hole in the direction of the femoral head.

The lag screw which has a threaded end and a smooth portion is inserted through the barrel member so that it extends across the break and into the femoral head. The threaded portion engages the femoral head. The compressing screw connects the lag screw to the plate. By adjusting the tension of the compressing screw the compression (reduction) of the fracture can be adjusted. The smooth portion of the lag screw must be free to slide through the barrel member to permit the adjustment of the compression screw.

Subtrochanteric and femoral shaft fractures have been treated with the help of intramedullary rods, which are inserted into the marrow canal of the femur to immobilize the femoral parts involved in fractures. A single angled cross-nail or locking screw is inserted through the femur and into the proximal end of the intramedullary rod. In some varieties, one or two screws may also be inserted through the femoral shaft and through the distal end of the intramedullary rod. These standard intramedullary rods have been successfully employed in treating fractures in lower portions of the femoral shaft.

Trochanteric nails for use in preparing femoral neck fractures utilize a screw in the form of, for example, a lag screw. The lag screws have several different problems in use that are generally related to the lag screw not remaining in the proper position with respect to the intramedullary nail during the operating life of an implant. For example, the lag screw may cut proximally through the femoral neck and head, causing the neck and head to move out of its operating position in cooperation with the acetabulum. Such a movement may render the patient non-ambulatory. Another issue that may occur with lag screws is medial migration of a lag screw through the femoral head and into the pelvic cavity. A further issue with an intramedullary nail lag screw is lateral migration or lateral pullout of the screw from the long bone.

Yet another problem with lag screws in trochanteric nail applications is the problem of neck collapse. Early after the implantation of the trochanteric nail, for example, at the first weight-bearing instance of the patient, the head of the femur may move distally due to a phenomenon known as neck collapse. If the lag screw does not capture enough cancellous bone in the femoral neck, the neck and head may move laterally causing the phenomenon known as neck collapse and creating a leg length and other issues for the patient.

Medial migration is only one of many problems that occur with a fastener for use with orthopaedic prosthetic components. The design of fasteners in cancellous and/or osteoporotic bone must deal with parameters such as pull-out forces, installation torque requirements, stripping of the bone, migration and others.

The proximal femoral fractures, for example, those around the lesser trochanter, greater trochanter, and femoral neck have been successful treated with a variety of compression screw assemblies and intramedullary rods. The intramedullary rods are inserted into the narrow canal of the femur to immobilize the femur parts involved in the fracture. Typically, a single screw is inserted through the femur and the proximal end of the intramedullary rod. Alternatively, a second screw may be inserted through the femur and into the proximal end of the intramedullary rod to prevent rotation of, for example, the neck and head of the femur.

One of the earliest intramedullary devices introduced in the United States was the Grosse-Kempf nail manufactured by Howmedica Company of Rotherudge, N.J. The Grosse-Kempf nail includes a threaded hole in the intramedullary rod for receiving an interlocking screw. The fully threaded screw cannot freely slide in order to permit the compression found in typical compression screw assemblies.

Another prior art device is in the form of Zickel™ nail (U.S. Pat. No. 3,433,220). The Zickel nail is a solid intramedullary nail having a single proximal tri-flangle cross-nail which is inserted into the direction of the femoral head. The solid cross-section does not permit the nail to be introduced over a guide rod. Thus, the nail is prevented from being used for comminuted and distal fractures of the femur because the closed surgical technique cannot be practiced. In addition, adequate compression cannot be achieved due to the requirement to lock cross-nail.

Yet another prior art device is in the form of the Russell-Taylor™ interlocking nail manufactured by Richards Medical Company of Memphis, now Smith, Nephew, and Richards. The Russell-Taylor nail similarly requires a fully threaded locking screw and therefore does not permit sliding of the screw relative to the intramedullary rod.

Yet a further prior art device is in the form of the Gamma™ nail is manufactured by Stryker-Howmedica. The Gamma nail provides for sliding compression of the lag screw through the use of a smooth shaft. The Gamma nail stops rotation of the lag screw by means of a set screw through the proximal portion of the intramedullary nail.

A further prior art device is in the form of the Ace Trochanteric™ nail manufactured by DePuy Orthopaedics, Inc. provides for means of stopping rotation of the femoral head in an unstable fracture pattern by the use of a second threaded screw in the femoral head. The lag screw is permitted to rotate freely within the nail.

In unstable femur fractures, stability is necessary to facilitate proper healing of the bone. The femur fractures may be a greater trochanteric to lesser trochanteric fracture, or a fracture of, for example, the neck of the femur. In compound fractures, the bone may be fractured at more than one fracture site. Such multiple fractures are instable and the proper healing of such fractures is difficult. Axial and rotational stability of such fractures may also be an issue. The present invention is an attempt to address at least some of the aforementioned issues.

The present invention is directed to alleviate at some of the aforementioned concerns with orthopaedic fasteners.

SUMMARY OF THE INVENTION

An embodiment of the present invention is in the form of an intramedullary nail containing a series of holes that allows for locking screws to be placed in various positions. The nail can be locked using a combination of screws, which allows various locking constructions. The nail of the present invention allows two separate screws to be placed through the nail, each screw in one of two different planes. The ability to use multiple screws in different planes allows better stability to be achieved with the locking screws.

The intramedullary nail of the present invention may be in the form of a Trochanteric Entry Nail ("TEN Nail") design allowing for multiple screw fixation to be achieved in opposing planes for better fracture stabilization. As an alternative to this design, the Trochanteric Entry Nail may be adapted for use with two screws that are located in the same plane and extend into the femoral neck. In unstable femoral fractures, stability is necessary to facilitate the proper healing and the TEN Nail design of the present invention accomplishes the improved stability. In addition to using multiple planes, the screw creates a triangular geometry that aids in better axial and rotational stability.

According to the present invention, an intramedullary nail is provided with two transverse holes for reconstruction screws and an angulated crossing hole for a trochanteric screw that goes from the greater trochanter to the lesser trochanter regions of the femur for locking screw placement. The locking screws are placed through the nail in a combination in ways that, if one reconstruction screw and the trochanteric screw are utilized, an (X) shape appears in the medial to lateral plane. When this two-screw construction is observed down the axis of the nail, the screws have an (X) appearance. The opposing nature of the screw in this nail configuration gives the added stability that is desired for this type of fracture repair. The screw configuration can be changed, so that a combination of one or two screws can be used depending on the fixation that is desired based on a particular fracture pattern.

According to one embodiment of the present invention, there is provided an intramedullary nail for use in a medullary canal of a long bone. The nail includes a body defining a longitudinal axis and an external periphery of the body for fitting in the medullary canal of the long bone. The body has a first internal wall of the body defining a first opening through the body. The first opening defines a first opening centerline. The body has a second internal wall of the body defining a second opening through the body. The second opening defines a second opening centerline. The first opening centerline and the second opening centerline are oblique with respect to each other. The first opening centerline and the longitudinal axis of the body form an acute angle between the first opening centerline and the longitudinal axis.

According to another embodiment of the present invention there is provided an intramedullary nail assembly for use in a medullary canal of a long bone. The nail assembly includes a nail defining a longitudinal axis and an external periphery of the nail for fitting in the medullary canal of the long bone. The nail has a first internal wall of the nail defining a first opening through the nail. The first opening defines a first opening centerline. The nail has a second internal wall of the nail defining a second opening through the nail. The second opening defines a second opening centerline. The first opening centerline and the second opening centerline are oblique with respect to each other. The first opening centerline and the longitudinal axis of the body form an acute angle between the first opening centerline and the longitudinal axis. The nail assembly also includes a first screw slidably fitted to the first opening and a second screw slidably fitted to the second opening.

According to yet another embodiment of the present invention there is provided a method for performing trauma surgery on a long bone. The method includes the step of providing an intramedullary nail. The nail defines a longitudinal axis and an external periphery of the nail for fitting in the medullary canal of the long bone. The nail has a first internal wall of the nail defining a first opening through the nail. The first opening defines a first opening centerline. The nail has a second internal wall of the nail defining a second opening through the nail. The second opening defines a second opening centerline. The first opening centerline and the second opening centerline are oblique with respect to each other. The first opening centerline and the longitudinal axis of the body form an acute angle between the first opening centerline and the longitudinal axis.

The method also includes the steps of positioning the nail at least partially in the medullary canal and providing a first screw for cooperation with the long bone and for sliding cooperation with the first opening in the nail. The method also includes the steps of inserting the first screw through the cortical wall of the lesser trochanter of the long bone and inserting the first screw through the first opening. The method also includes the steps of inserting said first screw through the cortical wall of the greater trochanter of the long bone and providing a second screw for cooperation with the long bone and for sliding cooperation with the second opening in the nail. The method further includes the steps of inserting the second screw through the cortical wall of the long bone, inserting the second screw through the second opening, and inserting the second screw through the cortical wall of the long bone.

According to another embodiment of the present invention there is provided an intramedullary nail for use in a medullary canal of a long bone. The nail includes a body defining a longitudinal axis of the body and an external periphery of the body for fitting in the medullary canal of the long bone. The body has a first internal wall thereof defining a first opening through the body. The first opening defines a first opening centerline.

The body has a second internal wall of the body defining a second opening through the body. The second opening defines a second opening centerline. The first opening centerline and the second opening centerline are oblique with respect to each other. The longitudinal axis of the body and the first opening centerline form an acute angle between the longitudinal axis of the body and the first opening centerline. The longitudinal axis of the body and the second opening centerline forming an acute angle between the longitudinal axis of the body and the second opening centerline.

According to yet another embodiment of the present invention there is provided a kit for use in repairing a fracture in a long bone. The kit includes a nail adapted for implantation in a medullary canal of the long bone. The nail defines a longitudinal axis and an external periphery of the nail for fitting in the medullary canal of the long bone. The nail has a first internal wall thereof defining a first opening through the nail. The first opening defines a first opening centerline. The nail has a second internal wall of the nail defining a second opening through the nail. The second opening defines a second opening centerline. The first opening centerline and the second opening centerline are oblique with respect to each other. The longitudinal axis of the body and the first opening centerline form an acute angle between the longitudinal axis of the body and the first opening centerline. The longitudinal axis of said body and the second opening centerline form an acute angle between the longitudinal axis of the body and the second opening centerline. The kit also includes a first screw adapted to be slidably fitted with the first opening and a second screw adapted to be slidably fitted with the second opening.

According to another embodiment of the present invention there is provided a method for performing trauma surgery on a long bone. The method includes the step of providing an intramedullary nail. The nail defines a longitudinal axis and an external periphery of the nail for fitting in the medullary canal of the long bone. The nail has a first internal wall of the nail defining a first opening through the nail. The first opening defines a first opening centerline.

The nail has a second internal wall, which defines a second opening through the nail. This second opening defines a second opening centerline. The first and the second opening centerlines are oblique with respect to each other. At least one of the first opening centerline and the second opening centerline are transverse to the longitudinal axis of the nail. The longitudinal axis of the body and the first opening centerline form an acute angle between the longitudinal axis of the body and the first opening centerline. The longitudinal axis of the body and the second opening centerline forming an acute angle between the longitudinal axis of the body and the second opening centerline.

The method also includes the steps of positioning the nail at least partially in the medullary canal and providing a first screw for cooperation with the long bone and for sliding cooperation with the first opening in the nail. The method also includes the steps of inserting the first screw through the cortical wall of the lesser trochanter of the long bone and inserting the first screw through the first opening.

The method also includes the steps of inserting the first screw through the cortical wall of the greater trochanter of the long bone and providing a second screw for cooperation with the long bone and for sliding cooperation with the second opening in the nail. The method also includes the steps of inserting the second screw through the cortical wall of the long bone and inserting the second screw through the second opening. The method also includes the step of inserting the second screw through the cortical wall of the long bone.

The technical advantages of the present invention include the ability to provide locking screws in various positions in an intramedullary nail. For example, according to one aspect of the present invention, an intramedullary nail for use in a medullary canal of a long bone is provided. The nail includes a body defining a longitudinal axis and an external periphery for fitting in the medullary canal of the long bone. The body defines a plurality of internal walls for defining a plurality of openings through the nail. Thus, the present invention provides for the ability to provide locking screws in various positions in that the locking screw can be placed in each of the openings.

The technical advantages of the present invention further include the ability to allow two separate screws to be placed at one time in one or two different planes. For example, and according to another aspect of the present invention, an intramedullary nail for use in the medullary canal of a long bone is provided. The nail includes a body defining a longitudinal axis and an external periphery for fitting in the canal of the long bone. The body has a first internal wall defining a first opening and a second internal wall defining a second opening. The second opening defines a second opening centerline and the first opening defines a first opening centerline. The first opening centerline and the second opening centerline are oblique with respect to each other. Thus, the present invention provides for the ability to allow two separate screws, one in each of the two openings, to be placed at one time in one or two different planes.

The technical advantages of the present invention also include the ability to allow for multiple screw fixations to be achieved in opposing planes for better fracture stabilization. For example, according to yet another aspect of the present invention, an intramedullary nail for use in the canal of a long bone is provided. The nail includes a body defining a longitudinal axis and an exterior periphery. The body has a first internal wall defining a first opening and a first opening centerline. The body also has a second internal wall defining a second opening having a second opening centerline. The first opening centerline and the second opening centerline are oblique with respect to each other. Each of the first opening and the second opening are adapted for receiving a screw. Thus the present invention provides for multiple screw fixation to be achieved in opposing planes for better fracture stabilization.

The technical advantages of the present invention also include the ability to place two screws in the same plane of the femoral neck. For example, according to yet another aspect of the present invention, an intramedullary nail is provided including a body defining a longitudinal axis and an extended periphery. The body includes a first internal wall defining a first opening and a second internal wall defining a second opening spaced from the first opening. The first opening and the second opening are parallel and spaced apart and are positioned such that the openings may be in alignment with the femoral neck of the patient. The openings may be adapted for receiving spaced apart screws that may be fitted into the neck of the femur. Thus, the present invention provides for two screws in the same plane of the femoral neck.

The technical advantages of the present invention also include the ability to place screws in multiple planes to treat unstable femoral fractures. For example, according to yet another aspect of the present invention, an intramedullary nail assembly is provided including a nail defining a longitudinal axis and an external periphery. The nail includes a first opening defining a first opening centerline and a second opening defining a second opening centerline. The first opening centerline and the second opening centerline are oblique. Each of the first opening and the second opening are adapted for receiving screws. Thus, the present invention provides for a nail in which screws may be placed in multiple planes to treat unstable femoral fractures.

The technical advantages of the present invention also include the ability to use two screws that may provide for an x-shaped geometry that aids in better axial and rotational stability. For example, according to yet another aspect of the present invention, an intramedullary nail assembly is provided, including a nail having a first opening as well as a spaced-apart second opening. The first opening and the second opening are oblique with respect to each other. The first opening and the second opening define generally an x-shape. Each of the two openings may receive a screw. Thus the present invention provides for the use of two screws to provide an x-shaped geometry that aids in better axial and rotational stability.

The technical advantages of the present invention also include the ability to permit trochanteric to greater trochanteric as well as femoral neck fixation with the same nail. For example, according to yet another aspect of the present invention, an intramedullary nail assembly is provided including a nail, that has a first opening along a first axis and a second opening along a second axis. The first and second axes are oblique and the first axis is in alignment with the greater trochanter and the lesser trochanter, while the second centerline is in alignment with the femoral neck of the femur. Each of the first and second openings are adapted for receiving screws. Thus the present invention provides for greater trochanteric to lesser trochanteric bone fixation and femoral neck fixation within the same nail.

Other technical advantages of the present invention will be readily apparent to one skilled in the art from the following figures, descriptions and claims.

BRIEF DESCRIPTION OF THE DRAWINGS

FIG. 1 is a partial anterior/posterior view of a intramedullary nail assembly in accordance with an embodiment of the present invention in the form of a left femoral trochanteric nail assembly implanted in a left femur;

FIG. 1A is an end view of the nail assembly of FIG. 1 showing the angular relationship of the screws;

FIG. 3A is an enlarged medial/lateral view of the distal tip of the nail of FIG. 3 showing the chamfer in greater detail;

FIG. 3B is an enlarged anterior/posterior view of the distal tip of the nail of FIG. 3 showing the chamfer in greater detail;

Corresponding reference characters indicate corresponding parts throughout the several views. Like reference characters tend to indicate like parts throughout the several views.

DETAILED DESCRIPTION OF THE INVENTION

Figure 1B:
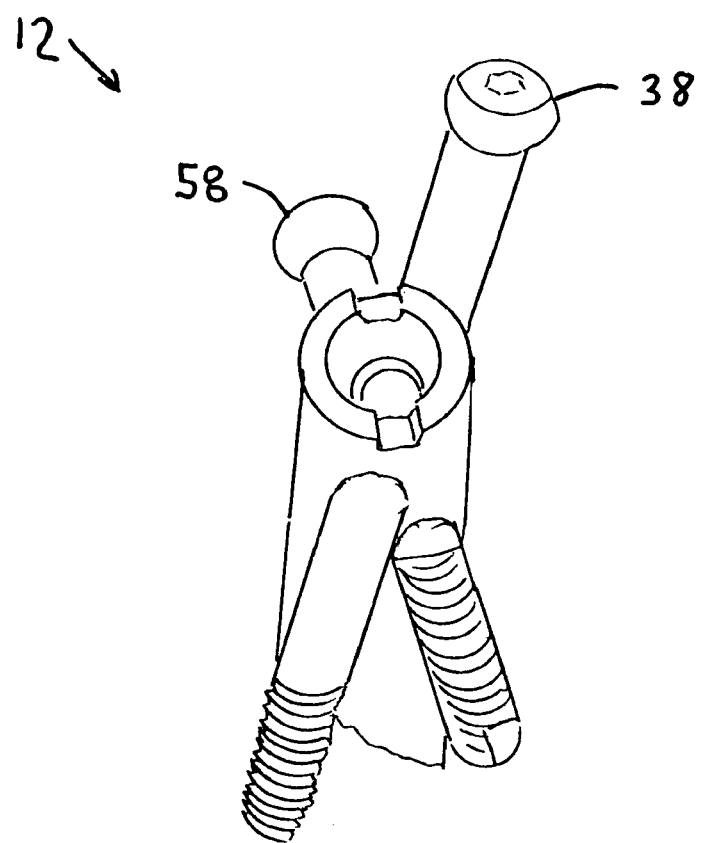
FIG. 1B is a perspective view generally from the proximal end of the nail of FIG. 1 showing the screws intersecting the nail.

Embodiments of the present invention and the advantages thereof are best understood by referring to the following descriptions and drawings, wherein like numerals are used for like and corresponding parts of the drawings.

According to the present invention and referring now to FIG. 1, a first embodiment of the present invention is shown as intramedullary nail assembly 10. Intramedullary nail assembly 10 is used in a medullary canal 2 of a long bone 4. The nail assembly 10 includes a nail 20. The nail 20 defines a longitudinal axis 22 of the nail 20. The nail 20 further includes an external periphery 24 of the nail 20. The external periphery 24 of the nail 20 is adapted for fitting in the medullary canal 2 of the long bone 4. The long bone 4 may be any long bone in the human anatomy. For example, the long bone 4 may be a femur, a tibia, a humerus, or any other long bone. Preferably, the long bone in which the nail of the present invention is used is a humerus, a femur, or a tibia, where the canal of the bone is large enough to receive a nail of the type of the present invention.

The nail 20 defines a first internal wall 26 of the nail 20. The internal wall 26 defines a first opening 28 through the nail 20. It should be appreciated that if the nail 20 is solid, the opening 28 passes obliquely through the nail 20. It should likewise be appreciated that if the nail 20 has a longitudinal opening or is cannulated, the opening 28 passes through both the external walls of the nail.

The nail 20 as shown in FIG. 1, further includes or defines a second internal wall 30 of the nail 20. The second internal wall 30 defines a second opening 32 through the wall 30 of the nail 20. The first opening 28 defines a first opening centerline 34. The second opening 32 defines a second opening centerline 36.

According to the present invention, the first opening centerline 34 and the second opening centerline 36 are oblique. The first opening centerline 34 and the second opening centerline 36, as is shown in FIG. 1, do not intersect and are not coplanar.

The nail assembly 10 of the present invention further includes a first screw 38. The first screw 38 includes a shank portion 40 that is slidably fitted to the first opening 28.

As shown in FIG. 1, the first screw 38 extends from greater trochanter 44 through cortical bone 6 into the first opening 28 into cancellous bone 8 and into cortical bone 6 and then to the lesser trochanter 46. As shown in FIG. 1, head 42 of the first screw 38 rests against the cortical bone 6 of the greater trochanter 44. The shank portion 40 of the first screw 38 engages cortical bone 6 around the lesser trochanter 46.

As shown in FIG. 1, the nail 10 includes a proximal portion 48 and a distal portion 50. As can be seen in FIG. 1, the nail 10 may, if it is straight or linear, enter the long bone or femur 4 through piriforma 52. If, however as shown in FIG. 1, the nail 20 is in the form of a bent or trochanteric nail, the nail 20 is installed or placed in the long bone 4 through the greater trochanter 44. Since the greater trochanter 44 is not in alignment with the centerline of the canal 2 of the femur 4, the proximal portion 48 of the nail 20 is bent and forms an angle β between longitudinal centerline 56 of the distal portion 50 of the nail 20 and longitudinal centerline 54 of the proximal portion 48 of the nail 20.

The first opening centerline 34 of the first opening 28 forms an angle θ between the first opening centerline 34 and longitudinal centerline 54 of the proximal portion 48 of the nail 20. The angle θ is chosen such that the first screw 38 may extend from greater trochanter 44 to lesser trochanter 46.

The nail assembly 10 of the present invention further includes a second screw 58. The second screw 58 is adapted to be fitted into the second opening 32 of the nail 20. The second screw 58, similar to the first screw 38, includes a shank 60 and a head 62. The shank 60 extends into the second opening 32. The shank 60 of the second screw 58 may include cancellous threads 64 for engaging with cancellous bone 8.

The second opening centerline 36 forms an angle α with respect to the longitudinal centerline 54 of the proximal portion 48 of the nail 20. The angle α is chosen such that the second screw 58 may extend into neck 3 and head 5 of the femur or long bone 4. The head 62 of the second screw 58 rests upon the exterior wall of the long bone 4 and the shank 60 of the second screw 58 extends through cortical 6, cancellous bone 8, the second opening 32, additional cancellous bone 8, through the neck 3, and into the head 5 of the femur or long bone 4.

The nail 20 may be solid or may include a central opening or cannula 66. Nail 20 may also include a third opening 68 formed in the nail 20. The third opening 68 may define a third opening longitudinal centerline 70. The third opening 68 may, as shown in FIG. 1, be parallel to the second opening 32. Thus, the second opening centerline 36 and the third opening centerline 70 may be parallel to each other.

The proximal portion 48 of the nail 20 may be larger in cross section than the distal portion 50 in that the proximal portion 48 of the nail 20 is adapted for positioning in the larger condylar portion of the femur 4.

As shown in FIG. 1, the nail assembly 10 is for use with a left femur. It should be appreciated that the nail 20 may be utilized with a right femur. Nail 20 includes additional bone conforming features that make the nail 20 particularly compatible with a left femur.

Referring now to FIG. 1A, the positioning of the first opening 28, the second opening 32 and the third opening 68 are shown in greater detail. The first centerline 34 of the first opening 28 defines a first plane 72. As shown in FIG. 1A, the first plane 72 is coincident with longitudinal centerline 54 of the proximal portion 48 of the nail 20. It should be appreciated that the first plane 72 may be positioned elsewhere than the longitudinal centerline of the proximal portion of the nail.

As shown in FIG. 1A, the second centerline 36 of the second opening 32 and the third centerline 70 of the third opening 68 define second plane 74. The second plane 74 is shown in FIG. 1A is coincident with longitudinal centerline 54 of the proximal portion 48 of the nail 20. The first plane 72 and the second plane 74 define an angle σ formed there between. The angle σ as shown in FIG. 1A may be an acute angle. For example, the angle σ may be from about 10 degrees to 45 degrees.

Referring again to FIG. 1, it should be appreciated that with the first screw 38 positioned in the first opening 28 and the second screw 58 positioned in the second opening 32, a generally x-shaped configuration is provided by the first screw 38 and the second screw 58. The x-shaped screw configuration of FIG. 1 provides for the strength and stability that may be desired when repairing a femoral fracture.

Referring now to FIG. 1B, the nail assembly 10 is shown with the first screw 38 and the second screw 58 intersecting the nail.

Figure 2:
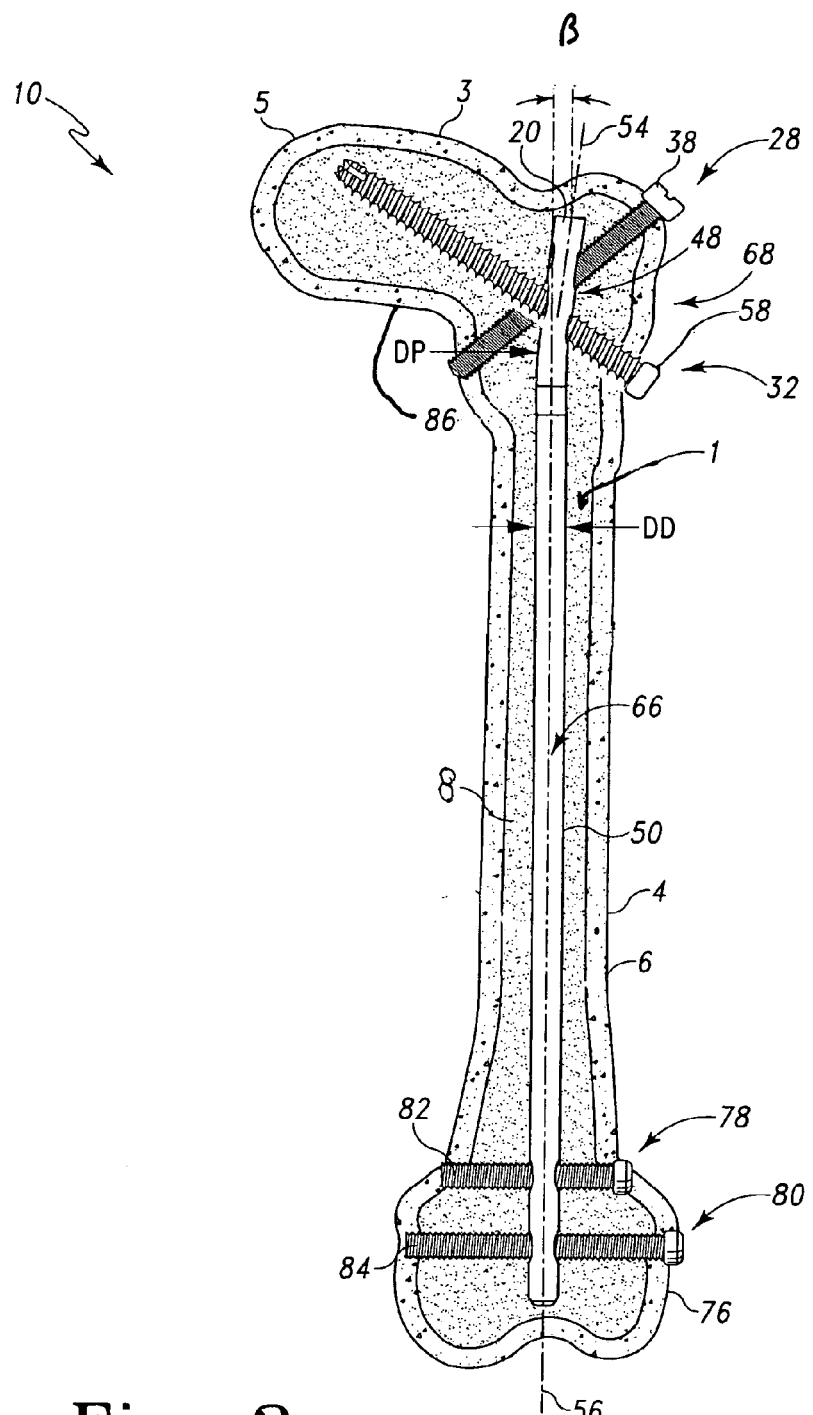
FIG. 2 is an anterior/posterior view of the intramedullary nail of the intramedullary nail assembly of FIG. 1.

Referring now to FIG. 2, the nail 20 of the present invention is shown with the full distal portion 50 shown. The distal portion 50 of the nail 20 extends into cavity 1 formed in the canal 2 of the femur 4 toward distal condyle 76 of the femur 4. The nail 20, depending on its length, may extend into the condyle 76 or may end short of the condyle 76.

The distal portion 50 may, as shown in FIG. 2, include a first distal opening 78 and, for example, a second distal opening 80 spaced from, and may as is shown in FIG. 2, be parallel to the first distal opening 78. The first distal opening 78 and the second distal opening 80 may, as shown in FIG. 2, be normal or perpendicular to centerline 56 of the distal portion of the nail 20. First distal screw 82 may be slidably fitted into the first distal opening 78 and a second distal screw 84 may be slidably fitted into the second distal opening 80. The first distal screw 82 and the second distal screw 84 may, as is shown in FIG. 2, be in the form of a cortical screw for engagement with external cortical walls of the cortical bone 6 of the femur 4.

Since proximal hip condyle 86 of the femur 4 may be larger than the shanked portion of the femur 4, the proximal portion 48 of the nail 20 may have a diameter DP, which is larger than the diameter DD of the distal portion 50 of the nail 20. The nail 20 may, as is shown in FIG. 1A, have a generally circular shape. It should be appreciated that the nail may also have other shapes. The nail 20 may be solid or may, as shown in FIGS. 1 and 2, be cannulated and be defined by the longitudinal opening or cannula 66. It should be appreciated that the nail 20 may rather than the cannula include a longitudinal groove to substitute for the cannula 66.

Figure 3:
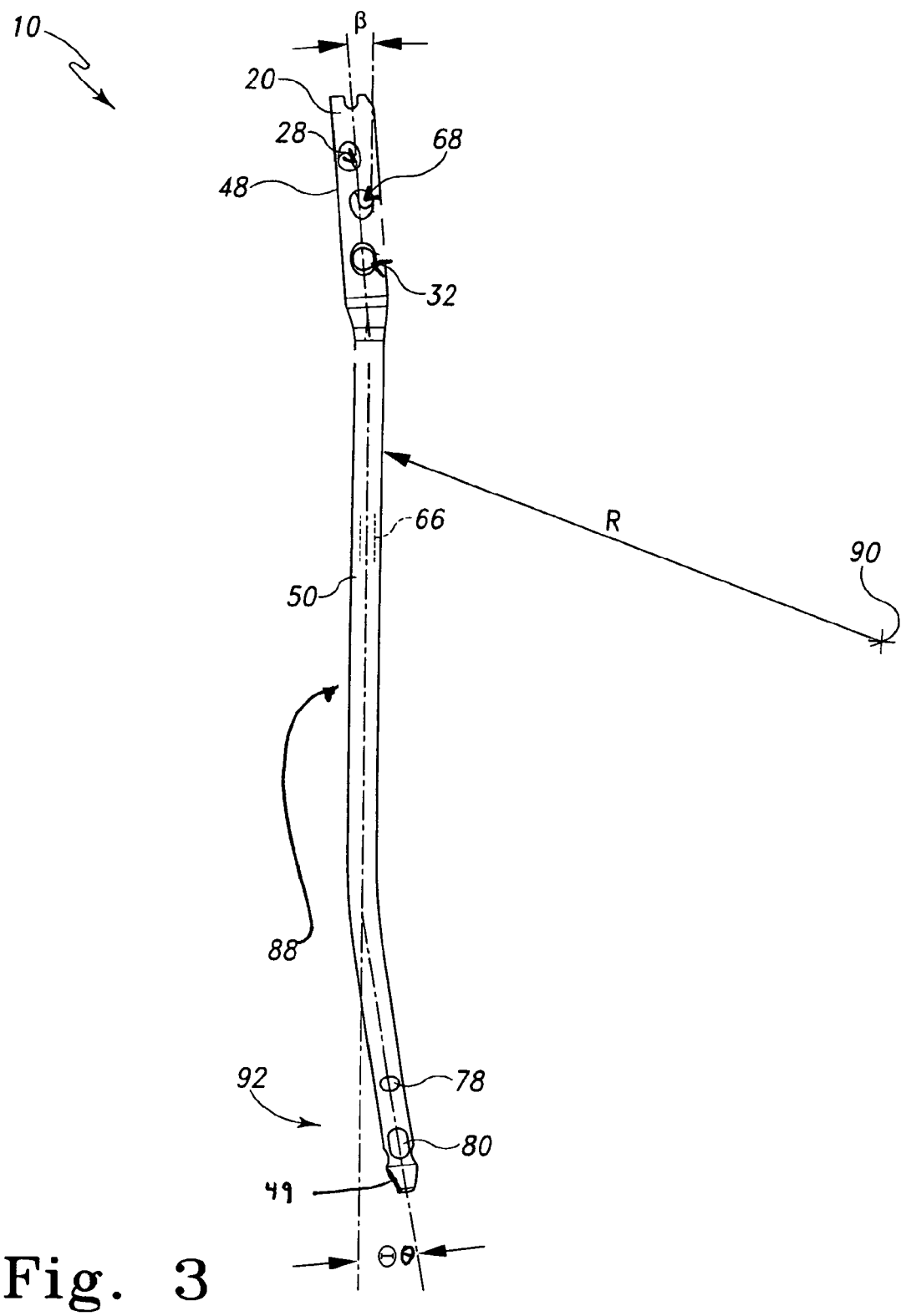
FIG. 3 is a medial/lateral view of the intramedullary nail of FIG. 2.

Referring now to FIG. 3, the nail 20 of the present invention is shown in the medial/lateral plane. In the medial/lateral plane, the nail 20 has a shape to conform to the bow in the natural femur. For example and as is shown in FIG. 3, the nail 20 includes the proximal portion 48 and the distal portion 50.

The distal portion 50 includes an arcuate portion 88 defined by radius R extending from origin 90. The distal portion 50 also includes an end portion 92 extending from the arcuate portion 88. The end portion 92 is defined by angle θ θ. The end portion 92 includes the first distal opening 78 and the second distal opening 80.

The nail 10 may, as shown in FIG. 3 include a relief surface such as a flat surface for example a chamfer 49 for assisting in leading the curved nail 10 into the medullary canal of the long bone, for example the femur. It should be appreciated that the chamfer may have a surface that is not flat, for example arcuate, for example a portion of a sphere or a cylinder.

Referring now to FIG. 3A the chamfer 49 is shown in the medial/lateral view with chamfer 49 shown on the side of the distal tip opposed to the origin 90 of the curved portion of the nail 10. The chamfer may be defined by angle θ2 from the longitudinal periphery of the nail 10. The chamfer may be further defined by chamfer length CL from the distal end of the nail 10.

Referring now to FIG. 3B the chamfer 49 is shown in the anterior/posterior view with chamfer 49 shown at distal tip. It should be appreciated that the tip may be larger or smaller than shown.

Figure 4:
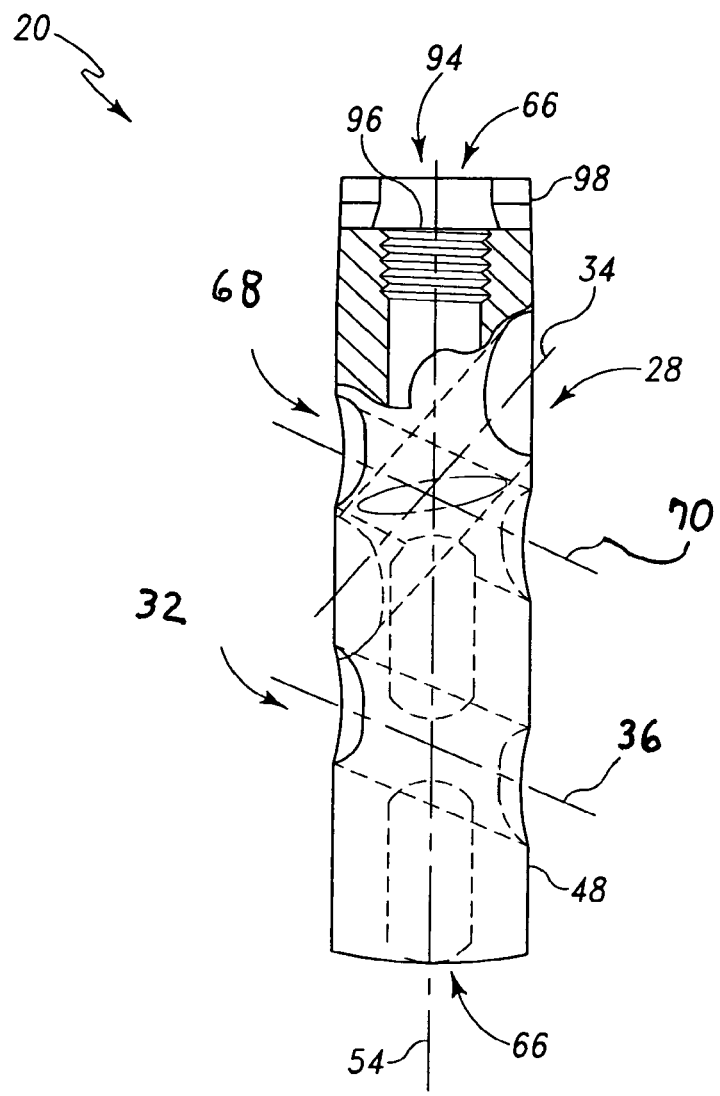
FIG. 4 is an enlarged partial anterior/posterior view partially in cross section of the proximal end of the intramedullary nail assembly of the intramedullary nail of FIG. 2.

Referring now to FIG. 4, the proximal portion 48 of the nail 20 is shown in greater detail. The proximal portion 48 includes the first opening 28, which defines first opening centerline 34. The proximal portion 48 also includes second opening 32 defining second opening centerline 36. The proximal portion 48 also includes the third opening 68 defining third opening centerline 70. The nail 20 further defines a counter bore 94 extending from the proximal end of the proximal portion 48. As shown in FIG. 4, the counter bore 94 is generally concentric with the longitudinal opening 66 of the nail. The counter bore 94 defines internal threads 96 for cooperation with a fastener to lock the screws.

The nail 20 further includes a transverse slot 98 which may be helpful for guiding the nail 20 during installation.

Figure 5:
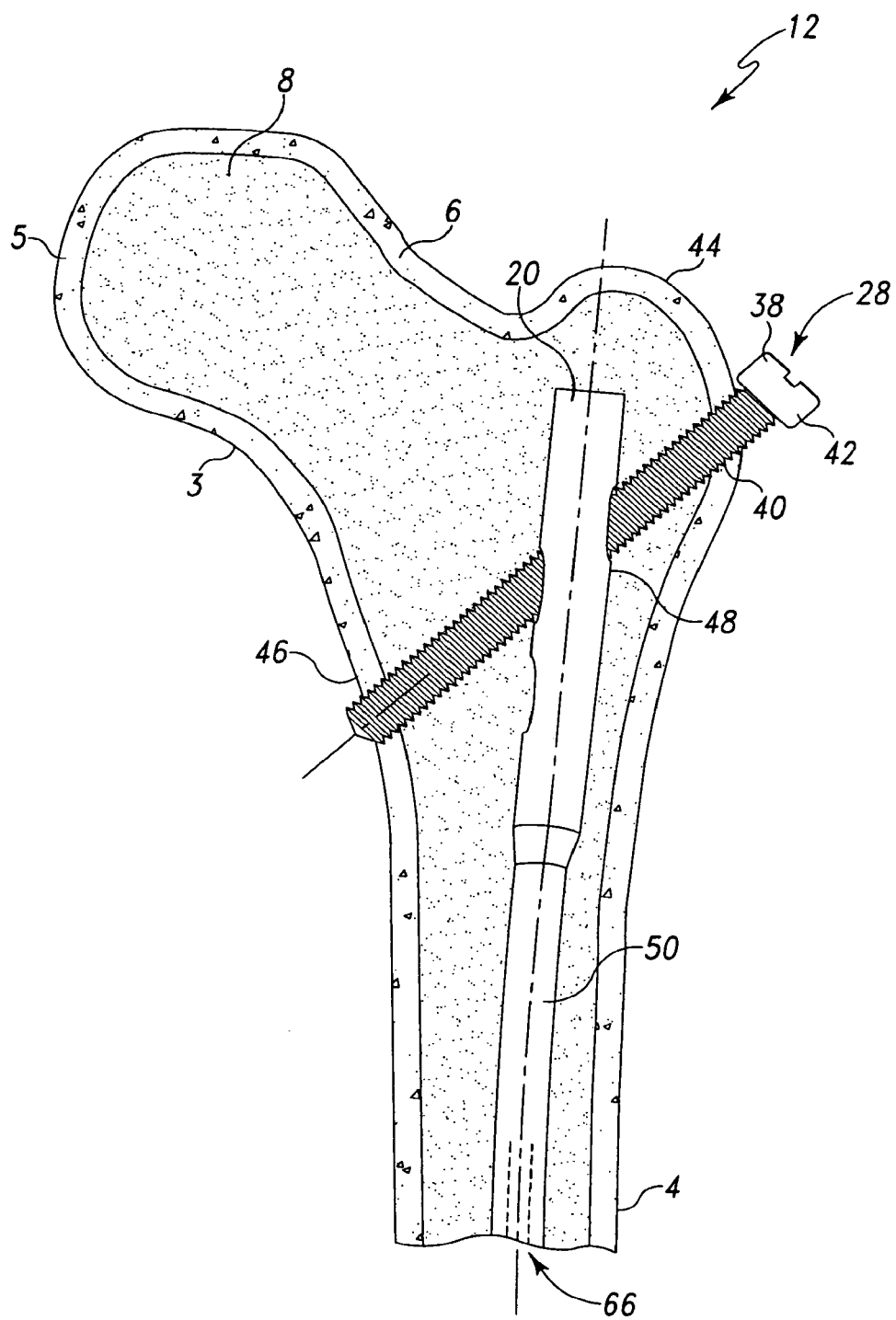
FIG. 5 is an enlarged partial anterior/posterior view of the proximal end of the intramedullary nail assembly of FIG. 1 implanted in a left femur with only the greater trochanter/lesser trochanter screw in use.

Referring now to FIG. 5, second assembly 12 of a nail assembly in accordance with the present invention is shown. The second nail assembly 12 is for use in securing the greater trochanter 44 to the lesser trochanter 46. The second assembly 12 includes the nail 20 of FIGS. 1 through 4 and the first screw 38. The first screw 38 is placed in first opening 28 and the head 42 of the first screw 38 is advanced until it seats against cortical bone 6 of the femur 4. The shank 40 of the screw 38 extends into the cancellous bone 8, through the first opening 28 and through additional cancellous bone 8. The shank 40 also engages cortical bone 6 to secure the screw 38 to the femur 4.

Figure 6:
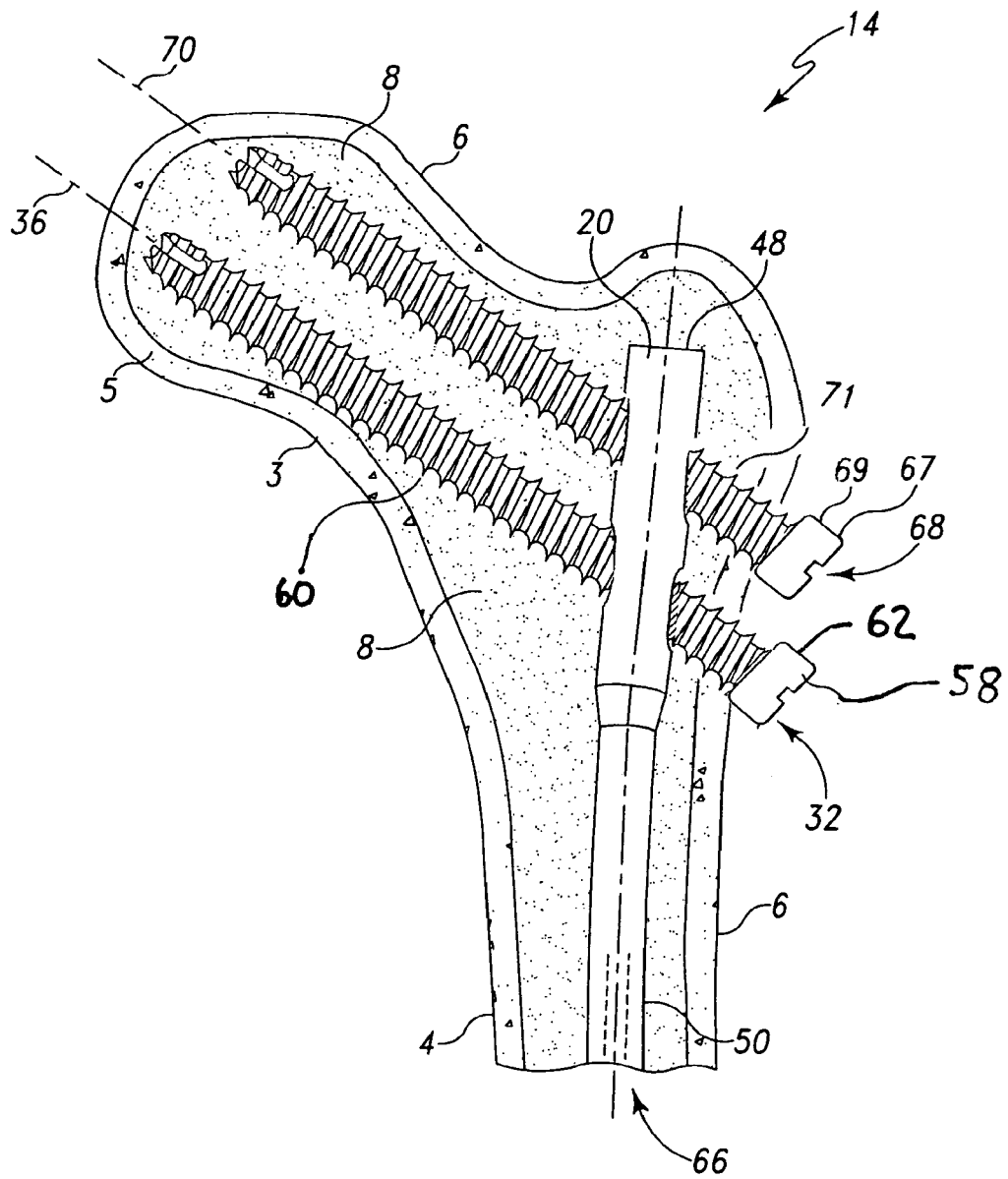
FIG. 6 is an enlarged partial anterior/posterior view of the proximal end of the intramedullary nail assembly of FIG. 1 implanted in a left femur with two fully threaded femoral neck screws in use.

Referring now to FIG. 6, yet another aspect of the present invention is shown as third nail assembly 14. The third nail assembly 14 is for use to engage the neck 3 and the head 5 of the femur or long bone 4. The nail assembly 14, as shown in FIG. 6, includes the nail 20 as well as second screw 58. The second screw 58 is slidably fitted in second opening 32 of the nail 20. The second screw 58 is placed into the second opening 32 with head 62 of the second screw 58 positioned against cortical bone 6 and shank 60 of the second screw 58 extending through the cortical bone 6 into cancellous bone 8. The second screw 58 further extends through the opening 32 and into the cancellous bone 8. The second screw 58 extends through the neck 3 and may extend into the head 5 within the cancellous bone 8.

While the nail assembly 14 may be operable with a solitary screw, for example, second screw 58, the third assembly 14 may also include an additional screw in the form of third screw 67. The third screw 67 is utilized in the third assembly 14 to provide fixation of the neck 3 and the head 5. The third screw 67 is slidably fitted into the third opening 68 of the nail 20. The third screw 67 includes a head 69 and a shaft or shank 71. The head 69 of the screw 67 rests against the outer surface of the cortical bone 6 of the femur 4. The shank 71 extends through cortical bone 6, cancellous bone 8, the third opening 67, and into the cancellous bone 8. The third screw 67 extends into the cancellous bone 8 of the neck 3 and into the cancellous bone 8 of the head 5. As shown in FIG. 6, the third screw 67 when assembled into the third opening 68 may extend along third centerline 70, which is parallel and spaced from second opening centerline 36.

While the second screw 58 and the third screw 67 may be fully threaded, as is shown in FIG. 6, it should be appreciated that the second screw 58 and the third screw 67 may be partially threaded.

Figure 7:
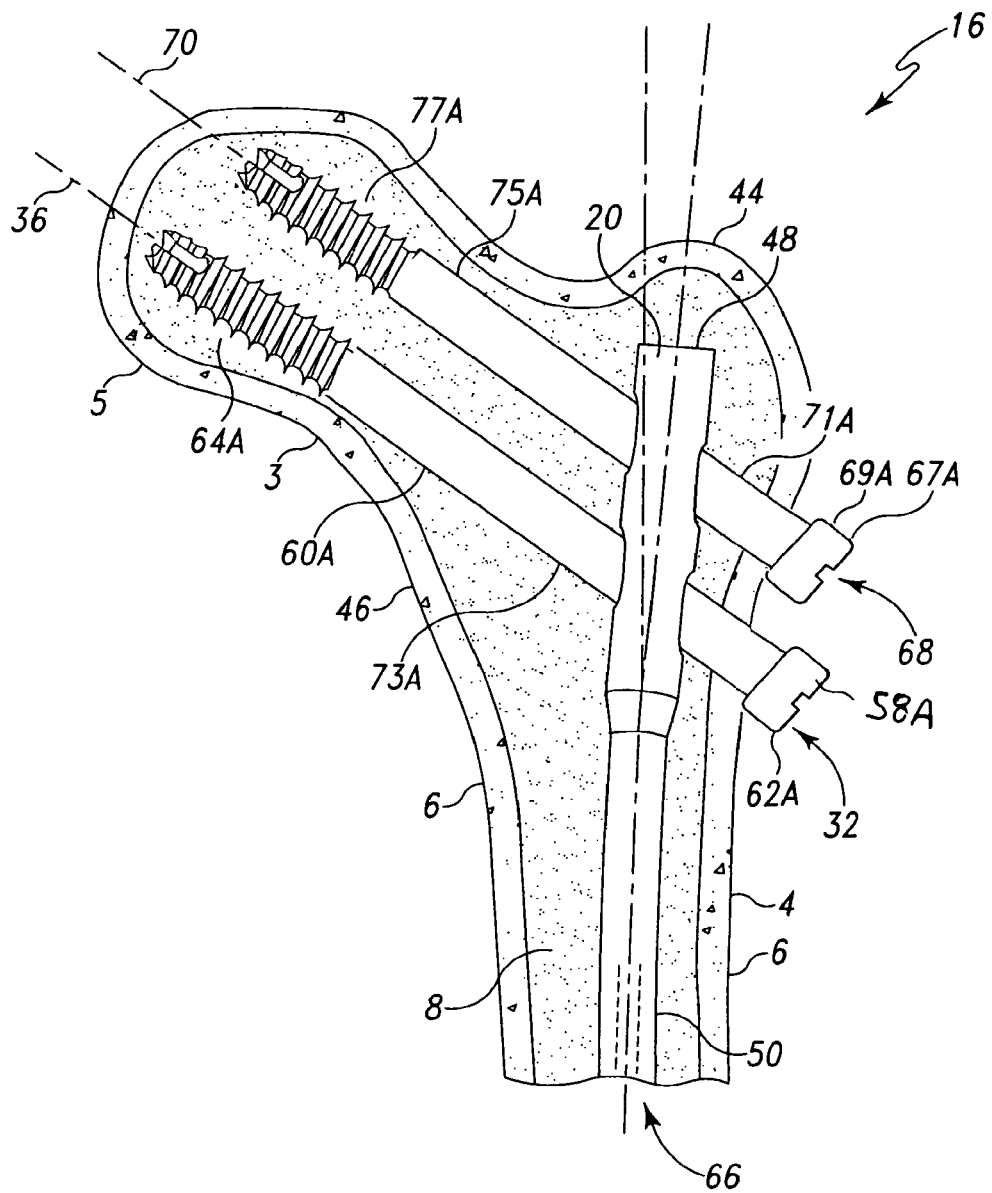
FIG. 7 is an enlarged partial anterior/posterior view of the proximal end of the intramedullary nail assembly of FIG. 1 implanted in a left femur with two partially threaded femoral neck screws in use.

For example, and referring now to FIG. 7, yet another form of the present invention is shown as fourth nail assembly 16. The fourth nail assembly 16 is in the form of a nail assembly with screws that are only partially threaded. The use of partially threaded may permit the sliding compression or motion of the head and neck in a downward fashion to facilitate healing.

The fourth nail assembly 16 of FIG. 7 includes the nail 20 of FIGS. 1 through 5 as well as second partially threaded screw 58A similar to the screw 58 of FIG. 6. The second screw 58A, as shown in FIG. 7, is, however, only partially threaded in shank 60A of the second screw 58A.

Similarly, the fourth nail assembly 16 includes a third screw 67A similar to the third screw 67 of FIG. 6. The third screw 67A has a shank 71A that is, however, only partially threaded.

As shown in FIG. 7, the second screw 58A includes a head 62A, which rests against cortical bone 6 of the femur 4. The shank 60A of the second screw 58A includes a smooth portion 73A of the shank 60A, which is positioned between the head 62A and threads 64A of the screw 58A. The smooth portion 73A of the second screw 58A extends from the head 62A, through the cortical bone 6, through cancellous bone 8, through the second opening 32 of the nail 20, through cancellous bone and to the threads 64A of the shank 60A.

Similarly, the third screw 67A includes a smooth portion 75A of the shank 71A, which extends from head 69A to threads 77A of the shank 71A. The third screw 67A when installed in the nail 20 is installed such that head 69A of the third screw 67A rests against the outer wall of the cortical bone 6 of the femur 4. The smooth portion 75A of the shank 71A extends through cortical bone 6, through cancellous bone 8, through the third opening 68, and into the cancellous bone 8. The threads 77A extend from the smooth portion 75A of the shank 71A. It should be appreciated that the smooth portion 73A of the second screw 58A and the smooth portion 75A of the third screw 67A extend through the respective second opening 32 and third opening 68 of the nail 20, such that sliding compression of the fractured hip joint may be provided.

Figure 8:
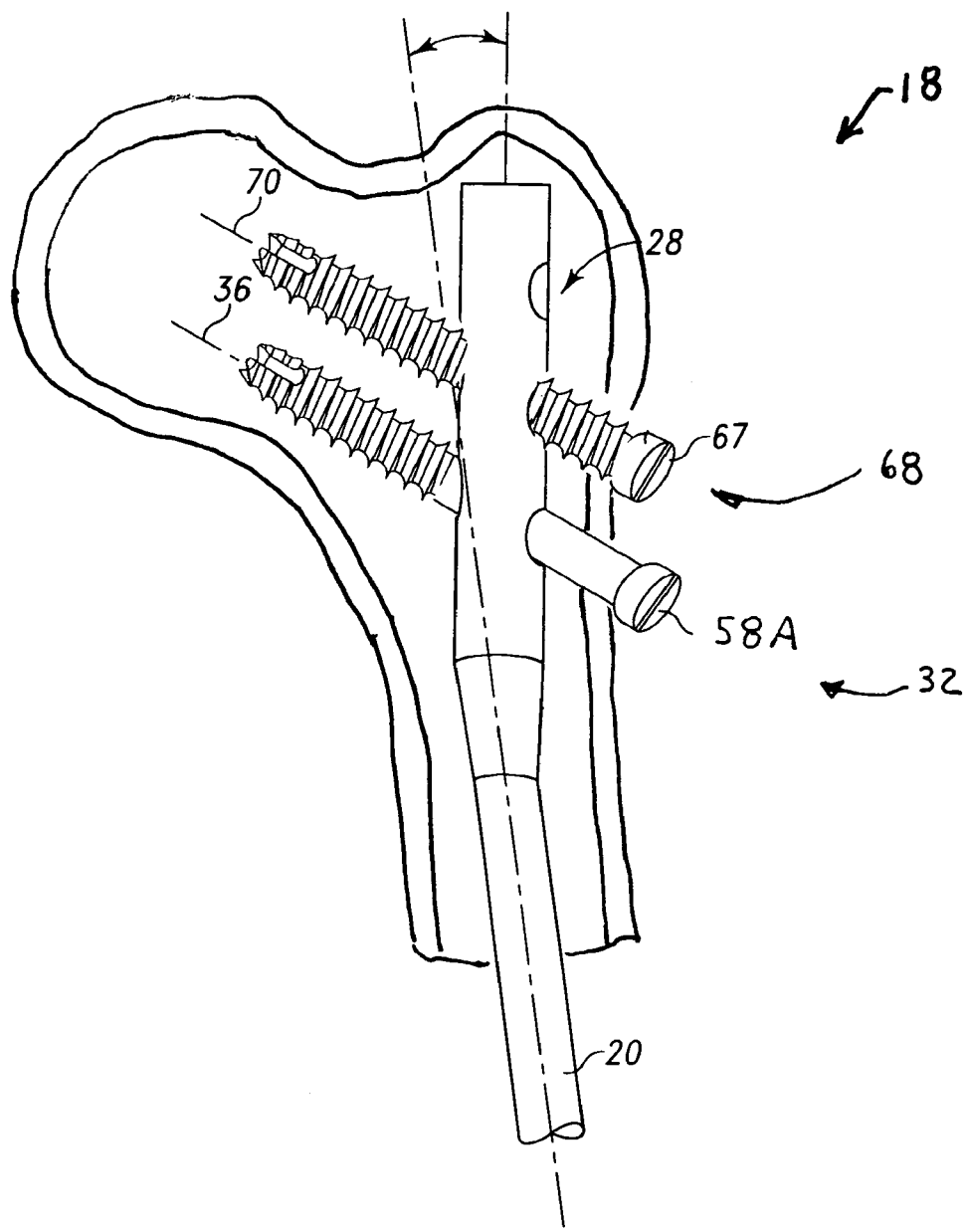
FIG. 8 is an enlarged partial anterior/posterior view of the proximal end of the intramedullary nail of FIG. 1 implanted in a left femur with a fully threaded femoral neck screws and a partially threaded femoral neck screws in use.

Referring now to FIG. 8, yet another form of the present invention is shown as fifth nail assembly 18. The fifth nail assembly 18, as shown in FIG. 8, includes both a fully threaded screw and a partially threaded screw.

Referring now to FIG. 8, yet another form of the present invention is shown as fifth nail assembly 18. The fifth nail assembly 18 utilizes both a partially thread and a fully threaded screw. The fifth assembly 18 as shown in FIG. 8, includes the nail 20 as well as second screw 58A and third screw 67. The second screw 58A is fitted into second opening 32 and the third screw 67 is fitted into third opening 68.

The nail 20 may be made of any suitable durable material and may, for example, be made of a plastic, a metal or a carbon fiber composite material. To obtain the strength necessary, the nail 20 is preferably made of a metal. If made of a metal, the nail 20 may be made of a metal that is compatible with the human anatomy and is sterilizable. Such materials include cobalt chromium alloy, a stainless steel alloy, and a titanium alloy.

Figure 9:
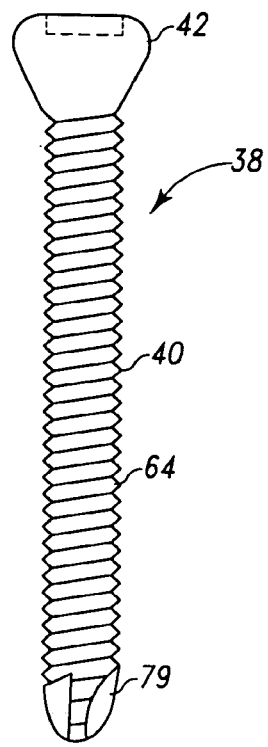
FIG. 9 is a plan view of a cortical screw for use in the nail assembly of FIG. 1.

Referring now to FIG. 9, the first screw 38, as is shown in greater detail. The first screw 38 as shown in FIG. 9, is in the form of a cortical screw for securing the screw to cortical bone. The first screw 38 includes the head 42 and the shank 40. The shank 40 includes threads 64 for engagement with bone. The screw 38 as shown in FIG. 9, may include a self-tapping feature 79 for tapping or preparing the threads in the bone to receive cortical threads 11 of the screw 38. It should be appreciated that the self-tapping feature 79 may also include a self-drilling feature similar to and provide the opening in the bone for preparing the bone for receiving the threads 64.

Figure 9A:
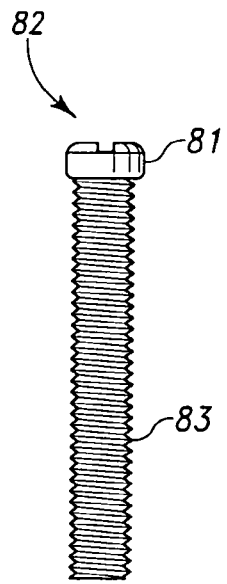
FIG. 9A is a plan view of a first distal cortical screw for use in the nail assembly of FIG. 1.

Referring now to FIG. 9A, the first distal screw 82 is shown in greater detail. The first distal screw 82 includes a head 81 and a threaded shank 83. The shank 83 may be threaded with cortical screw threads for engagement with cortical bone. The shank 83 may also include a self-tapping feature similar to the self-tapping feature 79 of the screw 38 of FIG. 9.

Figure 9B:
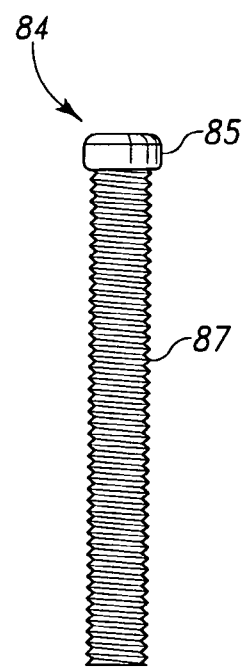
FIG. 9B is a plan view of a second distal cortical screw for use in the nail assembly of FIG. 1.

Referring now to FIG. 9B, the second distal screw 84 is shown in greater detail. The second distal screw 84 includes a head 85 as well as a shank 87. Shank 87 may include cortical threads and may include a self-tapping feature similar to the self-tapping feature 79 of the screw 38 of FIG. 9.

The cortical screws 38, 82 and 84 may be made of any suitable durable material and may, for example, be made of a plastic, a metal or a carbon fiber composite material. To obtain the strength necessary, the screws are preferably made of a metal. If made of a metal, the screws may be made of a metal that is compatible with the human anatomy and is sterilizable. Such materials include cobalt chromium alloy, a stainless steel alloy, and a titanium alloy.

Figures 10, 10A:
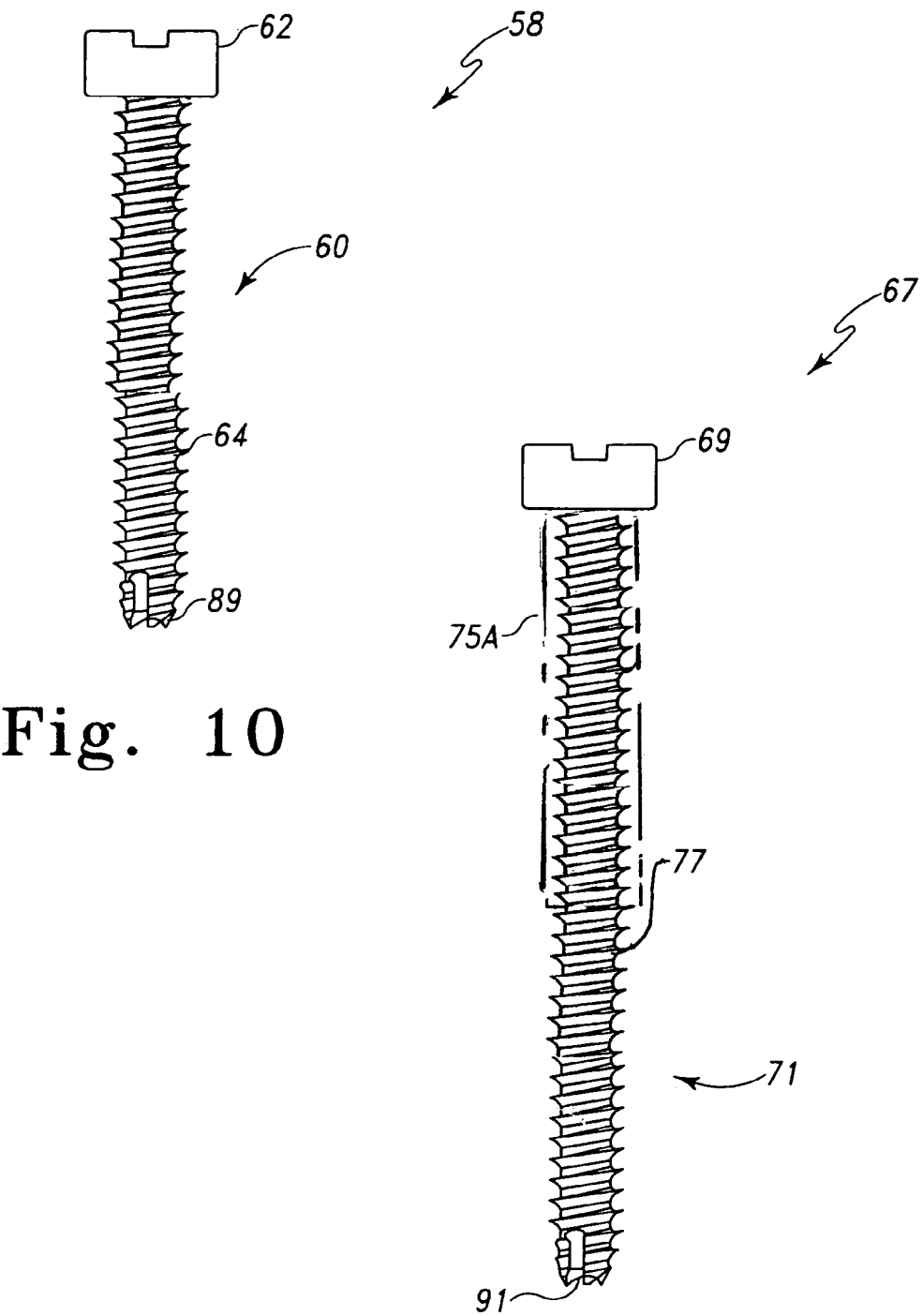
FIG. 10 is a plan view of a first cancellous screw for use in the nail assembly of FIG. 1.
FIG. 10A is a plan view of a second cancellous screw for use in the nail assembly of FIG. 1.

Referring now to FIG. 10, cancellous screws for use with the intramedullary nail of the present invention are shown. For example as shown in FIG. 10, second screw 58 includes head 62 as well as shank 60 extending from the head 62. The shank 60 includes threads 64 that may be positioned on the entire shank 60 or, alternatively, be provided only on a portion of the shank 60. The second screw 58 may include a self-drilling and self-tapping feature 89 located on the end of the threads 64 to provide for self-drilling and self-tapping of the thread 64 through cancellous bone.

Now referring to FIG. 10A, the third screw 67 is shown. The third screw 67 may likewise be a cancellous screw and include a head 69 as well as a shank 71. The shank 71 may include threads 77, which are positioned on the entire shank 71 of the third screw 67. The third screw 67 may further include a self-tapping and self-drilling feature 91 similar to the self-tapping and self-drilling feature 89 of the second screw 58. The third screw 67 may alternately include a shank 71, which is not fully threaded. For example and as shown in FIG. 10 in phantom, unthreaded shank portion 75A may be included in alternate screw 67A.

Figure 11:
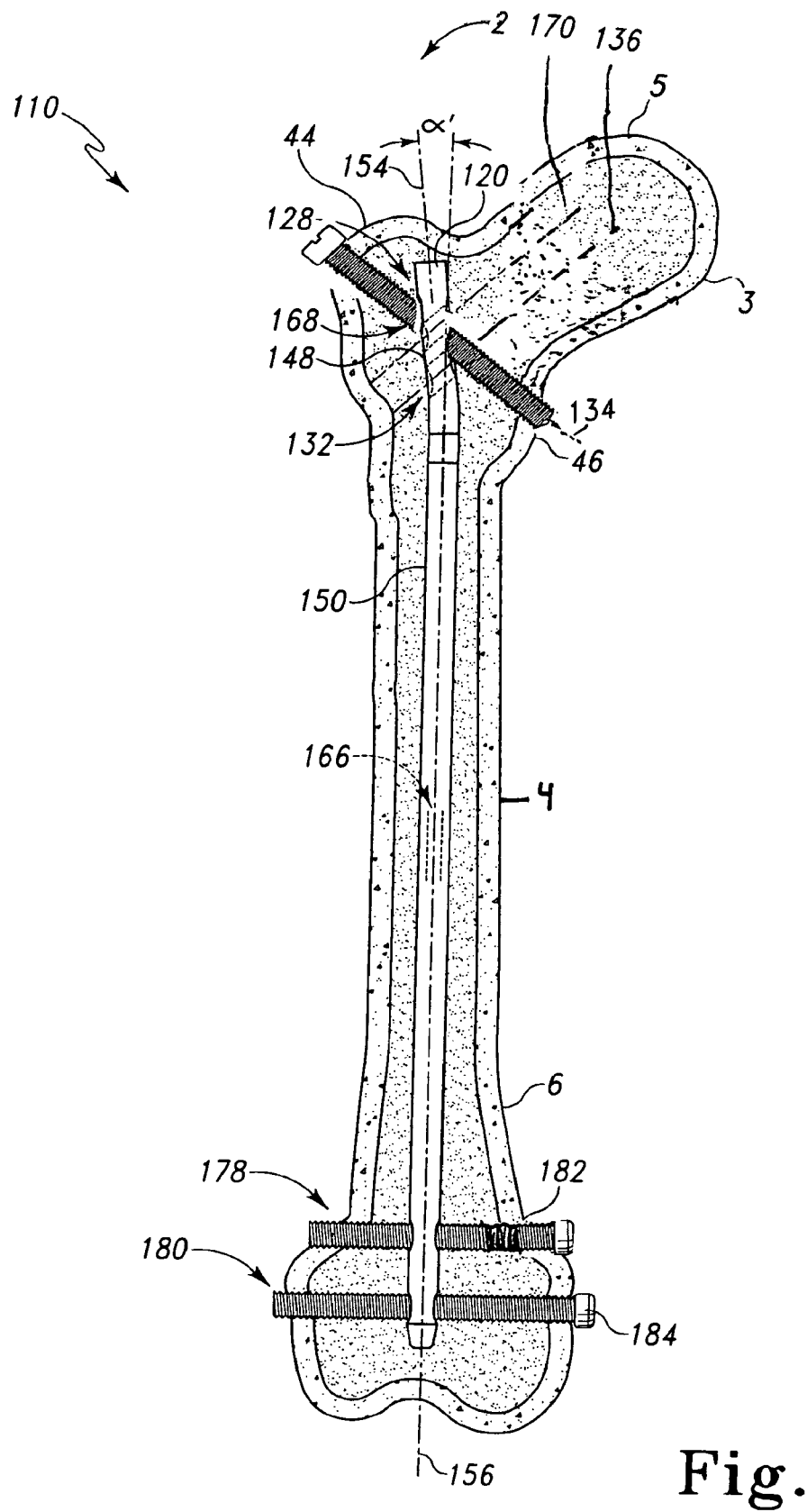
FIG. 11 is an anterior/posterior view of an intramedullary nail in accordance with an embodiment of the present invention in the form of a right femoral trochanteric nail implanted in a right femur.

According to the present invention and referring now to FIG. 11, yet another embodiment of the present invention is shown as intramedullary nail assembly 110. The intramedullary nail assembly 110 as shown in FIG. 11, is for use with right femur 4. The intramedullary nail assembly 110 of FIG. 11 is a mirror image of the nail assembly 10 of FIGS. 1 and 2.

The intramedullary nail assembly 110 includes a nail 120 that is a mirror image of the nail 20 of FIGS. 1 and 2.

The intramedullary nail 120 may have any suitable shape to fit within canal 2 of femur 4. To fit within the canal 2, the nail 120 may be longitudinally elongated. For simplicity and to fit into the canal 2, the nail 120 may have a generally circular cross section. The nail 120 may be linear or straight or may be curved and bent to more closely conform to the shape of the canal 2. The nail 120 may be solid or, as is shown in FIG. 11, be cannulated or include a central opening 166 extending along the length of the nail 120.

The nail 120 as shown in FIG. 11, may include a proximal portion 148 as well as a distal portion 150 extending from the proximal portion 148. The proximal portion 148 defines a proximal portion centerline 154, while the distal portion 150 defines a distal portion centerline 156. The proximal portion centerline 154 forms an angle α' with respect to the distal portion centerline 156. Such an angular relationship between the proximal portion 148 and the distal portion 150 facilitates the nail 120 to be installed through greater trochanter 44 of the femur 4.

The assembly 110 may include screws, for example first screw 138, for use with the nail 120. The screws may be used to connect greater trochanter 44 with the lesser trochanter 46 or alternatively, or in combination, the nail assembly 110 may also include screws (described later) for engagement with neck 3 and head 5 of the femur 4. The nail 120, as is shown in FIG. 11, may, thus, include a first opening 128 defining a first opening centerline 134. The first opening 128 is adapted for receiving a screw for connecting the greater trochanter 44 to the lesser trochanter 46.

The nail 120 may further include a second opening 132 defining a second opening centerline 136. The second opening 132 may be adapted for receiving a screw for engagement with neck 3 and head 5 of the femur 4. The nail 120 may further include a third opening 168 defining a third opening centerline 170. The third opening 168 may be adapted for receiving a third screw. The third opening 168, as shown in FIG. 11, may be parallel to the second opening 132. The screw for the third opening 168 may be positioned in the neck 3, as well as, in the head 5 of the femur 4.

The nail assembly 110 may further include distal screws for distally securing the nail 120 to the femur 4. For example and as shown in FIG. 11, the nail 120 may include a first distal opening 178 for receiving a first distal screw 182. The first distal screw 182, as shown in FIG. 11, may be normal or perpendicular to distal portion centerline 156. The nail 120 may further include a second distal opening 180 spaced from and parallel to the first distal opening 178. The nail assembly 110 may further include a second distal screw 184 for cooperation in the second distal opening 180 of the nail 120. The first distal screw 182 and the second distal screw 184 may be in the form of cortical screws that may cooperate with cortical bone 6 of the femur 4.

Figures 12, 12A:
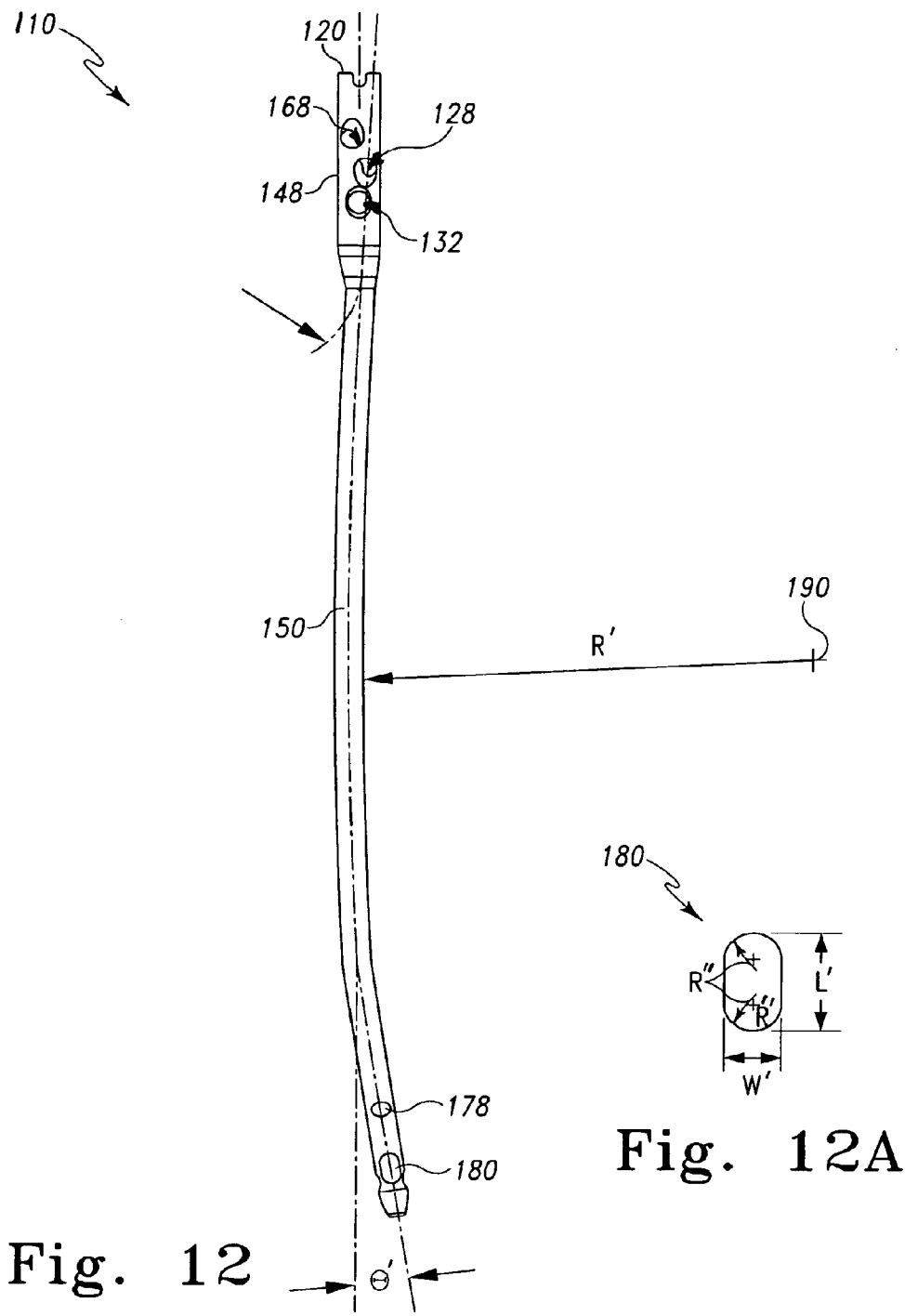
FIG. 12 is a medial/lateral view of the intramedullary nail of FIG. 11.
FIG. 12A is a partial medial/lateral view of the elongated slot of the intramedullary nail of FIG. 12.

Referring now to FIG. 12, the medial/lateral view of the nail 120 is shown. The proximal portion 148 of the nail 120 includes the first opening 128, the second opening 132 and the third opening 168. The proximal portion 148 may be, as is shown in FIG. 12, larger in diameter than the distal portion 150, so that the screw openings may be accommodated in the proximal portion 148.

The distal portion 150 as shown in FIG. 12, may have a shape conforming to a right femur. For example and as is shown in FIG. 12, the distal portion 120 may be arcuate and may be defined by a radius R' extending from origin 190. The arcuate shape of the distal portion 150 corresponds to the arcuate shape of the right femur medullary canal, in which the nail 120 is positioned.

As shown in FIG. 12, the distal portion 150 of the nail 120 may include a distal portion which may not be arcuate, but may extend at an angle θ' from the distal portion 150. The distal part of the distal portion 150 may include the distal openings. For example, the distal portion 150 may include a first distal opening 178, which may, as is shown in FIG. 12, be generally cylindrical in shape as well as a second distal opening 180.

Referring now to FIG. 12A, the second distal opening 180 may be generally oval. For example and as shown in FIG. 12, the second distal opening 180 may be defined by a overall length L' and a width W'. The second distal opening 120 may further be defined by radii R", located on both ends of the second distal opening 180.

Figure 13:
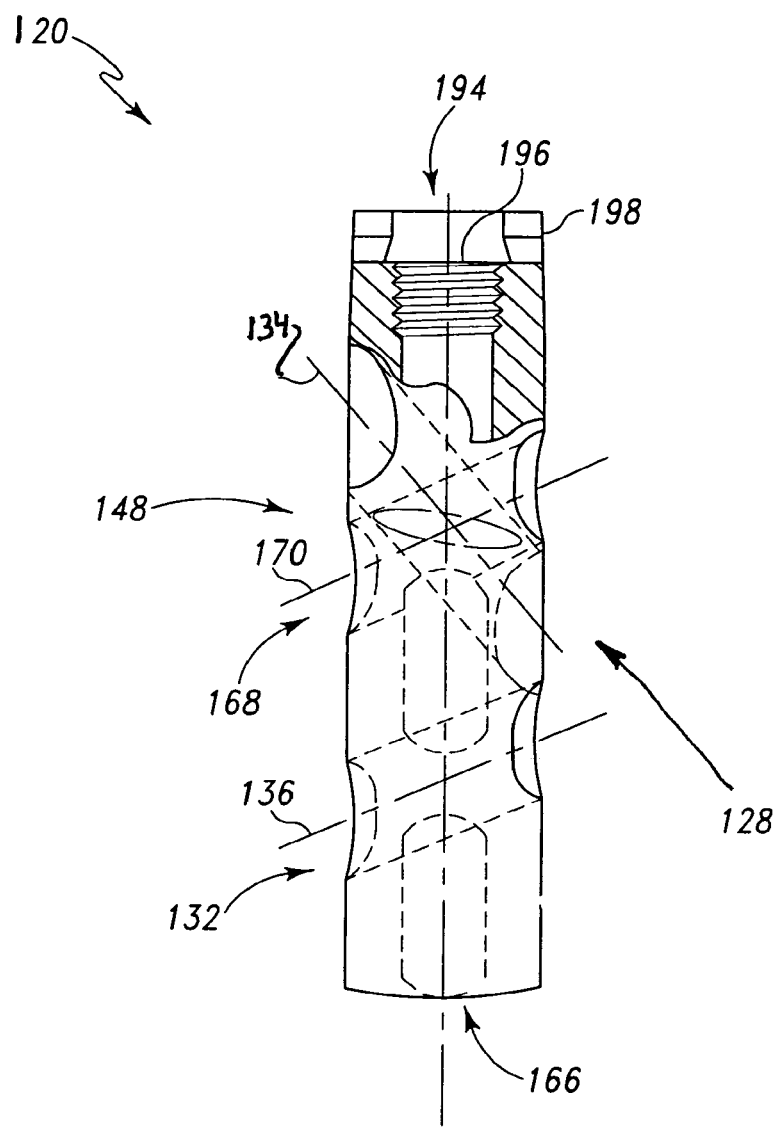
FIG. 13 is a partial anterior/posterior view of the intramedullary nail of FIG. 11.

Referring now to FIG. 13, the proximal portion 148 of the nail 120 is shown in greater detail. The nail 120 may include the longitudinal opening 166, as well as first opening 128 defining first opening centerline 134. The proximal portion 148 may further define the second opening 132 defining the second opening centerline 136. The proximal portion 148 may further define the third opening 168 defining third opening centerline 170.

To lock at least one of the screws with respect to the nail 120, the nail 120 may include a feature for locking the screw to the nail. For example, the nail 120 may include a counter bore 194 onto which internal threads 196 are formed. The internal threads 196 may be adapted for fitting to a fastener used to contact the screw to lock the screw to the nail 120. The nail 120 may further include a slot 198 to angularly position the nail 120.

Figure 14:
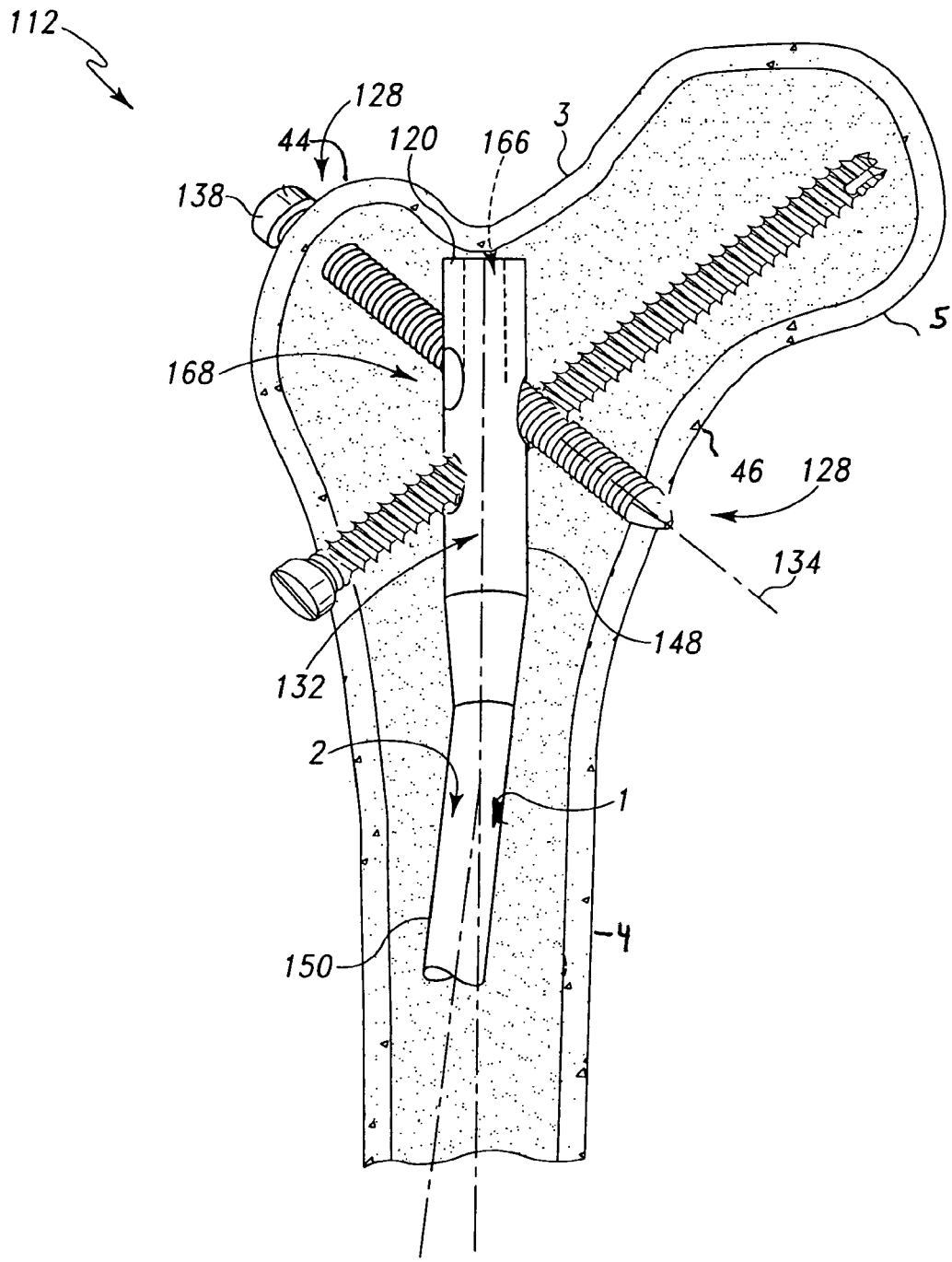
FIG. 14 is an enlarged partial anterior/posterior view of the proximal end of the intramedullary nail of FIG. 11 implanted in a right femur with only a greater trochanter/lesser trochanter screw in use to form a nail assembly according to the present invention.

Referring now to FIG. 14, another embodiment of the present invention is shown as intramedullary nail assembly 112. The intramedullary nail assembly 112 includes the nail 120 of FIGS. 11 through 13. The nail assembly 112 of FIG. 14 is adapted for connection of the greater trochanter 44 with the lesser trochanter 46. The nail assembly 112 includes first screw 138 for positioning in the first opening 128. The first screw 138 may as shown be a cortical screw and is similar to the screw 38 of the nail assembly 10 of FIGS. 1-9. The first opening 128 is positioned such that the first opening centerline 134 extends from greater trochanter 44 to lesser trochanter 46.

Figure 15:
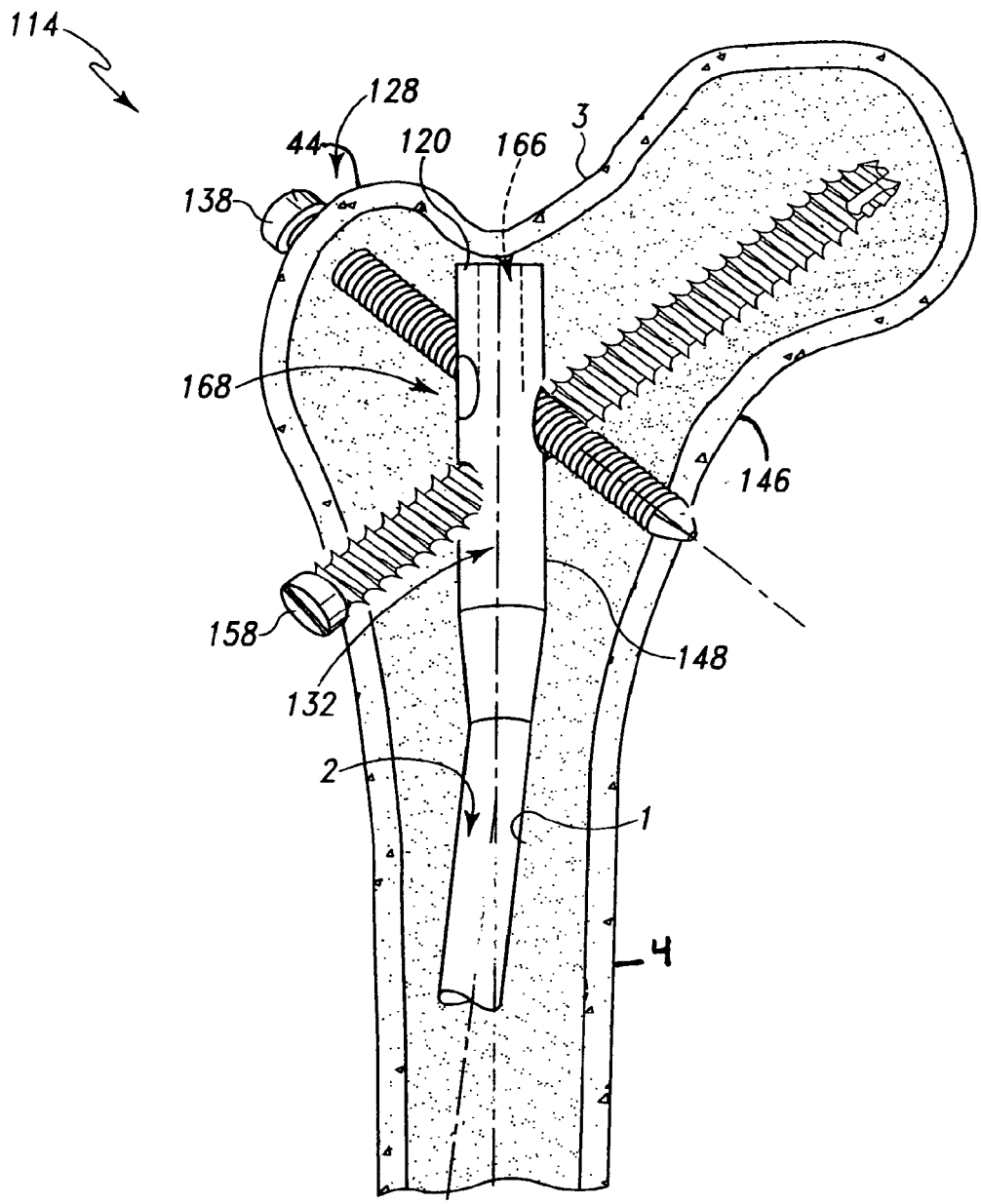
FIG. 15 is an enlarged partial anterior/posterior view of the proximal end of the intramedullary nail of FIG. 11 implanted in a right femur with a greater trochanter/lesser trochanter screw and a partially threaded femoral neck screw in use to form a nail assembly according to the present invention.

Referring now to FIG. 15, yet another embodiment of the present invention is shown as intramedullary nail assembly 114. The intramedullary nail assembly 114 is used to connect the lesser and greater trochanter 144 and 146, respectively, as well as to secure the femoral neck 3 to the femur 4.

The nail assembly 114 as shown in FIG. 15, is adapted for use with a right femur. The nail assembly 114 includes the nail 120. First screw 138, as well as, second screw 158. The second screw 158 is similar to second screw 58 of the nail assembly 10 of FIGS. 1-9. The second screw 158 is adapted for engagement with the femoral neck 3 and is preferably in the form of a cancellous screw.

The first screw 138 is fitted into the first opening 128, while the second screw 158 is fitted into the second opening 132. The first screw 138 extends from the greater trochanter 44 to the lesser trochanter 46. The second screw 158 extends from the outer cortical wall of the long bone or femur 4 through the second opening 132 and into cancellous bone within the neck 3 and head 5 of the femur 4.

As shown in FIG. 15, the first screw 138 and the second screw 158, when installed in the nail 120, form an (X) shape with the nail 120. The first screw 138 and second screw 158 may both be installed simultaneously because the first screw opening 128 and the second screw opening 132 are not coplanar, but they are oblique with respect to each other. Therefore, the first opening 128 and the second opening 132 do not intersect with each other. Therefore, the first screw 138 and the second screw 158, when both are installed into the nail 120, do not intersect with each other and therefore may both be utilized simultaneously.

Figure 16:
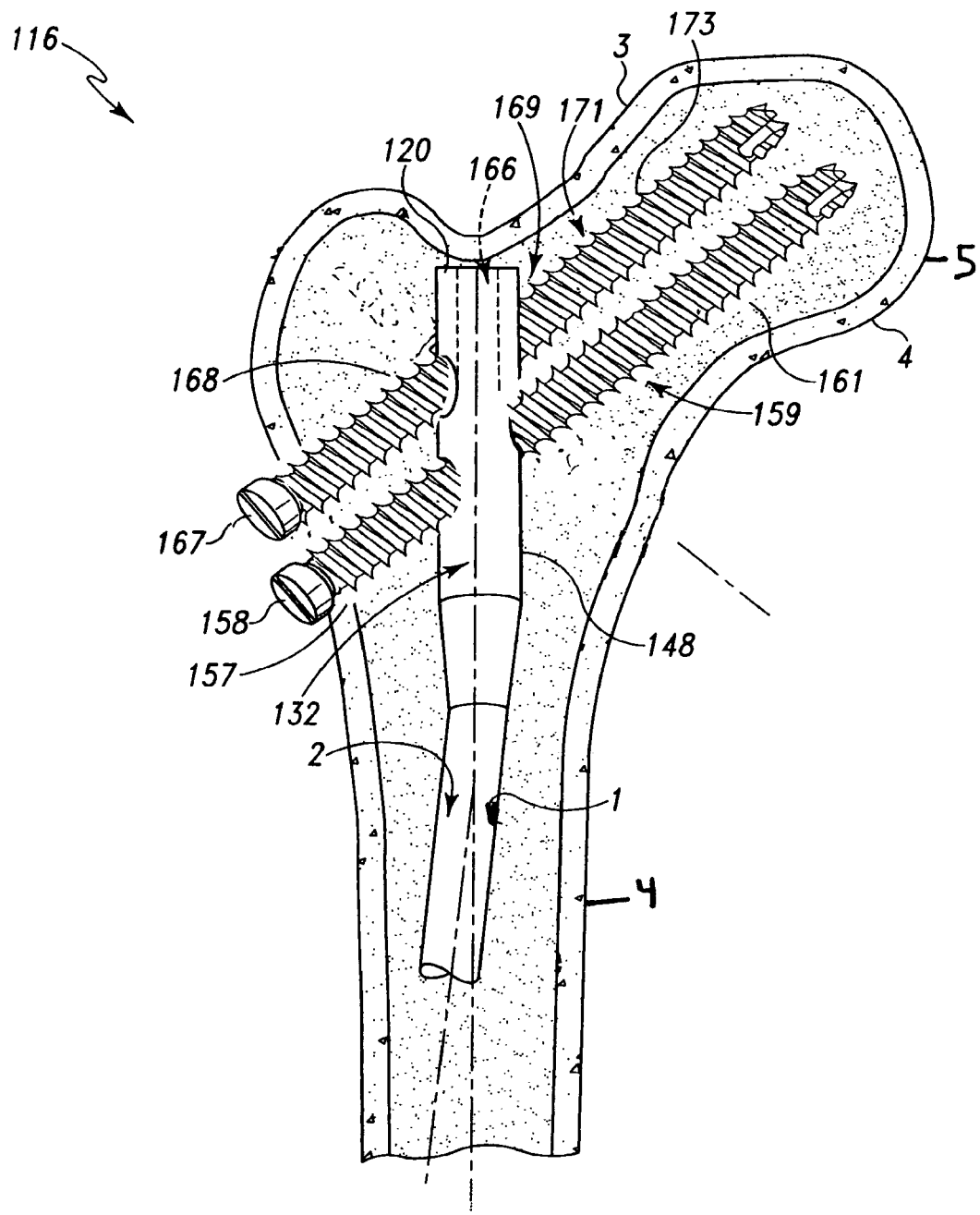
FIG. 16 is an enlarged partial anterior/posterior view of the proximal end of the intramedullary nail of FIG. 11 implanted in a right femur with two partially threaded femoral neck screws in use.

Referring now to FIG. 16, yet another embodiment of the present invention is shown as nail assembly 116. The nail assembly 116 includes the nail 120 as well as second screw 158 and third screw 167. The third screw 167 may be similar or even identical to the second screw 158.

The second screw 158 extends through second opening 132 and extends from the outer cortical wall of the femur 4 through the second opening 132 and into the cancellous bone of the neck 3 and head 5. Similarly, the third screw 167 is fitted in the third opening 168. The third screw 167 may, for simplicity, be in a position spaced from and parallel to the second screw 158. The third screw 167 extends from the outer cortical wall of the femur 4, through the third opening 168 and into the cancellous bone in the neck 3 and head 5 of the femur 4.

As shown in FIG. 16, the second screw 158 and the third screw 167 may, as is shown in FIG. 16, include a smooth portion for assisting in providing for sliding compression of the femoral neck fracture. For example and as shown in FIG. 16, the second screw 158 includes a smooth portion 157 for positioning through the second opening 132. The smooth portion 157 assists in the sliding compression of the fracture. The second screw 158 further includes a threaded portion 159 having cancellous threads 161, which are located in the neck 3 and head 5 of the femur 4. The third screw 167 is similar to the second screw 158 and includes a smooth shank portion 169 slidably fitted in the third opening 168. The third screw 167 further includes a threaded portion 171 extending outwardly from the threaded portion 169. The threaded portion 171 includes cancellous threads 173 for cooperation with the cancellous bone in the neck 3 and head 5.

Figure 17:
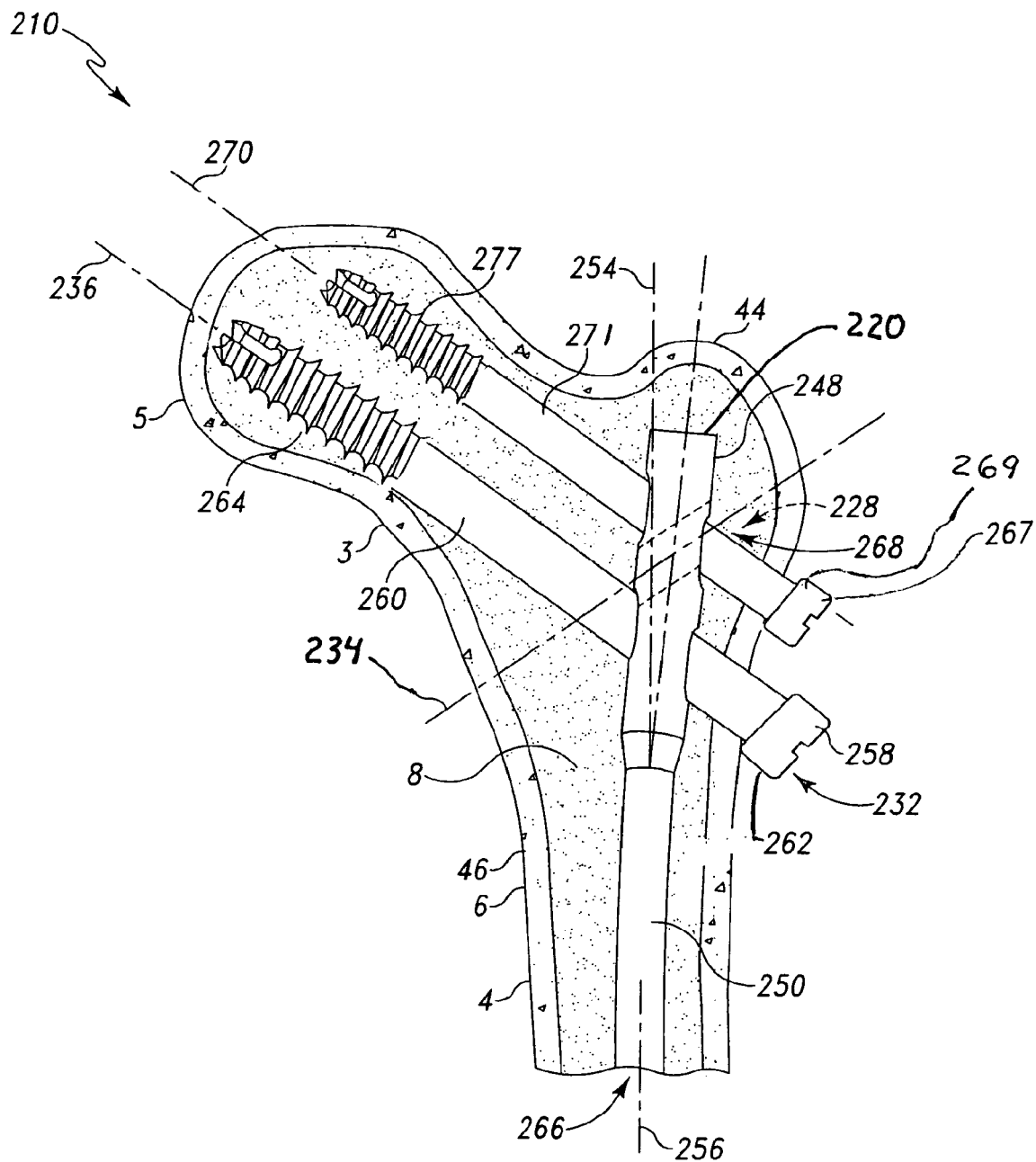
FIG. 17 is a partial anterior/posterior view of a intramedullary nail assembly in accordance with another embodiment of the present invention in the form of a left femoral trochanteric nail with two partially threaded femoral neck screws, one being a cannulated lag screw in use to form a nail assembly implanted in a left femur.

Referring now to FIG. 17, yet another embodiment of the present invention is shown as nail assembly 210. The nail assembly 210 is similar to the nail assembly 16 of FIG. 7, except that the nail assembly 210 of FIG. 17 uses screws, which have a different thread form to minimize medial migration of the thread through the head 5 and femoral neck 3. For example and as shown in FIG. 17, the nail assembly 210 includes nail 220 which is similar to the nail 20 of FIG. 7, except that the openings in the nail 220 may be larger to accommodate larger diameter screws. The nail 220 includes a proximal portion 248 as well as a distal portion 250 extending from the proximal portion 248. The nail 220 may be solid or may, as is shown in FIG. 17, be hollow or include a central opening or cannula 266 extending longitudinally through the central portion of the nail 220.

The proximal portion 248 defines a proximal portion centerline 254 and the distal portion 250 defines a distal portion centerline 256. The proximal portion centerline 254 and the distal portion centerline 256 define an angle α" therebetween. The angle α" is established to assist the installation of the nail 220 through greater trochanter 44.

The nail 220 is adapted for use with femoral neck fractures as well as greater trochanter to lesser trochanter fractures. Therefore, and as shown in FIG. 17, the nail 220 includes a first opening 228 extending in the direction of first opening centerline 234. The first opening centerline 234 extends from greater trochanter 44 to lesser trochanter 46. The nail 220 further includes a second opening 232, which defines second opening centerline 236. The second opening centerline 236 is oriented in a direction toward the neck 3 and head 5 of the femur 4. The second opening 232 may be larger than the opening 32 of the nail 20 to accommodate a larger fastener.

The nail 220 further includes a third opening 268 positioned in a direction along third opening centerline 270. As shown in FIG. 17, the third opening centerline 270 is parallel and spaced from the second opening centerline 236. The third opening 268 may be smaller in size than the second opening 232 to receive a smaller screw. The third opening 268 may be provided to provide for a smaller screw that may serve as anti-rotation screw for the nail assembly 210.

The nail assembly 210 includes a second screw 258 that is slidably fitted in the second opening 232 of the nail 220. The second screw 258 is different than the second screw 58 of the nail assembly 10. The second screw 258 is adapted to limit the medial migration of the screw 258. The second screw 258 includes a head 262 and a shank 260 extending from the head 262. The shank 260 may include external cancellous screw threads 264 for engaging with the cancellous bone 8 located in the neck 3 and head 5 of femur 4.

The nail assembly 210 may further include a third screw 267. The third screw 267 extends along centerline 270 of the third opening 268 and is slidably positioned within the third opening 268 of the nail 220. The third screw 267 may, as is shown in FIG. 17, be parallel and spaced from the second screw 258. The third screw 267 may be smaller in diameter than the second screw 258. Since the third screw 267 may be utilized as an anti-rotation device, the third screw 267 may be substantially smaller than the second screw 258. The third screw 267 may include a head 269 and a shank 271. The shank 271 may include threads 277 for engaging cancellous bone 8 formed in the neck 3 and head 5 of femur 4.

The length of the second screw 258 and the third screw 267 are determined so that the screw head rests against the cortical wall 6 of the femur 4 and the screw shank extends into the head 5 of the femur 4.

Figure 17A:
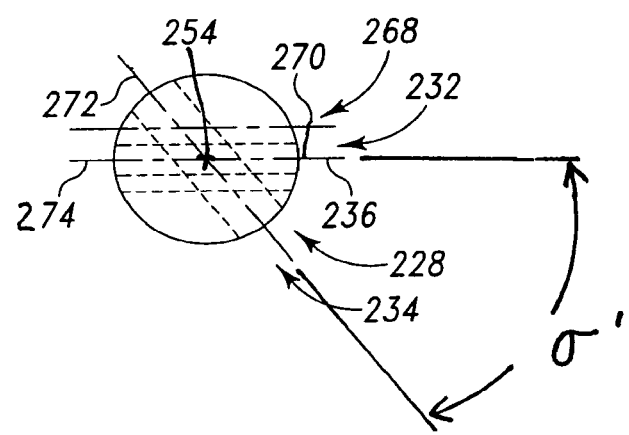
FIG. 17A is an end view of the nail assembly of FIG. 17 showing the angular relationships of the screws.

Referring now to FIG. 17A, the first opening 228, the second opening 232, and the third opening 268 of the nail 220 are shown in greater detail. First opening centerline 234 intersects centerline 254 of the proximal portion 248 of the nail 220. The first opening centerline 234 and proximal portion centerline 256 defines first plane 272. The second opening centerline 236 also intersects centerline 254 of the proximal portion 248. The third opening centerline 270 also intersects centerline 254 of the proximal portion 248 of the nail 220. In fact, the second opening centerline 236 and the third opening centerline 270 form second plane 274. The first plane 272 and the second plane 274, as shown in FIG. 17A, form angle σ' therebetween.

Figure 18:
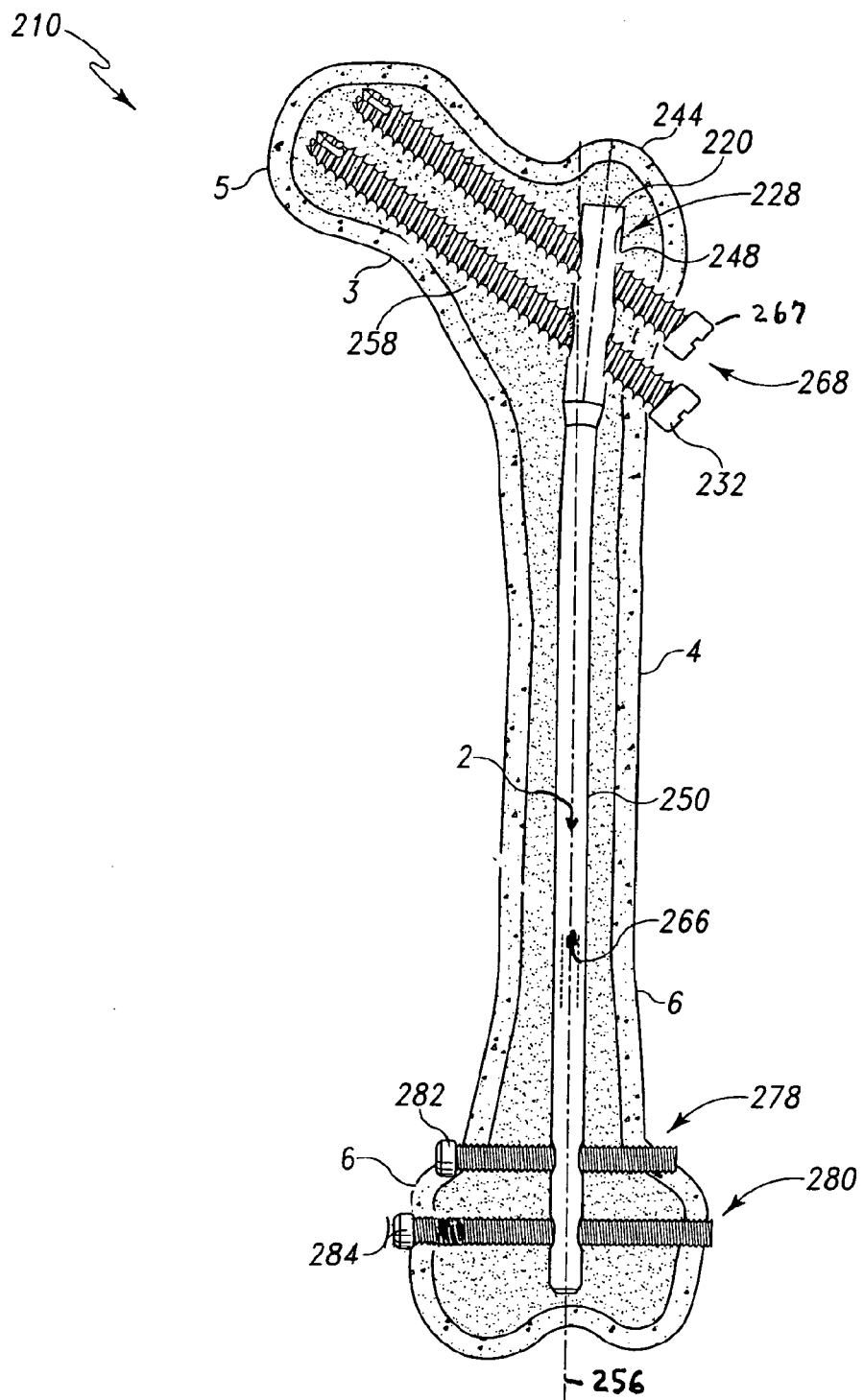
FIG. 18 is an anterior/posterior view of the intramedullary nail of the intramedullary nail assembly of FIG. 17.

Referring now to FIG. 18, the nail assembly 210 is shown in the anterior/posterior view. The nail assembly 210 includes the proximal portion 248, as well as, the distal portion 250. The proximal portion 248 includes first opening 228, second opening 232, and third opening 268.

The distal portion 250 of the nail 220 of the nail assembly 210 includes a first distal opening 278 which may, as shown in FIG. 18, be substantially perpendicular or transverse to longitudinal axis 256 of the nail 220. The distal portion 250 of the nail 220 may further include a second distal opening 280 spaced from and parallel to the first distal opening 278. The first distal opening 278 and the second distal opening 280 may be utilized in cooperation with fasteners to provide for distal fixation of the nail 220.

For example, and as is shown in FIG. 18, the nail assembly 210 further includes a first distal screw 282 that is fitted through the first distal opening 278 of the nail 220. The nail assembly 210 may further include a second distal screw 284 that is fitted through the second distal opening 280. The first distal screw 282 and the second distal screw 284 may be in the form of cortical screws and may engage with the external cortical walls 6 of the femur 4.

Figure 19:
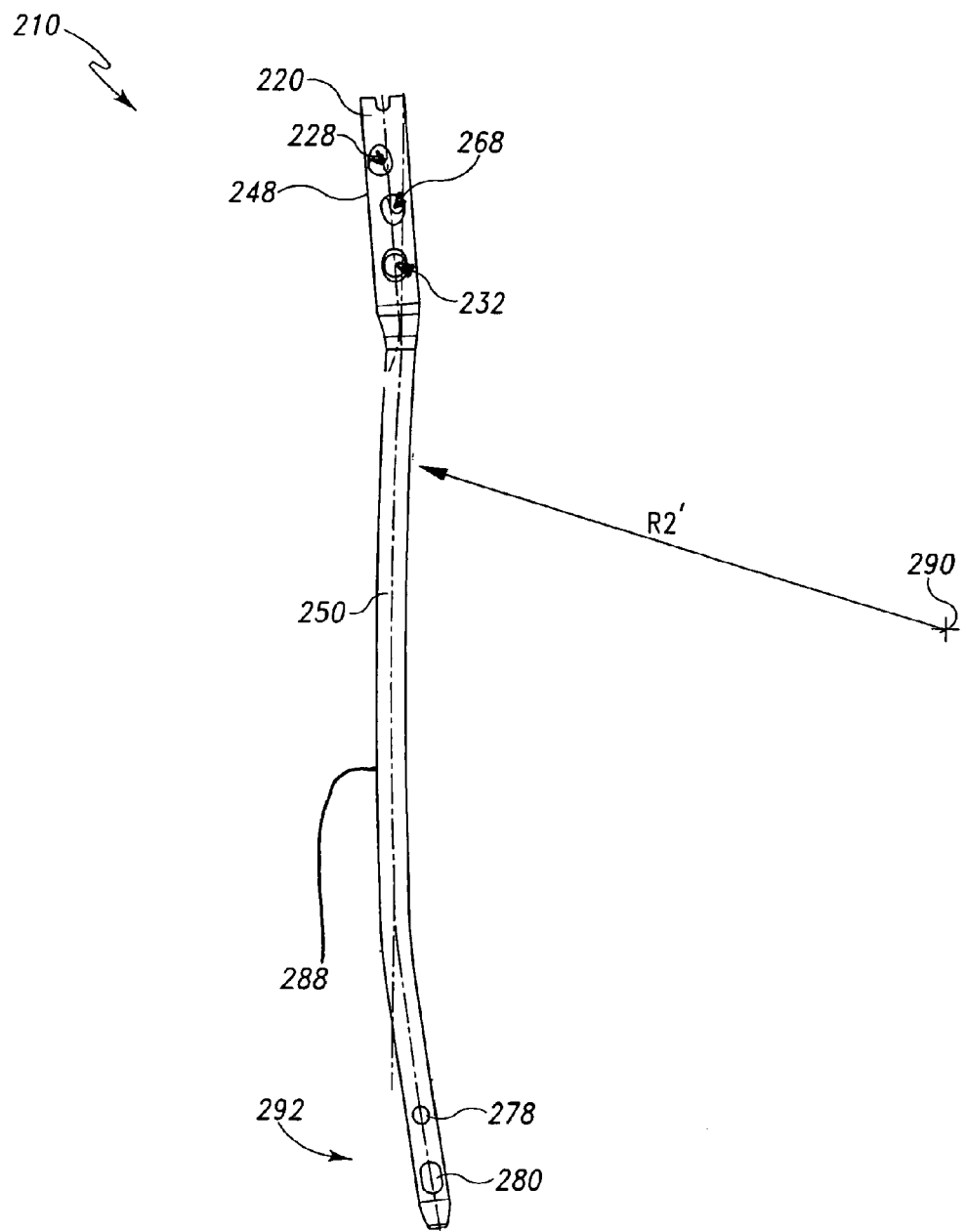
FIG. 19 is a medial/lateral view of the intramedullary nail of FIG. 18.

Referring now to FIG. 19, a medial/lateral view of the nail 220 of the nail assembly 210 is shown. The nail 220 includes the proximal portion 248, as well as, the distal portion 250. The distal portion 250 may, as is shown in FIG. 19, have a shape generally conforming to that of the canal of the long bone. For example, and as is shown in FIG. 19, the distal portion 250 may include an arcuate portion 288 and an end portion 292 extending from the arcuate portion 288. The arcuate portion 288 may be defined by a radius R2' extending from origin 290. The end portion 292 of the distal portion 250 may extend from the arcuate portion 288 and may be generally linear.

Figure 20:
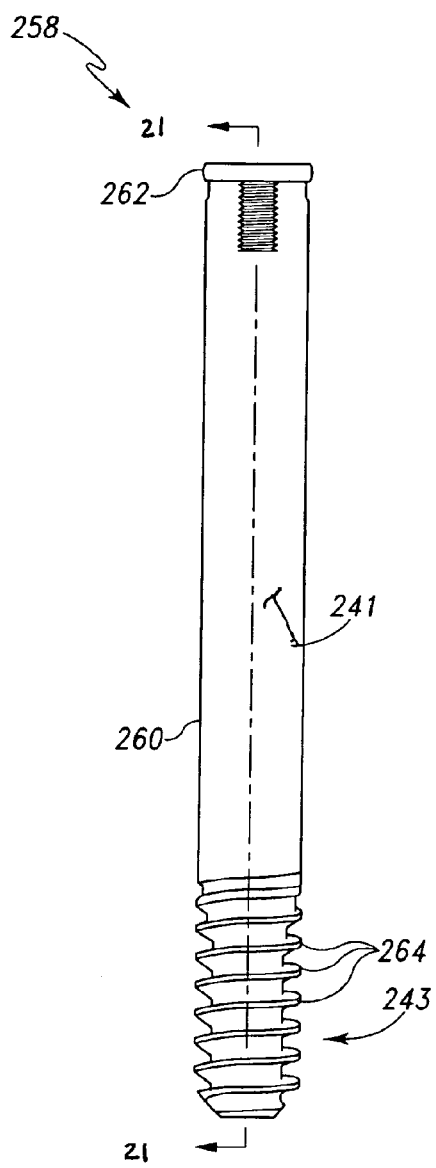
FIG. 20 is an plan view of a lag screw for use in the nail assembly of FIG. 17.
Figure 21:
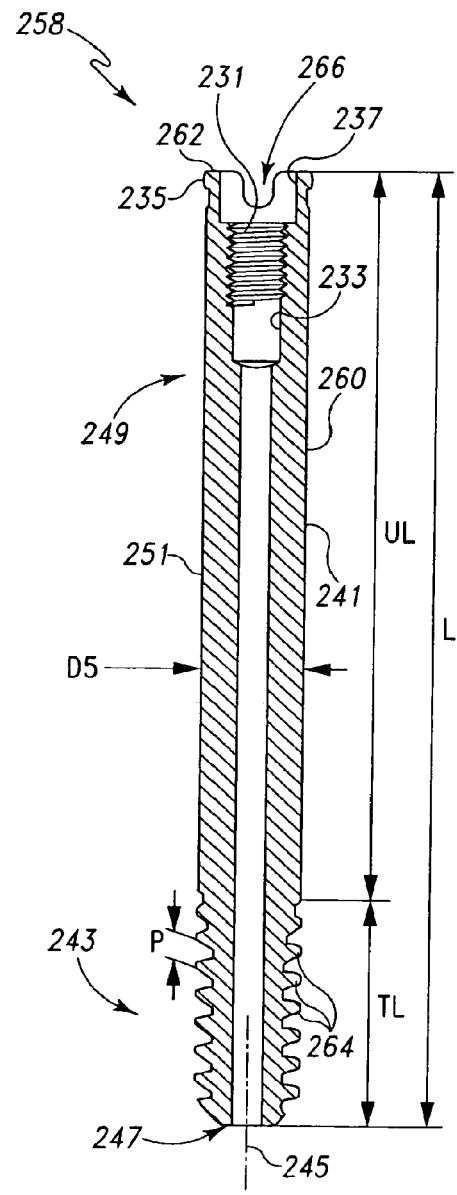
FIG. 21 is a cross sectional view of the lag screw of FIG. 20 along the line 21-21 in the direction of the arrows.

Referring now to FIGS. 20 and 21, the screw 258 may further include a removal feature 231 in the form of, for example, internal threads formed in the small counter bore 233 formed in the longitudinal opening 266 adjacent second end 235 of the screws 258. The screw 258 may further include a large counter bore 237 extending from the second end 235 of the lag screw 258 and concentric with the small counter bore 233 as well as with the longitudinal opening 266.

Referring now to FIG. 21, the screw 258 may further include a plurality of threads 264 formed on the shank periphery 241 of shank 260 of the screw 258. The threads 264 may as shown in FIG. 21 have a non-uniform cross-section, which is more fully described in U.S. patent Ser. No. 11/168,737 incorporated hereby in its entirety.

Referring again to FIG. 21, the periphery 241 of the shank 260 of the screw 258 includes a first portion 243 into which the threads 264 are formed. It should be appreciated that the first portion 243 may extend along longitudinal axis 245 of the screw 258 from first end 247 to second end 325 of the screw 258. It should also be appreciated and as is shown in FIG. 21, that the periphery 241 may include a second portion 249. The second portion 249 of periphery 241 of the shank 260 may define a smooth surface 251. As is shown in FIG. 21, the periphery 241 of the shank 260 may be generally cylindrical and defined by a diameter, for example, DS.

The screw 258 as is shown in FIG. 21, is generally cylindrical and defined by the diameter DS and an overall length L. The shank 260 of the screw includes the first portion 243 which include threads 264 and the second portion 249 having the smooth surface 251. The overall length L, of the diameter DS is divided into a thread TL and a smooth or unthreaded length UL. The thread length TL defines the first portion 243 and the smooth length UL defines the second portion 249. The thread length TL may, for example, be a portion of, for example, 20-40% of the overall length L of the shank 260. It should be appreciated that the smooth length UL is preferably a sufficient length such that the second portion 249 of the screw 258 may be positioned in the oblique third opening 268 of the intramedullary nail 220 (see FIG. 17) to permit compression of the bone fracture of femur 4.

The threads 264 as is shown in FIG. 21, may advance spirally around the periphery 241 of the shank 260 of the screw 258. The threads 264 may be defined by a pitch P defining a spacing along longitudinal axis 245 between adjacent threads. The threads 264 may advance spirally around the longitudinal axis 245 in either a right or a left hand spiral configuration. The threads may, as is shown in FIG. 21, be of a single lead type but may alternatively be double lead configuration or a triple lead configuration.

Figure 23:
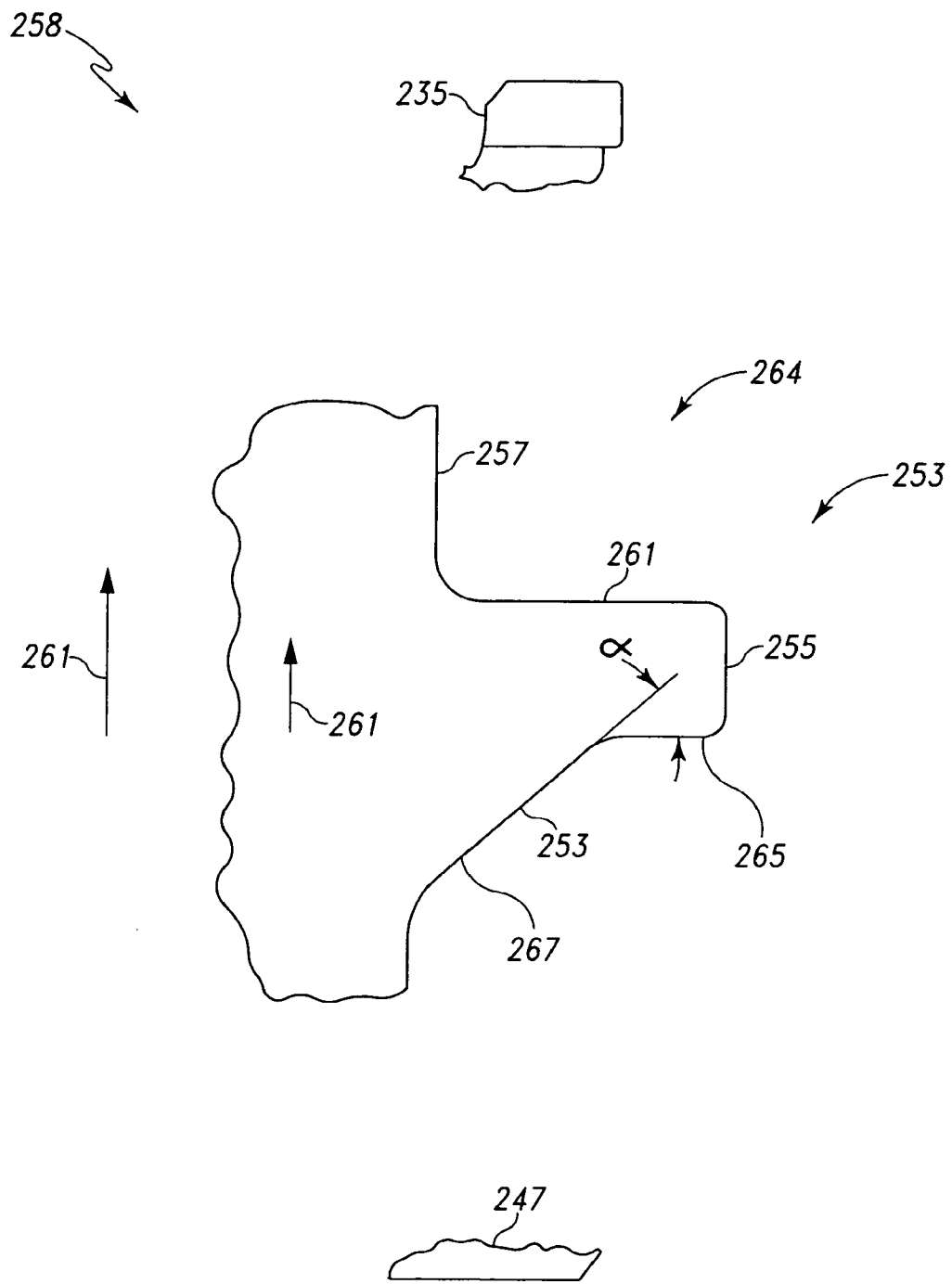
FIG. 23 is an enlarged cross-sectional view of the box shaped thread of the screw of FIG. 22.

Referring now to FIG. 23, the threads 264 may have any suitable shape or thread form. For example and as shown in FIG. 23, the threads 264 may have a combination box and tapered configuration. For example and is shown in FIG. 23, the threads 264 may have any suitable shape or profile 253. For example and is shown in FIG. 23 the profile 253 may include a crest 255 and opposed root 257. A trailing surface 261 is positioned between the crest 255 and the root 257 adjacent the second end 235 of the screw 258 while leading edge 263 is positioned between the crest 255 and root 257 adjacent the first end 247 of the screw 258.

As shown in FIG. 23, the leading edge 263 and the trailing edge 261 may be configured to provide for less force to assemble in the direction of arrow 261 than to disassemble in the direction opposed to arrow 261. Such ease of assembly and difficulty in disassembly may be accomplished as is shown in FIG. 23 by providing the trailing edge 261 with a configuration that is normal or perpendicular to the root 257 and the crest 255 while providing the leading edge 263 with chamfered or angled surface or, as is shown in FIG. 23, or with a partially angled surface between the crest 255 and the root 257.

Referring to FIG. 23, the threads 267 are shown in greater detail. The threads 264 of the screw 258 may, as is shown in FIG. 23, include the leading edge 263 such that the leading edge 263 includes normal or perpendicular portion 265 as well as an angled portion 267. The angled portion 267 provides for reduced force to assemble the screw 258 into the long bone or femur 4. The normal portion 265 and the angled portion 267 may define an angle αα therebetween. To minimize stress, the crest 255, the root 257, trailing edge 261, and leading edge 263 may include arcuate portions therebetween to minimize the stress.

Figure 22A:
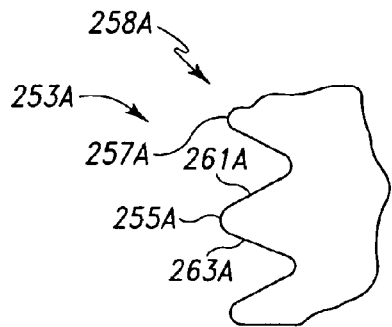
FIG. 22A is a partial view of a standard thread form for an alternate lag screw for use with an alternate embodiment of the intramedullary nail assembly of the present invention.
Figure 22D:
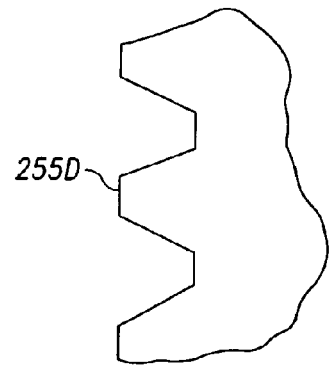
FIG. 22D is a partial view of a truncated V-shaped thread form for an alternate lag screw for use with an alternate embodiment of the intramedullary nail assembly of the present invention.
Figure 22B:
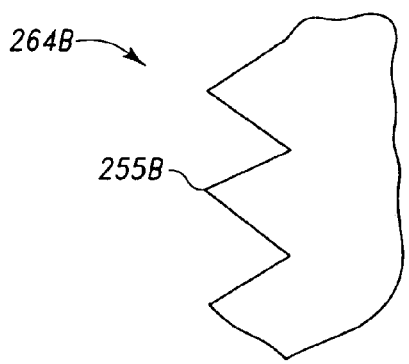
FIG. 22B is a partial view of a V-shaped thread form for an alternate lag screw for use with an alternate embodiment of the intramedullary nail assembly of the present invention.
Figure 22E:
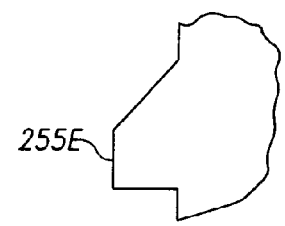
FIG. 22E is a partial view of a reverse box thread form for an alternate lag screw for use with an alternate embodiment of the intramedullary nail assembly of the present invention.
Figure 22C:
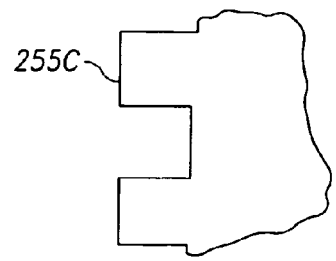
FIG. 22C is a partial view of a square-shaped thread form for an alternate lag screw for use with an alternate embodiment of the intramedullary nail assembly of the present invention.
Figure 22:
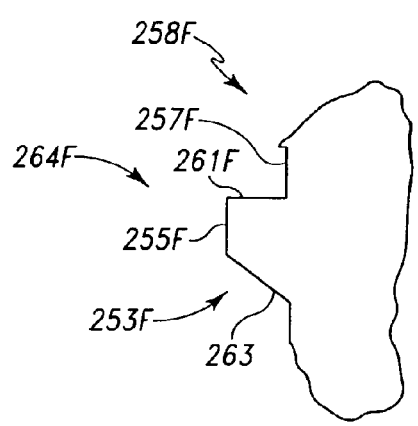
FIG. 22 is a partial view of a box type form for an alternate lag screw for use with an alternate embodiment of the intramedullary nail assembly of the present invention.

Referring now to FIG. 22-22E, alternative profile configuration for threads of the screw of the nail of the present invention is shown. According to the present invention and referring now to FIG. 22, another form of profile of the screw of the present invention. The screw 258F of FIG. 22 includes threads 264F defining profile 253F. The profile 253F includes a spaced apart parallel crest 255F and root 257F. The profile 253F includes a trailing surface 261F, which is normal to the root 257F and the crest 255F. The profile 253F further includes a leading surface 263F, which is positioned at angle between root 257F and crest 255F.

Referring now to FIG. 22A, profile 253A is shown which includes arcuate roots and crest. For example and is shown in FIG. 22A, the profile 253A of screw 258A includes an arcuate crest 255A to which trailing angled surface 261A extends. Leading edge 263A extends likewise from the arcuate crest 255A. The profile 253A further includes an arcuate root 257A, which connects with trailing surface 261A and leading surface 263A.

Referring now to FIG. 22B, yet another profile for threads for screw of the present invention is shown as screw 258B includes threads 264B having a profile 253B which include generally v-shaped threads 264B. The profile 253B includes trailing surface 261B and leading surface 263B. Root 257B and crest 255A are as shown in FIG. 22B are minimal.

Referring now to FIG. 22C, yet another profile of threads for a screw according to the present invention is shown. For example and is shown in FIG. 22C, the screw 258C includes threads 264C having a profile 253C that is blocked or rectangular. The profile 253C includes parallel and spaced apart root 257C and crest 255C. The profile 253C includes a trailing surface 261C, a spaced apart and parallel leading surface 263C. The trailing surface 261C and the leading surface 263C are normal or perpendicular to the root 257C and the crest 255C.

Referring now to FIG. 22D, yet another embodiment of a profile of threads for a screw according to the present invention is shown. The profile 253D of threads 264D of the screw 258D has a generally truncated v-shape of that of a standard screw thread. The profile 253D includes a flat crest 255D and opposed angled trailing surfaces 261D and leading surface 263D. A root 257D extends from the trailing surface 261D and the leading surface 263D.

Yet another profile of threads of a screw of the present invention is shown as profile 253E. Screw 258E includes threads 264E having the profile 253E. The profile 253E includes a leading surface 263E that is normal to a crest 255E and a spaced apart parallel root 257E. The profile 253E further includes a trailing surface 261E that is positioned at an angle between the root 257E and the crest 255E.

Figure 24:
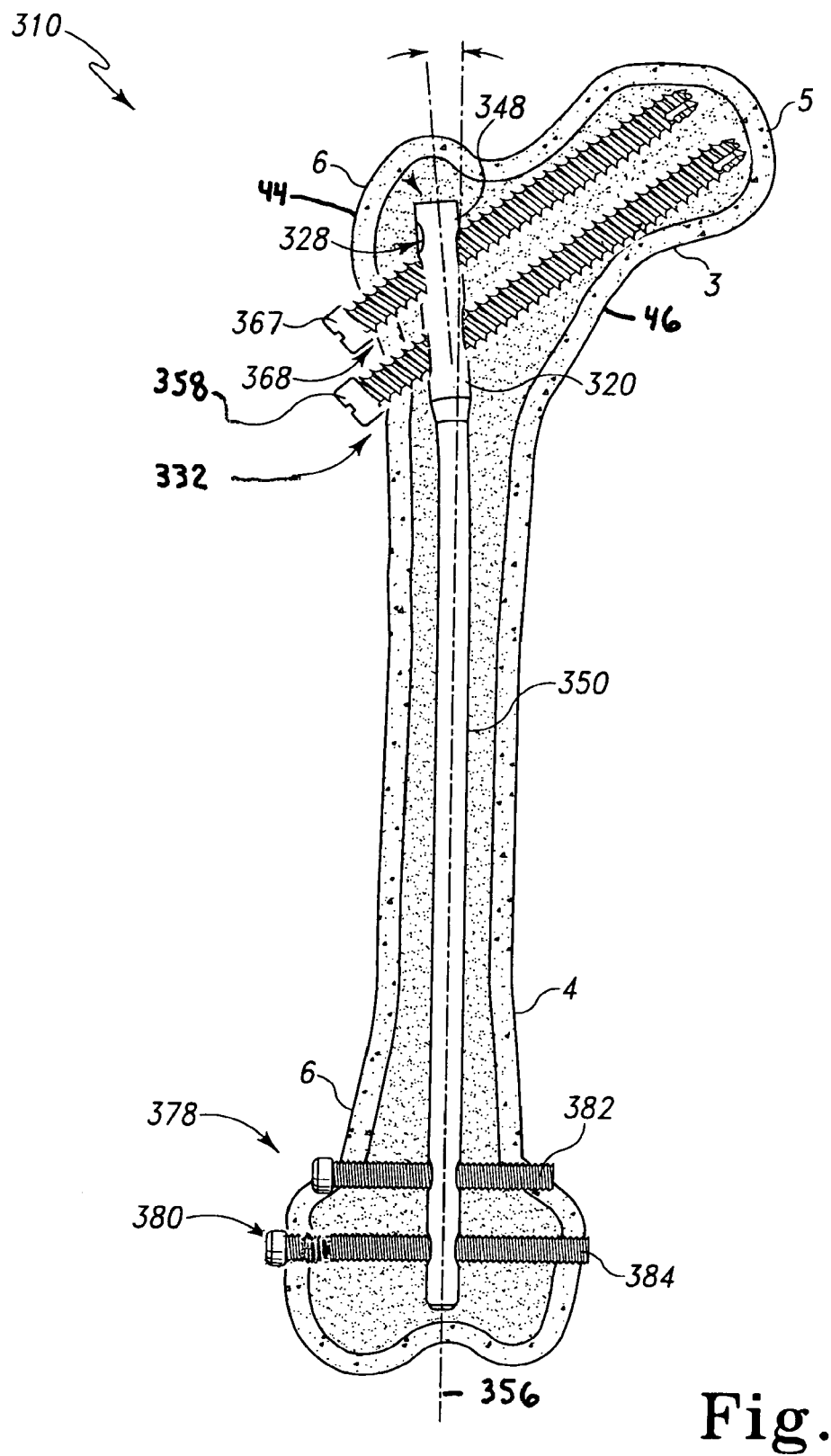
FIG. 24 is an anterior/posterior view of an intramedullary nail in accordance with an embodiment of the present invention in the form of a right femoral trochanteric nail implanted in a right femur.
Figure 25:
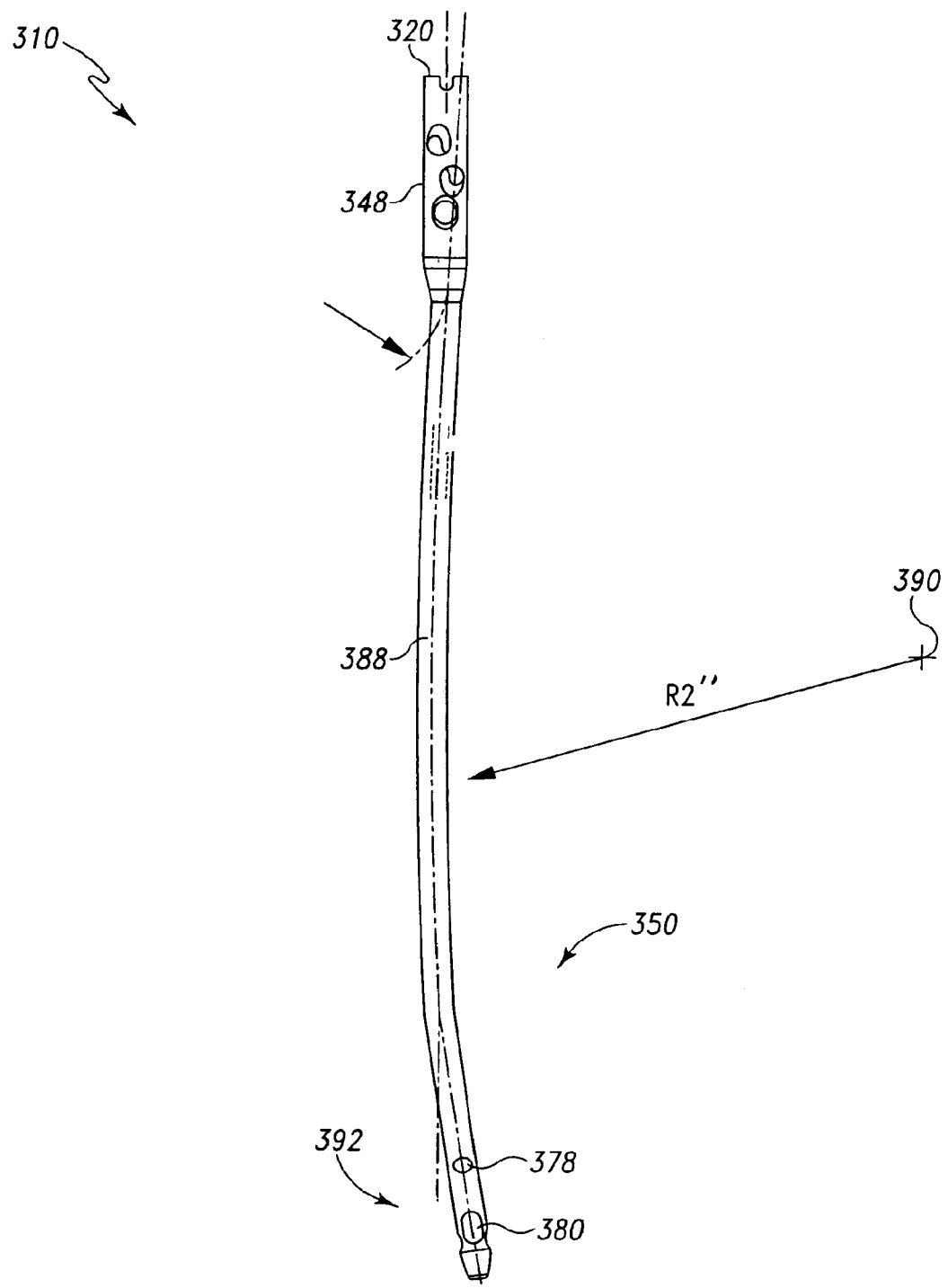
FIG. 25 is a medial/lateral view of the intramedullary nail of FIG. 24.

Referring now to FIGS. 24 and 25, yet another embodiment of the present invention is shown as nail assembly 310. The nail assembly 310 is similar to the nail assembly 14 of FIG. 6, except that the nail assembly 310 is for use with a right femur rather than a left femur. For example and as shown in FIG. 24, the nail assembly 310 includes a nail 320 that is the mirror image of the nail 20 of FIG. 6. The nail 320 includes a proximal portion 348 as well as a distal portion 350. The proximal portion 348 includes a first opening 328 for use in connecting the greater trochanter 44 to the lesser trochanter 46. The proximal portion 348 also includes a second opening 332 and a third opening 368 for engagement with the neck 3 and head 5 of femur 4.

The distal portion 350 of the nail 320 includes a first distal opening 378. The first distal opening 378 may be generally perpendicular or normal to longitudinal axis 356 of the distal portion 350 of the nail 320. The distal portion 350 of the nail 320 may further include a second distal opening 380 spaced from and generally parallel to the first distal opening 378. The first distal opening is sized to receive first distal screw 382. Similarly, the second distal opening 380 is sized to receive second distal screw 384. The first distal screw 382 as well as the second distal screw 384 may, as shown in FIG. 24, be in the form of cortical screws, which engage with cortices 6 of the femur 4.

The nail assembly 310 as shown in FIG. 24, is for use in securing femoral neck fractures and as such, includes a second screw 358, which is slidably fitted in second opening 332. The second screw 358, as is shown in FIG. 24, is a fully threaded screw and extends into the neck 3 and head 5 of femur 4. The second screw 358 may be in the form of a cancellous screw. The nail assembly 310 further includes a third screw 367, which is slidably fitted in the third opening 368. The third screw 367 extends from cortical wall 8 of the femur 4 through the third opening 368 and into the neck 3 and head 5 of femur 4. The third screw 367 is positioned parallel and spaced from the second screw 358. The third screw 367 may be in the form of a fully threaded cancellous screw.

Referring now to FIG. 25, the medial/lateral view of the nail 320 is shown. The nail 320 includes the proximal portion 348 as well as the distal portion 350. The proximal portion 348 may be generally linear. The distal portion 350 may include an arcuate portion 388 as well as an end portion 392. The arcuate portion 388 and the end portion 392 are designed to conform with the canal of a right femur. The arcuate portion 388 may be described, for example, by radius R2'' extending from origin 390. The end portion 392 may extend at, for example, angle θ'''. The end portion 392 may include first distal opening 378, which, as is shown in FIG. 25, may have a generally circular shape. The end portion 392 may further include the second distal opening 380, which may, as shown in FIG. 25, have a generally oval shape.

Figure 26:
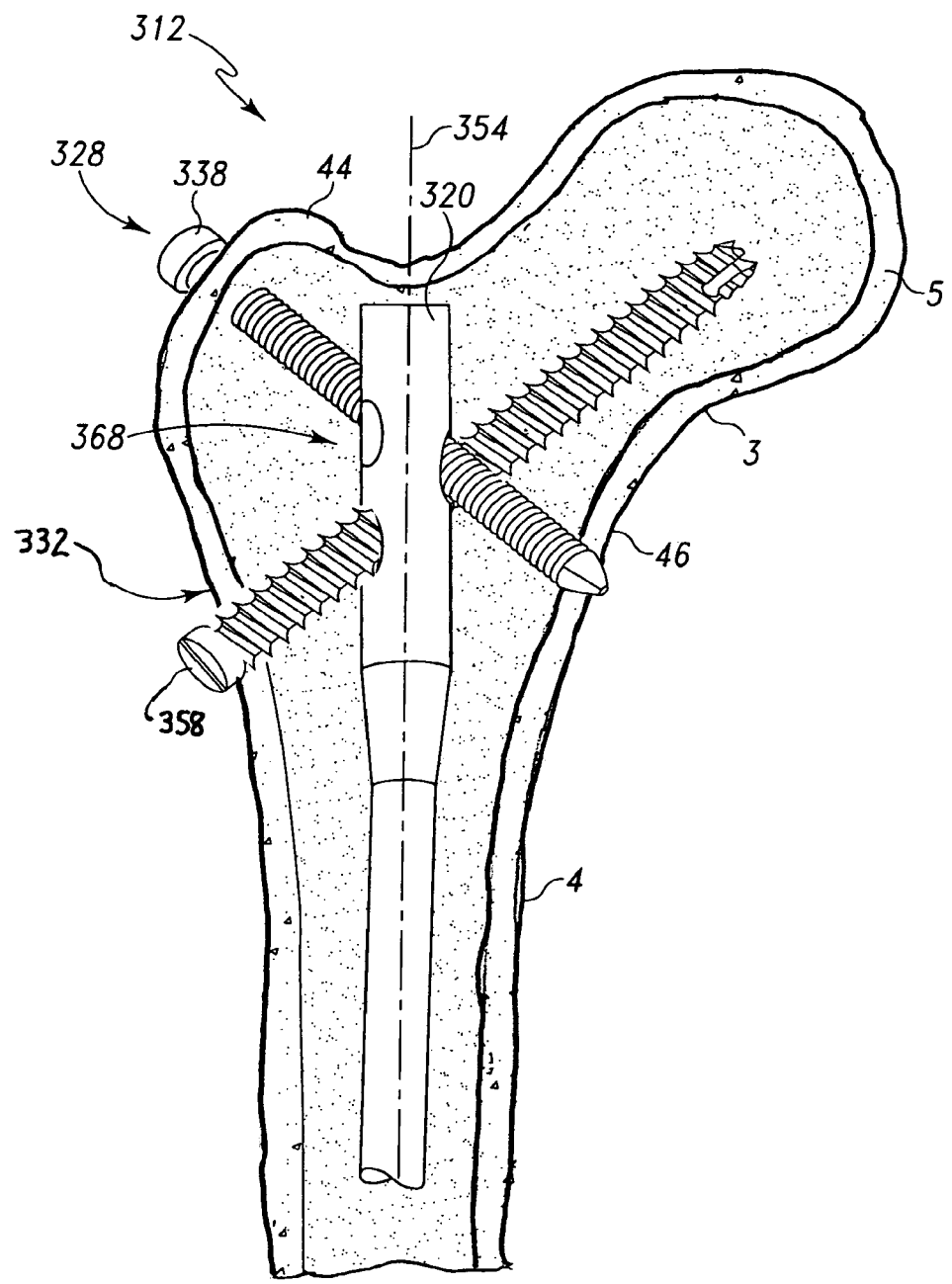
FIG. 26 is an enlarged partial anterior/posterior view of the proximal end of the intramedullary nail of FIG. 11 implanted in a right femur with a greater trochanter/lesser trochanter screw and a femoral neck screw in use to form a nail assembly according to another embodiment of the present invention.

Referring now to FIG. 26, yet another embodiment of the present invention is shown as nail assembly 312. The nail assembly 312 utilizes the nail 320 of FIGS. 24 and 25, but utilizes screws in a different fashion. The nail assembly 312 provides for screws with a generally (X) shape and may be used to repair fractures that include both a greater trochanter to lesser trochanter fracture, as well as a femoral neck fracture. The nail assembly 312 includes the nail 320, as well as, a first screw 338 and second screw 358. The first screw 338 is slidably fitted in the first opening 328 and extends from greater trochanter 44 to lesser trochanter 46. The second screw 358 extends through second opening 332 and engages neck 3 and head 5 of femur 4.

Figures 27, 27A:
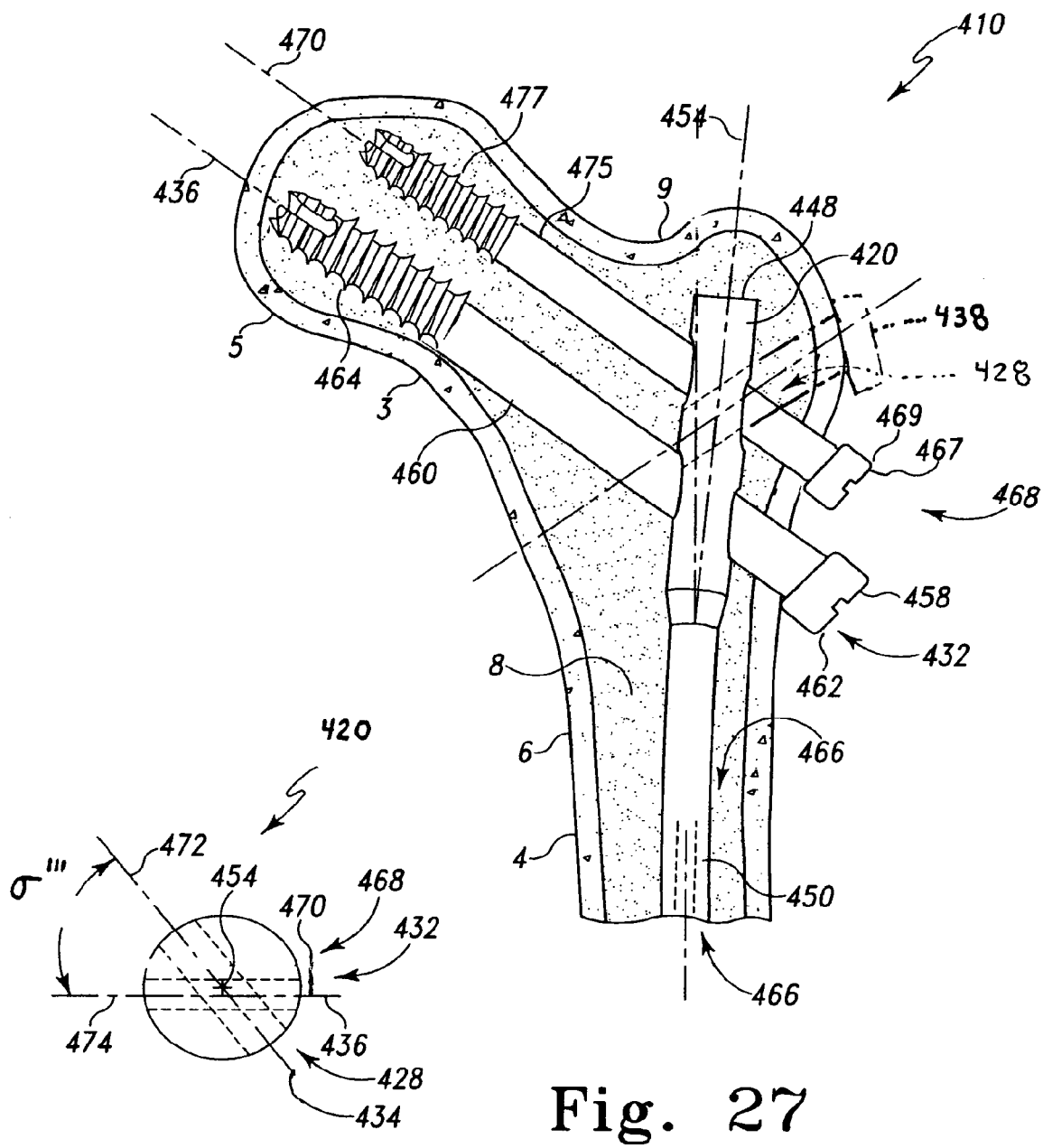
FIG. 27 is a partial anterior/posterior view of a intramedullary nail assembly in accordance with another embodiment of the present invention in the form of a left femoral trochanteric nail with two partially threaded femoral neck screws, one being a cannulated lag screw in use to form a nail assembly implanted in a left femur with a piriforma fossa entry.
FIG. 27A is an end view of the nail assembly of FIG. 27 showing the angular relationships of the screws.

Referring now to FIG. 27, yet another embodiment of the present invention is shown as nail assembly 410. The nail assembly 410 as shown in FIG. 27, is for use in a left femur and includes the nail 410, which is suitable for entry into the piriforma fossa 9 of the femur 4. In that the nail 410 is inserted through piriforma fossa 9 of the femur 4, the nail in the anterior/posterior view as shown in FIG. 27, is generally straight. The nail 410 as shown in FIG. 27, includes a proximal portion 448 and a distal portion 450. The nail 410 may include a central opening or cannula 466 and have a longitudinal centerline 454 that is generally straight or linear in the anterior/posterior view of FIG. 27.

The nail assembly 410 further includes a second screw 458, which is slidably fitted in second opening 432 of the nail 420. The second screw 458, as shown in FIG. 27, is in the form of a partially threaded screw and includes a head 462 and a shank 460, including a portion having threads 464. The second screw 458 extends into the cancellous bone 8 of the neck 3 and head 5 of the femur 4.

The nail assembly 410 of FIG. 27 may further include a third screw 467 slidably fitted into third opening 468 formed in the nail 420. The second opening 432 defines a second opening centerline 436. The third opening 468 defines a third opening centerline 470. The second opening centerline 436 and the third opening centerline 470, as shown in FIG. 27, may be parallel and spaced apart. The nail assembly 420 may further include a third screw as shown in phantom as first screw 438. The first screw 438 may be fitted into first opening 428 formed in the nail 420.

The third screw 467 may include a head 469 that rests against cortical bone 6 of the femur 4. The third screw 467 may include a shank 475 including a smooth part as well as including external threads 477. The external threads 477 of the third screw 467 may be of a cancellous type for fitting and engaging with cancellous bone.

Referring now to FIG. 27A, the openings of the nail 410 are shown in greater detail. The nail 410 includes the first opening 428 extending along first opening centerline 434. The first opening centerline 434 intersects with longitudinal axis 454 of the nail 420. The longitudinal axis 454 of the nail 420 and the first opening centerline 434 define a first plane 472.

The nail 410 further includes the second opening 432 defining second opening centerline 436. The nail 420 further includes the third opening 468, which defines the third opening centerline 470. As shown in FIG. 27A, the second opening centerline 436 and the third opening centerline 470 intersect the centerline 454 of the nail 420. The second opening centerline 436, the third opening centerline 470 and the centerline 454 of the nail 420 define second plane 474. The second plane 474 and the first plane 472 define an angle σ''' therebetween.

Figure 28:
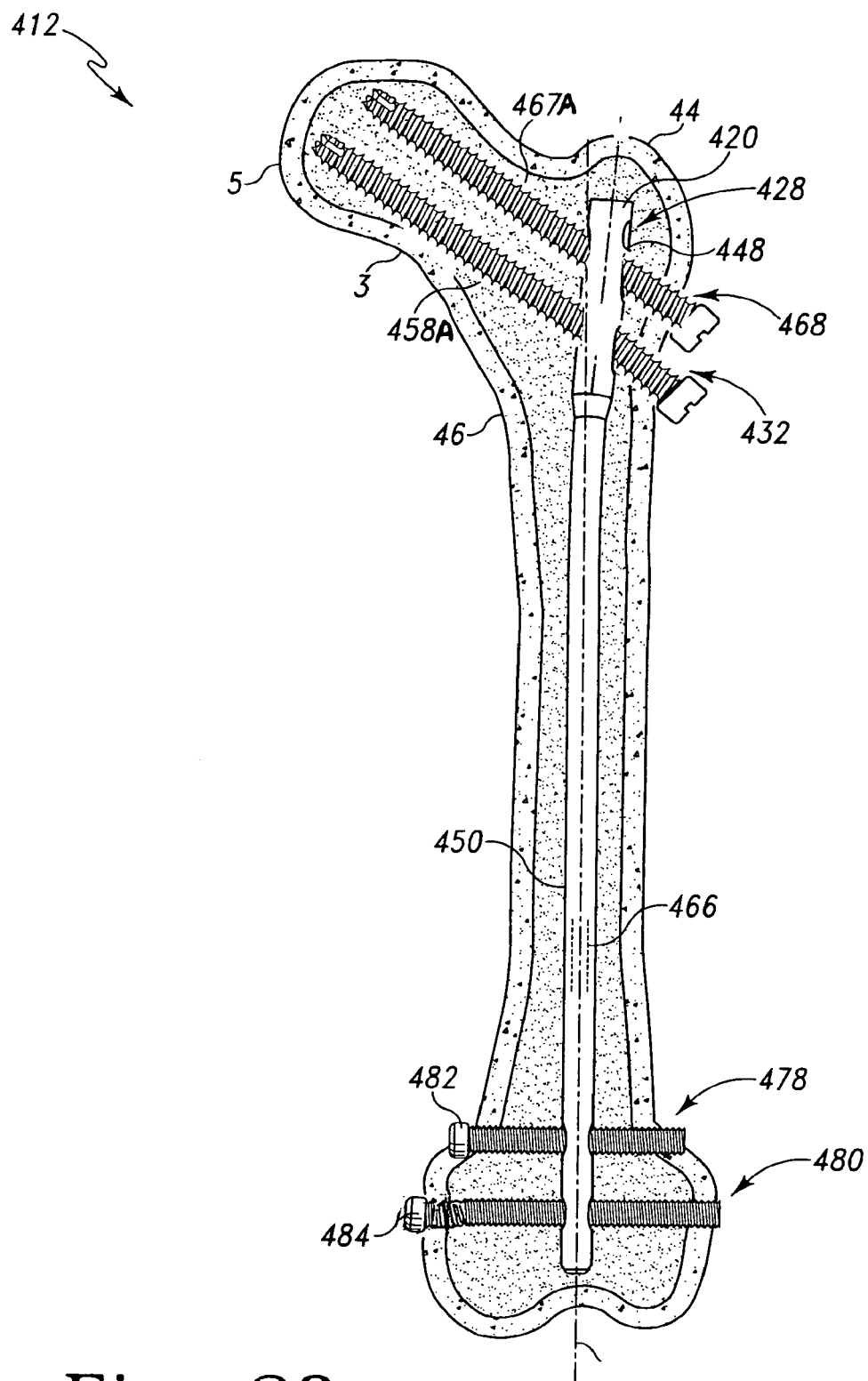
FIG. 28 is an anterior/posterior view of the intramedullary nail of the intramedullary nail assembly of FIG. 27.

Referring now to FIG. 28, yet another embodiment of the present invention is shown as nail assembly 412. The nail assembly 412 is similar to the nail assembly 410 of FIG. 27, but utilizes fully threaded screws rather than partially threaded screws. The nail assembly 412 includes the nail 420 of FIG. 27. The nail 420 includes first opening 428, second opening 432, and third opening 468. The nail 420 includes the proximal portion 448 and the distal portion 450. The nail assembly 412 includes a fully threaded second screw 458A that is slidably fitted in the second opening 432. The nail assembly 412 further includes a fully threaded third screw 467A that is slidably fitted in the third opening 468.

The distal portion 450 of the nail 420 includes a first distal opening 478, which is positioned transversely or perpendicular to the longitudinal axis 454 of the nail 420. The nail 420 may further include a second distal opening 480 spaced from and generally parallel to the first distal opening 478. The nail assembly 412 may further include first distal screw 482, which may be fitted into the first distal opening 478. The nail assembly 412 may also include second distal screw 484 for fitting to the second distal opening 480.

Figure 29:
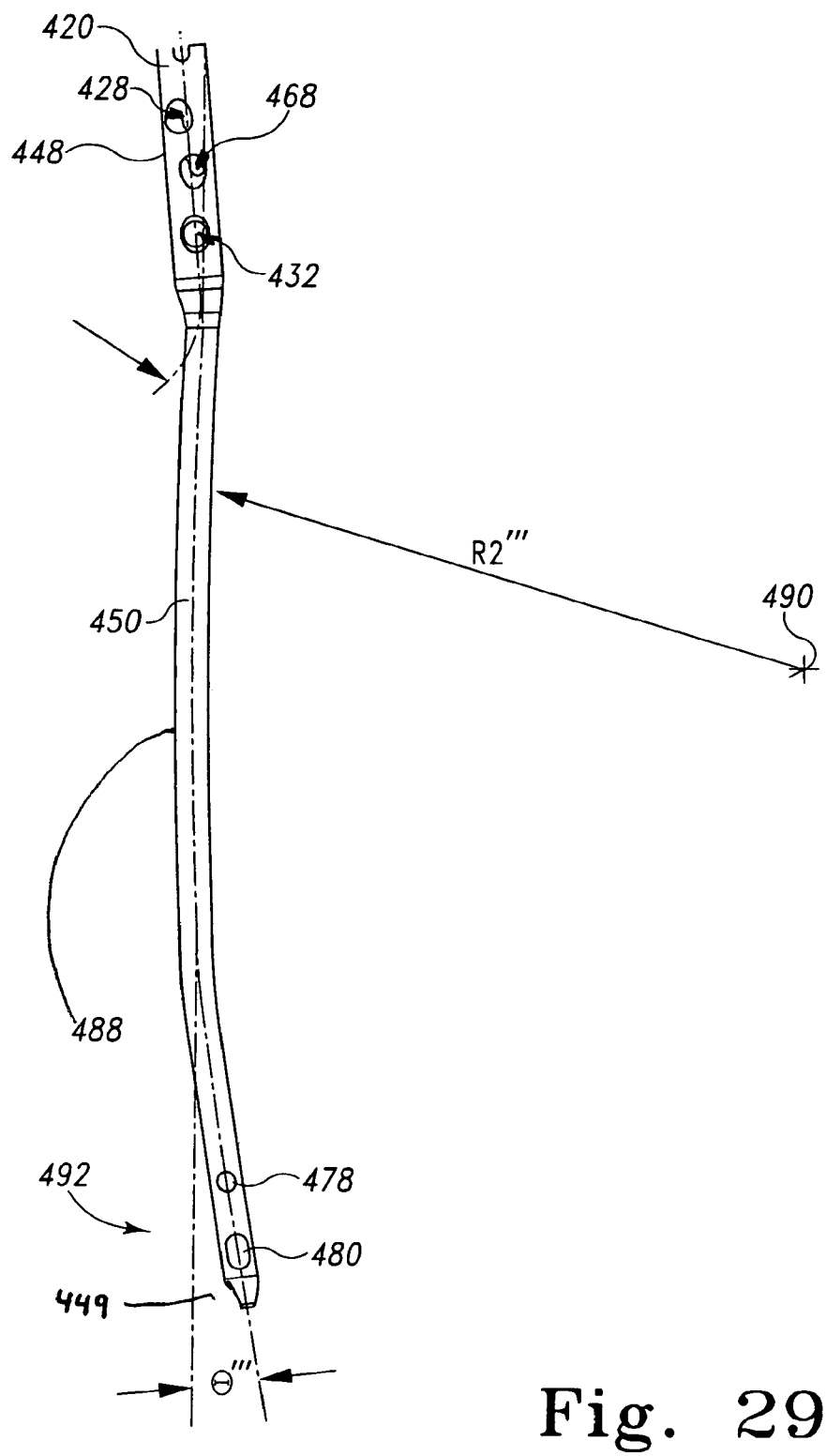
FIG. 29 is a medial/lateral view of the intramedullary nail of FIG. 28.

Referring now to FIG. 29, the medial/lateral view of the nail 420 for use with the nail assembly 410 of FIG. 27, as well as with the nail assembly 412 of FIG. 28 is shown. The nail assembly 420 includes the proximal portion 448 as well as the distal portion 450. The proximal portion 448 includes the first opening 428, the second opening 432 and the third opening 468. The distal portion 450 includes an arcuate portion 488 and an end portion 492. The arcuate portion 488 and the end portion 492 are configured to form into the arcuate intramedullary canal of the left long bone or femur.

The arcuate portion 488 is defined by radius R2''' extending from origin 490. The end portion 492 is generally linear and extends at an angle θ'''' from the arcuate portion 488. The end portion 492 includes the first distal opening 478 and the second distal opening 480. The first distal opening 478 may, as is shown in FIG. 19, be generally cylindrical. The second distal opening 480, as shown in FIG. 19, may be oval.

The nail 410 may, as shown in FIG. 29, include a relief surface such as a flat surface for example a chamfer 449 for assisting in leading the curved nail 410 into the medullary canal of the long bone, for example the femur. It should be appreciated that the chamfer may have a surface that is not flat, for example arcuate, for example a portion of a sphere or a cylinder.

Figures 29A, 29B:
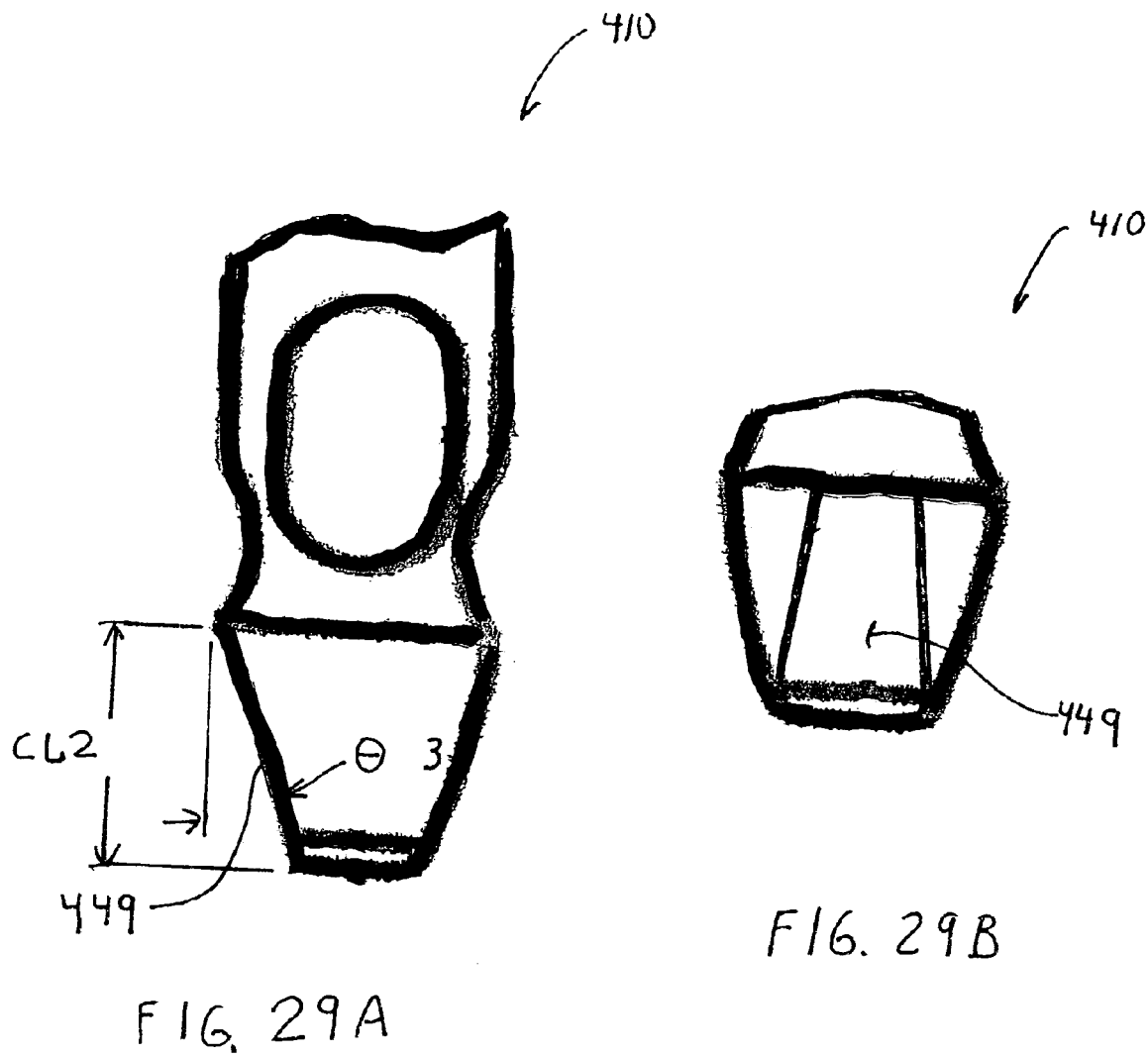
FIG. 29A is an enlarged medial/lateral view of the distal tip of the nail of FIG. 29 showing the chamfer in greater detail.
FIG. 29B is an enlarged anterior/posterior view of the distal tip of the nail of FIG. 29 showing the chamfer in greater detail.

Referring now to FIG. 29A the chamfer 449 is shown in the medial/lateral view with chamfer 449 shown on the side of the distal tip opposed to the origin 490 of the curved portion of the nail 410. The chamfer may be defined by angle θ3 from the longitudinal periphery of the nail 410. The chamfer may be further defined by chamfer length CL2 from the distal end of the nail 410.

Referring now to FIG. 29B the chamfer 449 is shown in the anterior/posterior view with chamfer 449 shown at distal tip. It should be appreciated that the tip may be larger or smaller than shown.

Figure 30:
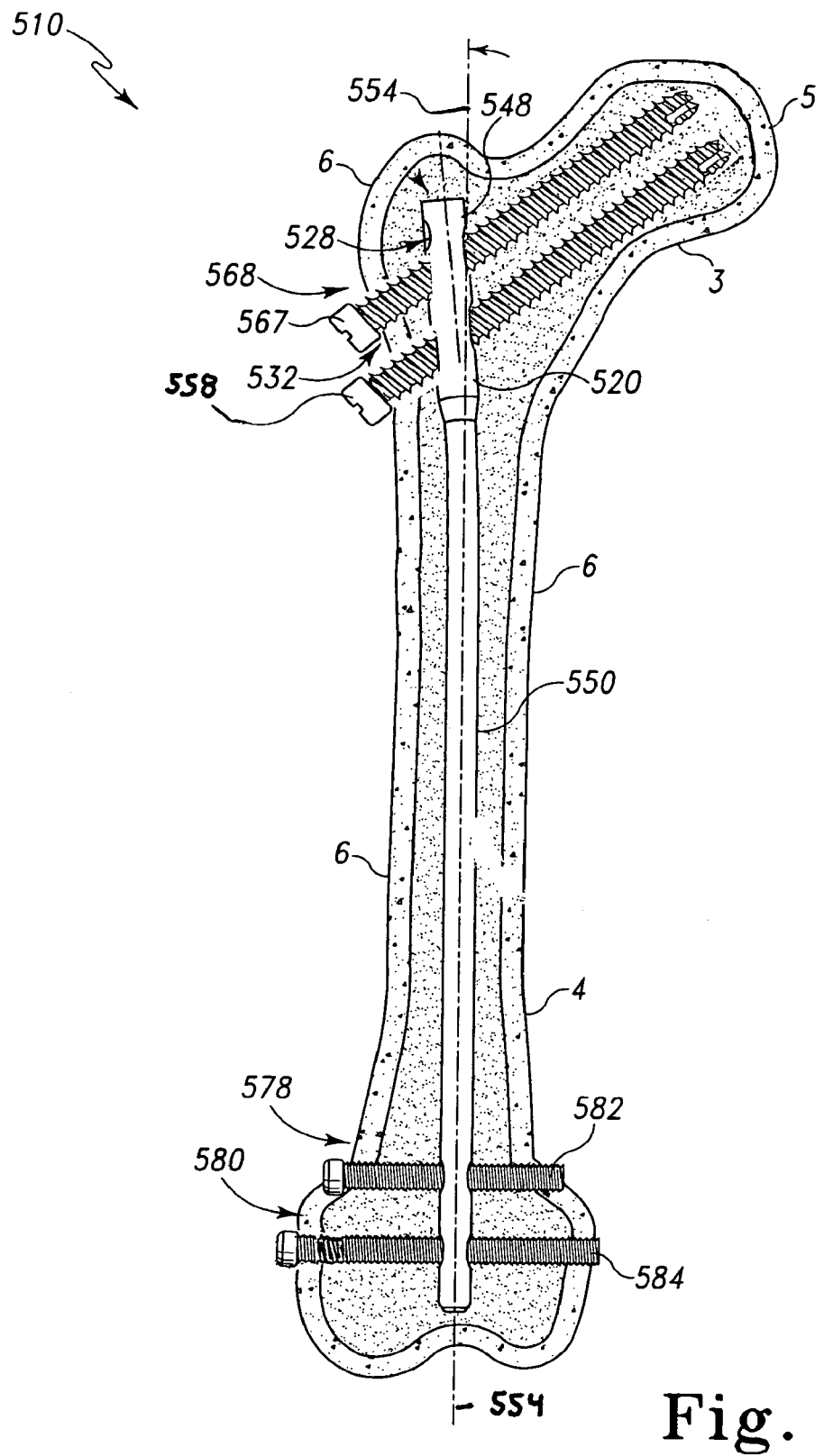
FIG. 30 is an anterior/posterior view of an intramedullary nail in accordance with an embodiment of the present invention in the form of a right femoral trochanteric nail implanted in a right femur with a piriforma fossa entry.
Figure 31:
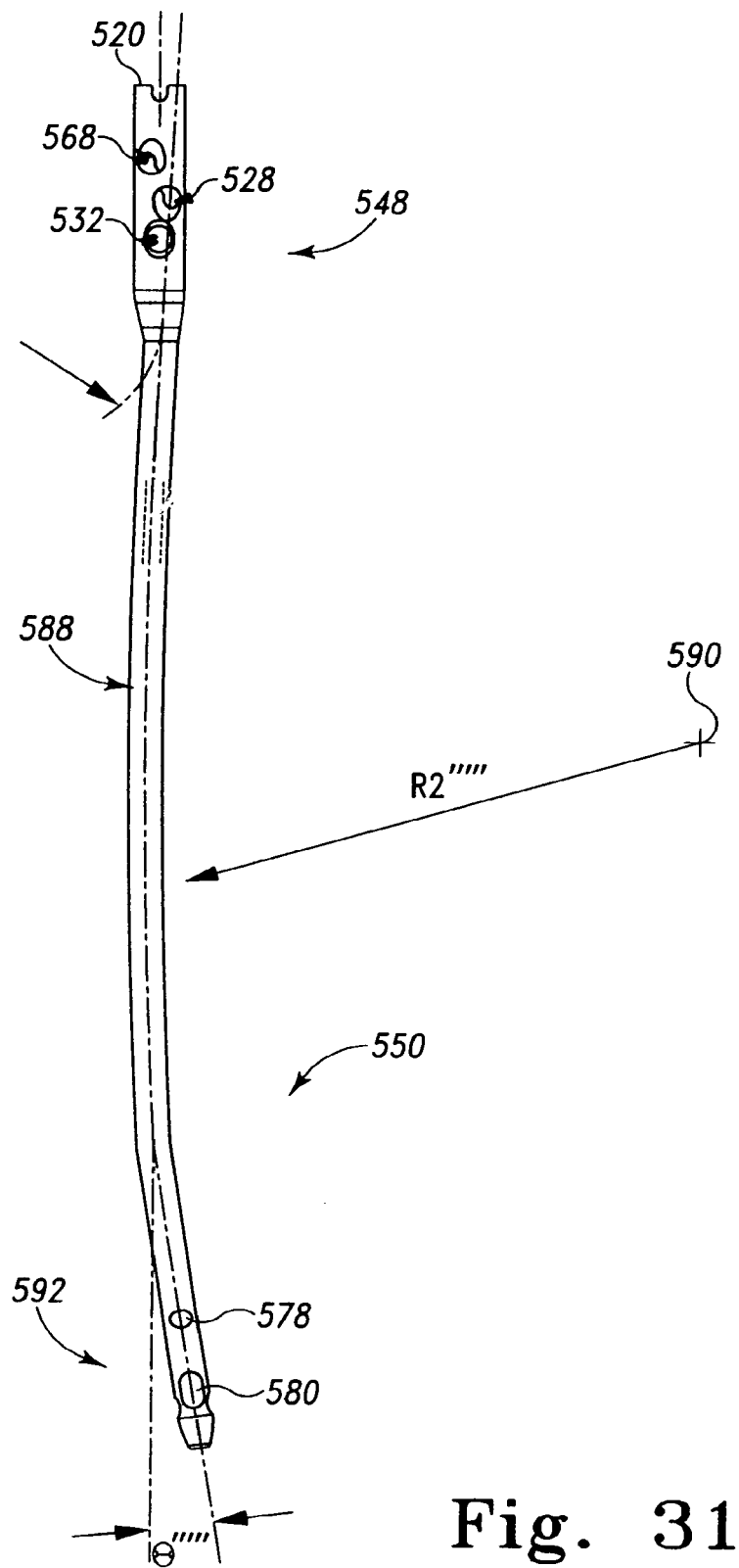
FIG. 31 is a medial/lateral view of the intramedullary nail of FIG. 30.
Figure 32:
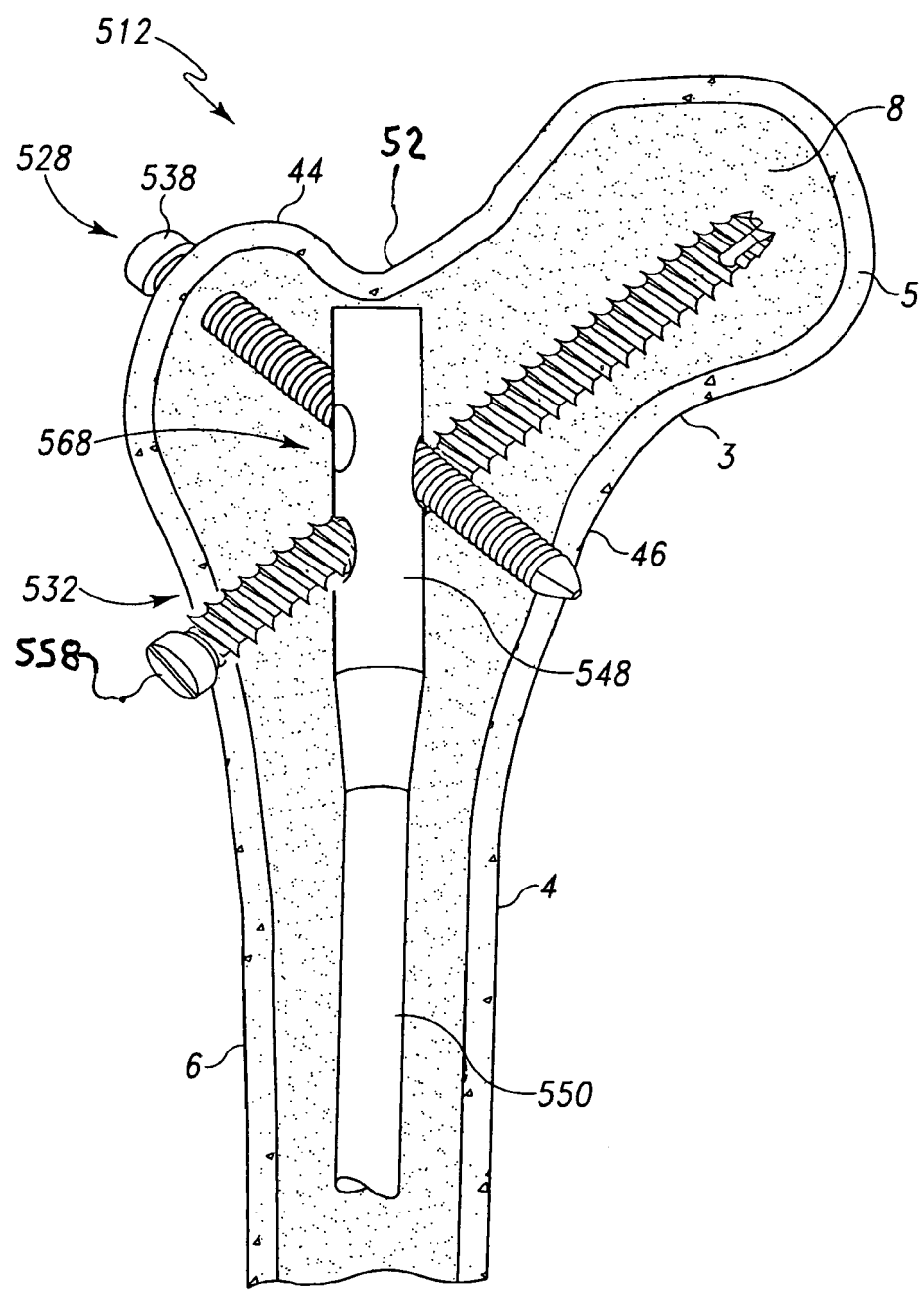
FIG. 32 is an enlarged partial anterior/posterior view of the proximal end of the intramedullary nail of FIG. 30 implanted in a right femur with a greater trochanter/lesser trochanter screw and a femoral neck screw in use to form a nail assembly according to another embodiment of the present invention.

Referring now to FIGS. 30, 31 and 32, the intramedullary nail of assembly of the present invention, may be in the form of a piriforma fossa nail for a right femur.

For example and as shown in FIG. 30, yet another embodiment of the present invention is shown as nail assembly 510. The nail assembly 510 includes an intramedullary nail 520. The nail 520 includes a proximal portion 548 and a distal portion 550. The proximal portion 548 and the distal portion 550 may be linear in the anterior/posterior view of FIG. 30. In other words, the proximal portion 548 and the distal portion 550 may be defined by a common longitudinal centerline 554.

The proximal portion 548 includes a first opening 528, a second opening 532 and a third opening 568.

The distal portion 550 of the nail 520 may include a first distal opening 578, which is transverse or perpendicular to the longitudinal axis 554 of the nail 520. The distal portion 550 of the nail 520 may further include a second distal opening 580 spaced from and parallel to the first distal opening 578.

The nail assembly 520 may include the nail 520, as well as, a second screw 558, which is slidably fitted into second opening 532. The second screw 558 may be a cancellous screw and may, as shown in FIG. 30, be fully threaded. The second screw 558 may extend into the neck 3 and head 5 of the femur 4. The nail assembly 510 may further include a third screw 567, which is slidably fitted into third opening 568. The third screw 567 may be in the form of a cancellous screw and may be parallel to and spaced from the second screw 558. The third screw 567 may extend into the neck 3 and head 5 of the femur 4. The third screw 567 may be used as an anti-rotation device to avoid the rotation of the head 5 with respect to the remainder of the femur 4.

The nail assembly 510 may further include a first distal screw 582 for slidably engagement with the first distal opening 578. The first distal screw 582 may be in the form of a cortical screw and may extend from first cortex 6 to the opposed cortex of the femur 4. The nail assembly 510 may further include a second distal screw 582 for slidably fitting into the second distal opening 580 of the nail 520. The second distal screw 584 may be similar to the first distal screw 582 and may be in the form of a cortical screw.

Referring now to FIG. 31, the nail 520 for use with the nail assembly 510 of FIG. 30 is shown in greater detail in a medial/lateral view. The nail 520 preferably has a shape conforming to that of the medullary canal of the right femur into which the nail 520 is to be inserted. The nail 520 may include the proximal portion 548 and the distal portion 550. The proximal portion 548 may include the first opening 528, the second opening 532 and the third opening 568.

The distal portion 550 may include an arcuate portion 588 having a generally bowed shape to conform with the medullary canal of the femur. The arcuate portion 588 may be defined by radius R2'''' extending from origin 590. The distal portion 550 may further include an end portion 592, which is generally linear. The end portion 592 may extend at an angle θ'''' from arcuate portion 588 and include the first distal opening 578 and the second distal opening 580. The first distal opening 578, as is shown in FIG. 25, may be generally cylindrical. The second distal opening 580 may, as shown in FIG. 25, have an oval shape.

Referring now to FIG. 32, yet another embodiment of the present invention is shown as nail assembly 512. The nail assembly 512 utilizes the nail 520 of FIGS. 30 and 31 and is used to repair neck fractures and greater trochanter 44 and lesser trochanter 46 fractures, or to be able to repair a fracture with both neck screw support and greater trochanter to lesser trochanter screw support. The nail assembly 520 includes the nail 520 as well as a first screw 538 and the second screw 558. The first screw 538 is fitted into first opening 528 of the nail 520 and extends from greater trochanter 44 to lesser trochanter 46. The first screw 538 may be in the form of a cortical screw and be able to engage the cortical wall 6 on both the greater trochanter and the lesser trochanter 546. The second screw 558 is fitted into second opening 532 and extends from cortical wall 6 of the femur 4 into neck 3 and head 5 of the femur 4. The second screw 558 may be in the form of a cancellous screw to engage with cancellous bone 8 located in the neck 3 and head 5.

Figure 33:
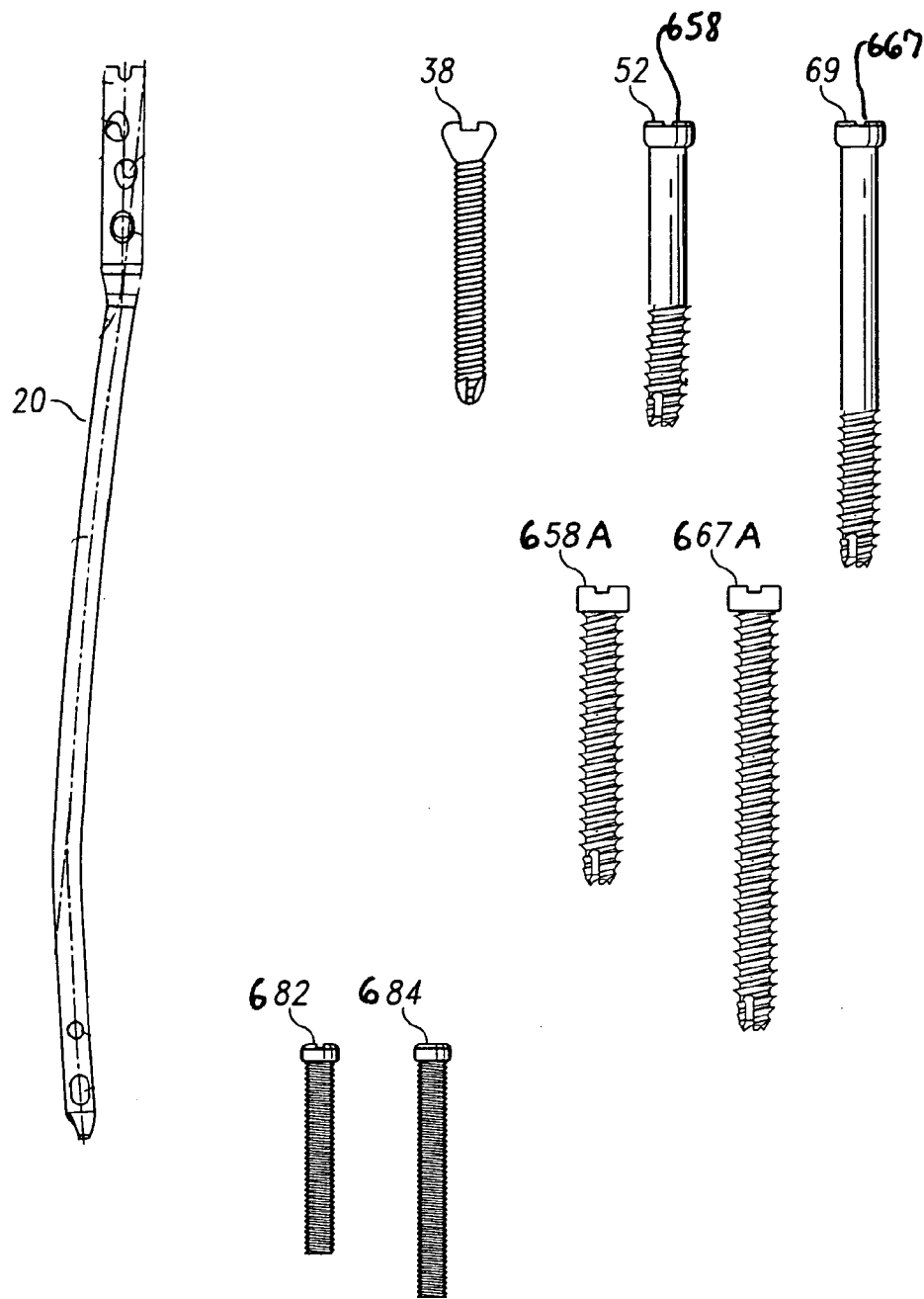
FIG. 33 is a plan view of a kit for use in performing trauma surgery in accordance with yet another embodiment of the present.

Referring now to FIG. 33, yet another embodiment of the present invention is shown as nail assembly or kit 600. The kit 600 includes nail 20. The kit 600 may also include a screw, for example, first screw 38. The kit 600 may further include a second proximal screw in the form of, for example, partially threaded second proximal screw 658. The kit 600 may further include third partially threaded screw 667. It should be appreciated that the kit 600 may include additional screws. For example, the kit 600 may include fully threaded screws for use in the femoral neck. The kit 600 may further include a second fully threaded screw 658A as well as a third fully threaded screw 667A. It should be appreciated that the kit 600 may further include distal screws, for example, first distal screw 682 and second distal screw 684.

Figure 34:
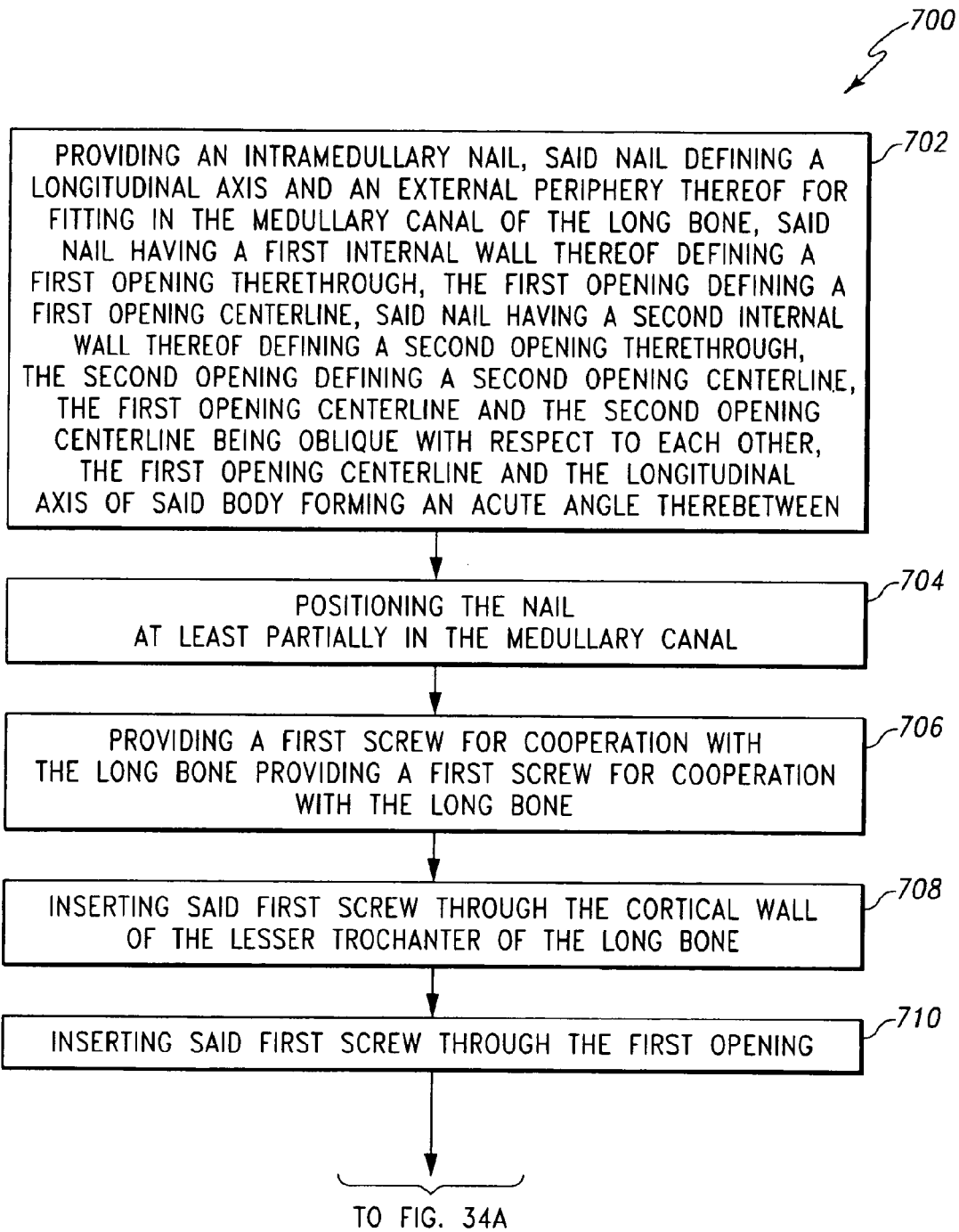
FIG. 34 is a first portion flow diagram of a method of performing trauma surgery in accordance with another embodiment of the present.
Figure 34A:
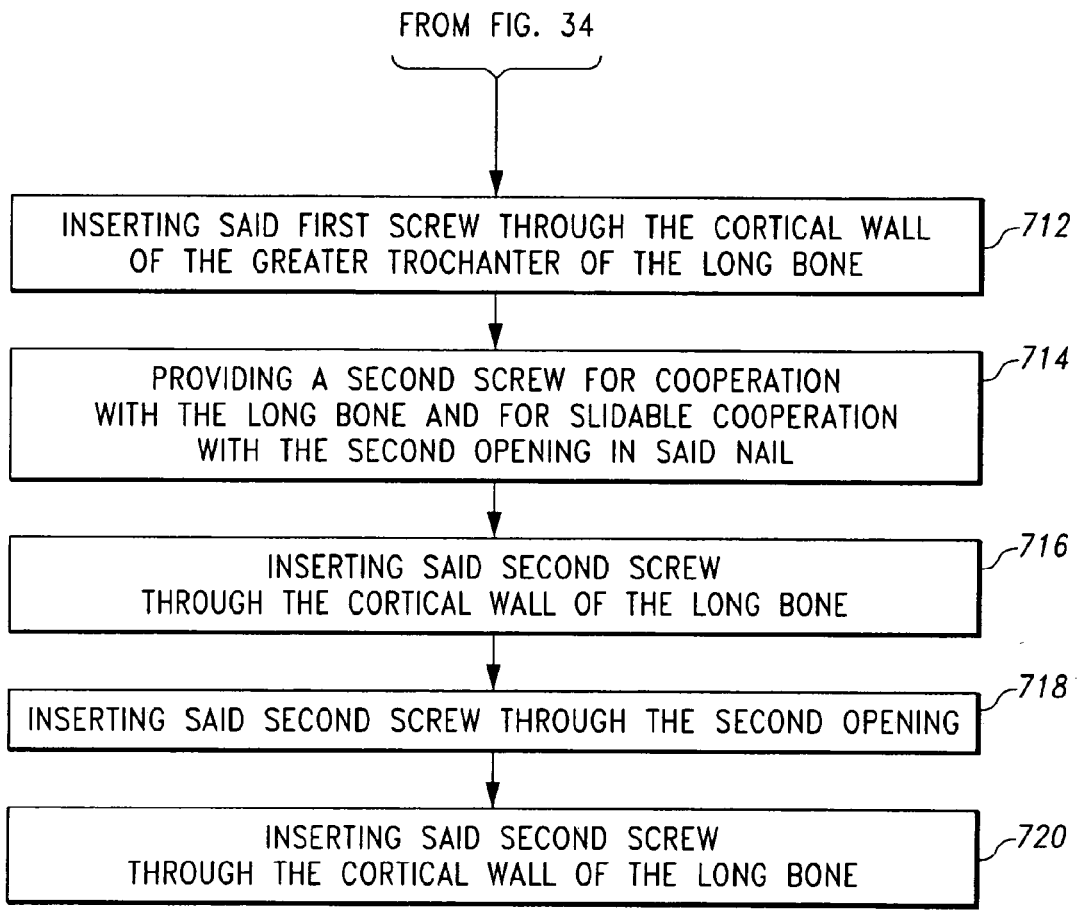
FIG. 34A is a second portion of the flow diagram of FIG. 34.

Referring now to FIG. 34, yet another embodiment of the present invention is shown as surgical technique or procedure 700. The surgical procedure 700 includes a first step 702 of providing an intramedullary nail. The nail includes a longitudinal axis and an external periphery. The external periphery is sized for fitting in the medullary canal of the long bone. The nail has a first internal wall defining a first opening. The first opening defines a first opening centerline. The nail has a second internal wall, which defines a second opening through the nail. The second opening defines a second opening centerline. The first opening centerline and the second opening centerline are oblique with respect to each other. The first opening centerline and the longitudinal axis of the body form an acute angle between them. The method 700 further includes a second step 704 of positioning the nail at least partially in the medullary canal. The method 700 further includes a third step 706 of providing a first screw for cooperation with the long bone and for slidable cooperation with the first opening and the nail. The method 700 further includes a fourth step 708 of inserting the first screw through the cortical wall of the lesser trochanter of the long bone. The method 700 further includes a fifth step 710 of inserting the first screw through the first opening, as well as a sixth step 712 of inserting the first screw through the cortical wall of the greater trochanter of the long bone. The method 700 further includes a seventh step 714 of providing a second screw for cooperation with the long bone and for slidable cooperation with the second opening in the nail. The method 700 further includes an eighth step 716 of inserting the second screw through the cortical wall of the long bone and a ninth step 718 of inserting the second screw through the second opening. The method 700 further includes a tenth step 720 of inserting the second screw through the cortical wall of the long bone.

Figure 35:
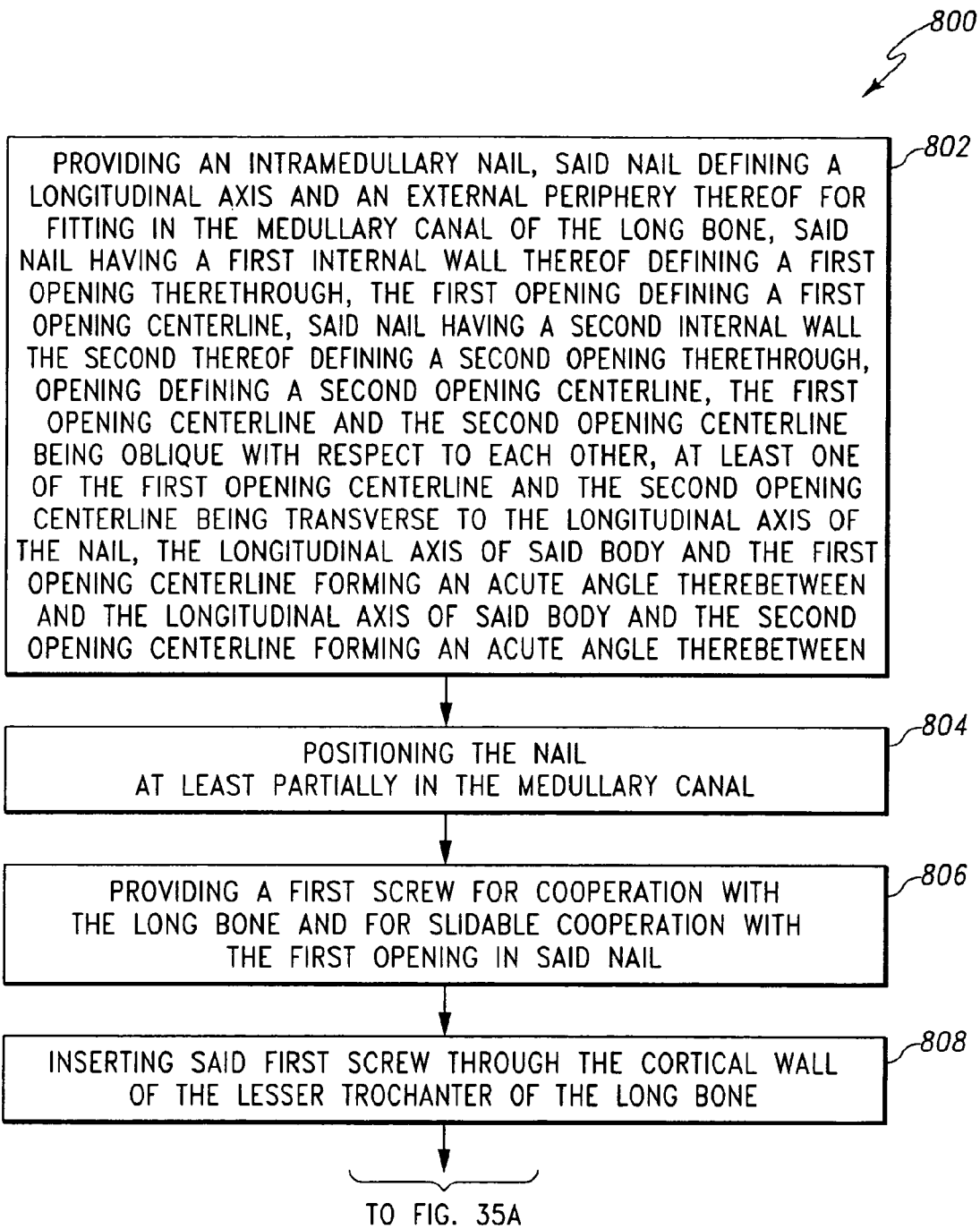
FIG. 35 is a first portion flow diagram of a method of performing trauma surgery in accordance with yet another embodiment of the present.
Figure 35A:
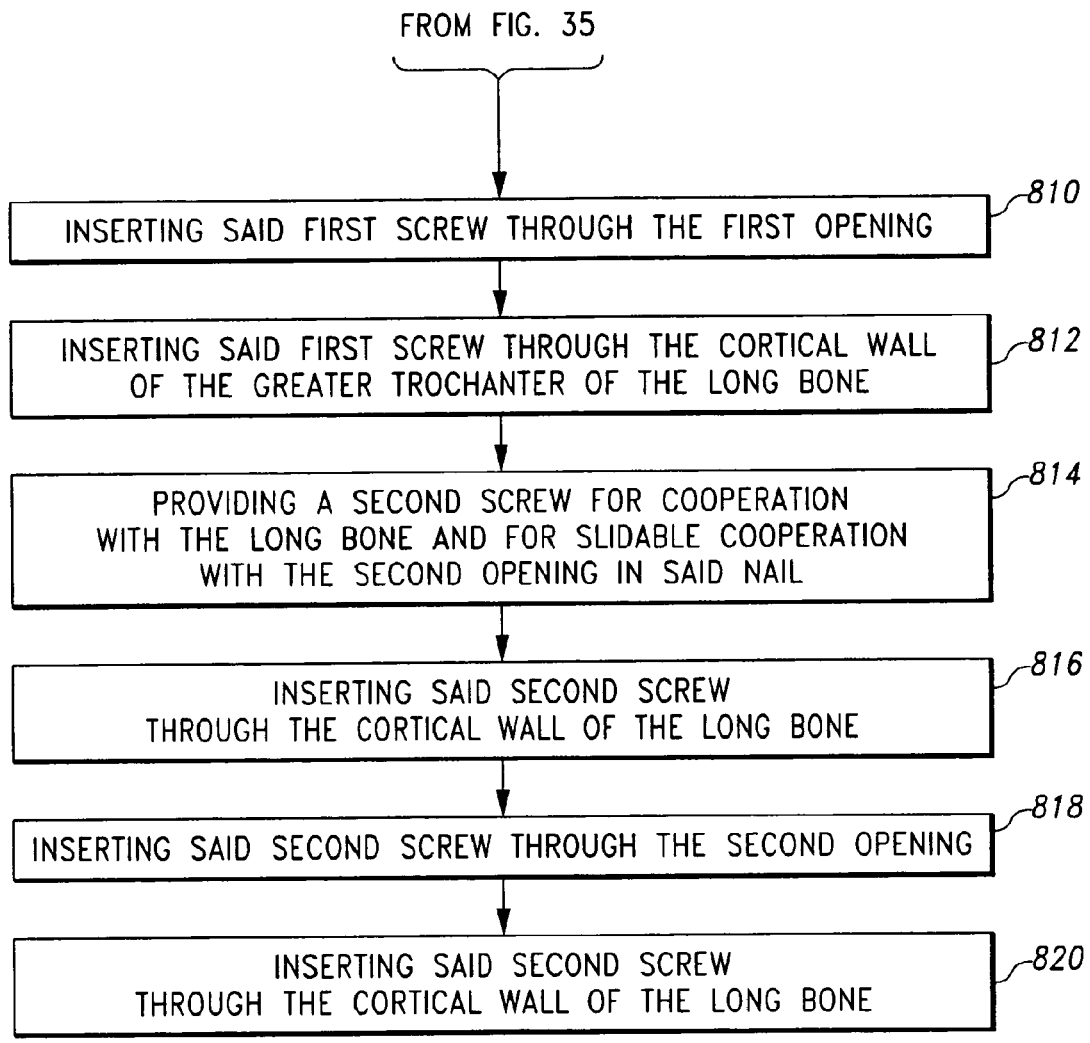
FIG. 35A is a second portion of the flow diagram of FIG. 35.

Referring now to FIG. 35, yet another embodiment of the present invention is shown as surgical procedure or surgical method 800. The method 800 includes a first step 802 of providing an intramedullary nail. The nail defines a longitudinal axis and an external periphery of the nail for fitting in the medullary canal of the long bone. The nail has a first internal wall, which defines a first opening through the nail. The first opening defines a first opening centerline. The nail has a second internal wall, which defines a second opening through the nail. The second opening defines a second opening centerline. The first opening centerline and the second opening centerline are oblique with respect to each other. The first opening centerline and/or the second opening centerline are transverse to the longitudinal axis of the nail. The longitudinal axis of the body and the first opening centerline form an acute angle between each other. The longitudinal axis of the body and the second opening centerline form an acute angel between each other. The method 800 includes a second step 804 of positioning the nail at least partially in the medullary canal. The method 800 includes a third step 806 of providing a first screw for cooperation with the long bone and for slidable cooperation with the first opening in the nail. The method 800 includes a fourth step 808 of inserting the first nail through the cortical wall of the lesser trochanter of the long bone. The method 800 includes a fifth step 810 of inserting the first screw through the first opening and a sixth step 812 of inserting the first screw through the cortical wall of the greater trochanter of the long bone. The method 800 further includes a seventh step 814 of providing a second screw for cooperation with the long bone and for slidable cooperation with the second opening in the nail. The method 800 includes an eighth step 816 of inserting the second screw through the cortical wall of the long bone and a ninth step 818 of inserting the second screw through the second opening. The method 800 includes a tenth step 820 of inserting the second screw through the cortical wall of the long bone.

Although the present invention and its advantages have been described in detail, it should be understood that various changes, substitutions, and alterations can be made therein without departing from the spirit and scope of the present invention as defined by the appended claims.

We claim:

1. A method of performing surgery on a femur comprising a medullary canal and cortical bone surrounding cancellous bone, the cortical bone defining a greater trochanter, a lesser trochanter, a femoral head and a femoral neck, said method comprising:
   positioning an intramedullary nail in the medullary canal of a femur, the nail comprising
      an elongate body having a proximal portion, a distal portion and a longitudinal axis, the proximal portion bent in a plane to form an acute angle between a longitudinal centerline of the distal portion and a longitudinal centerline of the proximal portion, said elongate body having a first transverse opening therethrough in the proximal portion, the first opening defining a first opening centerline, said elongate body having a second transverse opening therethrough in the proximal portion, the second opening defining a second opening centerline, wherein the first opening centerline and the second opening centerline do not intersect and are not coplanar with respect to each other, and wherein the longitudinal axis of said elongate body and the first opening centerline forming an acute angle therebetween and the longitudinal axis of said elongate body and the second opening centerline forming an acute angle therebetween;
   positioning a first bone fastener through the greater trochanter of the femur, through the elongate body along the first opening centerline, and into engagement with cortical one of the lesser trochanter of the femur; and
   positioning a second bone fastener through the elongate body along the second opening centerline, through the femoral neck of the femur, and into the femoral head of the femur, a longitudinal axis of the second bone fastener disposed in the plane, wherein the first and second bone fasteners form a generally x-shaped configuration when viewed transverse to the plane.

2. The method of claim 1, wherein at least a portion of said body is cannulated along the longitudinal axis.

3. The method of claim 1, wherein at least a portion of said body defines a groove along the longitudinal axis.

4. The method of claim 1, wherein at least one of the first opening and the second opening have a generally cylindrical shape.

5. The method of claim 1, wherein at least one of the first opening and the second opening have a generally oval shape.

6. The method of claim 1, wherein at least one of the first opening centerline and the second opening centerline intersects the longitudinal axis of said body.

7. The method of claim 1, further comprising a third opening defining a third opening centerline, the third opening centerline being substantially parallel with the second opening centerline and adapted to receive a third bone fastener.

8. The method of claim 1, wherein the external periphery of said body is substantially cylindrical.

9. The method of claim 8, wherein said nail defines a first portion having a first diameter and a second portion having a second diameter, the first diameter being larger than the second diameter.

10. The method of claim 9, wherein the first opening and the second opening are located in the first portion.

11. The method of claim 10, wherein said nail further defines a third opening therethrough, the third opening defining a centerline therethrough.

12. The method of claim 7, further comprising positioning a third bone fastener through the third opening, through the femoral neck of a femur, and into the femoral head of a femur.

13. The method of claim 6, wherein the first opening centerline and the second opening centerline define first and second planes, respectively, intersecting the longitudinal axis of said body, the first and second planes having an acute angle relative one another.

14. The method of claim 13, wherein the acute angle is about 10 degrees to 45 degrees.

15. The method of claim 1, wherein the first bone fastener comprises cortical threads threadedly engaging the cortical bone of the lesser trochanter.

16. The method of claim 15, wherein the second bone fastener comprises cancellous threads threadedly engaging the cancellous bone of the femoral head.

17. The method of claim 1, wherein the first bone fastener crosses the second bone fastener to form the generally x-shaped configuration at a point spaced from the intramedullary nail when viewed transverse to the plane.

18. A method of performing surgery on a femur comprising a medullary canal and cortical bone surrounding cancellous bone, the cortical bone defining a greater trochanter, a lesser trochanter, a femoral head and a femoral neck, the method comprising:
   positioning an intramedullary nail in the medullary canal of the femur, the intramedullary nail including a proximal portion and a distal portion, the proximal portion bent in a plane to form an acute angle between a longitudinal centerline of the distal portion and a longitudinal centerline of the proximal portion, the proximal portion defining first and second openings having first and second opening centerlines, respectively;
   positioning a first bone fastener through the greater trochanter of the femur, through the nail along the first opening centerline, and into engagement with cortical bone of the lesser trochanter; and
   positioning a second bone fastener through the nail along the second opening centerline, through the femoral neck of the femur, and into the femoral head of the femur;
   wherein the steps of positioning the first and second bone fasteners form a generally x-shaped configuration with the first and second bone fasteners when viewed transverse to the plane.

19. The method of claim 18, wherein a longitudinal axis of the second bone fastener is disposed in the plane.

20. The method of claim 18, wherein the first bone fastener crosses the second bone fastener to form the generally x-shaped configuration at a point spaced from the intramedullary nail when viewed transverse to the plane.

* * * * *